(12) United States Patent
Paredes et al.

(10) Patent No.: US 7,879,867 B2
(45) Date of Patent: Feb. 1, 2011

(54) CRYSTALLINE ANTIFUNGAL COMPOUNDS

(75) Inventors: Antonio Cánovas Paredes, Tona (ES);
Javier Bartroli Orpi, Barcelona (ES);
Elies Molins Grau, Bellaterra (ES);
Anna Roig Serra, Bellaterra (ES);
Kevin Meyer, Lebanon, IN (US); Keith Lorimer, West Lafayette, IN (US)

(73) Assignees: Palau Pharma, S.A., Palau-solita i Plegamans (ES); Stiefel Laboratories, Inc., Coral Gables, FL (US)

( * ) Notice: Subject to any disclaimer, the term of this patent is extended or adjusted under 35 U.S.C. 154(b) by 48 days.

(21) Appl. No.: 11/882,892

(22) Filed: Aug. 6, 2007

(65) Prior Publication Data

US 2008/0076787 A1    Mar. 27, 2008

Related U.S. Application Data

(60) Provisional application No. 60/929,408, filed on Jun. 26, 2007, provisional application No. 60/835,863, filed on Aug. 7, 2006.

(30) Foreign Application Priority Data

Aug. 7, 2006   (EP)   ................................. 06380225
Jun. 26, 2007  (EP)   ................................. 07380186

(51) Int. Cl.
*A61K 31/517*   (2006.01)
(52) U.S. Cl. ................................. 514/266.23; 544/284
(58) Field of Classification Search .................. 544/284
See application file for complete search history.

(56) References Cited

U.S. PATENT DOCUMENTS

| 5,807,854 A | 9/1998 | Bartroli et al. |
| 6,653,475 B2 | 11/2003 | Bartroli Orpi et al. |

FOREIGN PATENT DOCUMENTS

| EP | 0293500 | 12/1988 |
| EP | 0357241 | 3/1990 |
| EP | 0 659 751 A1 | 6/1995 |
| EP | 0567982 | 7/1998 |
| EP | 1282084 | 2/2003 |
| WO | WO 97/05130 | 2/1997 |
| WO | 98/39305 A1 | 9/1998 |

OTHER PUBLICATIONS

Singhal et al. Drug polymorphism and dosage form design: a practical perspective. 2004, Advanced Drug Delivery Reviews, 56, 335-347.*
Da Matta Guedes, Paulo Marcos et al., "Activity of the new triazole derivative albaconazole against Trypanosoma (Schizotrypanum) cruzi in dog hosts" Antimicrobial Agents and Chemotherapy, vol. 48, No. 11, Nov. 2004, p. 4286-4292.
Bartroli, et al., "New Azole Antifungals. 3. Synthesis and Antifungal Activity of 3-Substituted-4(3H)-quinazolinones", J. Med. Chem., 1998, 41, 1869-1882.
Bartroli, J., et al., "New Azole Antifungals. 3. Synthesis and Antifungal Activity of 3-Substituted-4(*3H*)-quinazolinones", *Journal of Medicinal Chemistry*, vol. 41, pp. 1869-1882, (1998).
Sorbera, L.A. et al., "Albaconazole: Antifungal", Drugs of the Future, 2003, pp. 529-537, vol. 28, No. 6.
Caira, Mino R., "Crystalline Polymorphism of Organic Compounds", Topics in Current Chemistry, 1998, pp. 163-208, vol. 198.
Extended European Search Report issued Aug. 20, 2010, in corresponding European Application No. 07836538.4, nine (9) pages.

* cited by examiner

*Primary Examiner*—James O Wilson
*Assistant Examiner*—Brian McDowell
(74) *Attorney, Agent, or Firm*—Gary M. Nath; Joshua B. Goldberg; Charles D. Niebylski

(57) ABSTRACT

Novel crystalline forms of (1R,2R)-7-chloro-3-[2-(2,4-difluorophenyl)-2-hydroxy-1-methyl-3-(1H-1,2,4-triazol-1-yl) propyl]quinazolin-4(3H)-one, pharmaceutical compositions containing these crystalline forms, methods of using these crystalline forms for treating and/or preventing various microbial and/or fungal infections or disorders, and processes for obtaining these crystalline forms. In particular, the present subject matter relates to the specific crystalline Forms I, II, III, IV, V, and VI of (1R,2R)-7-chloro-3-[2-(2,4-difluorophenyl)-2-hydroxy-1-methyl-3-(1H-1,2,4-triazol-1-yl)propyl] quinazolin -4(3H)-one, represented by formula II:

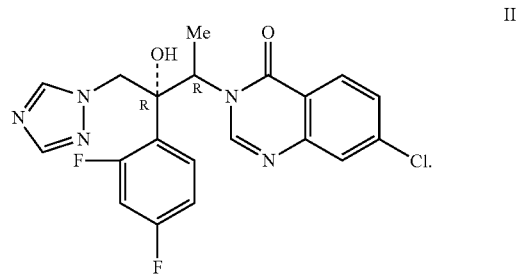

16 Claims, 27 Drawing Sheets

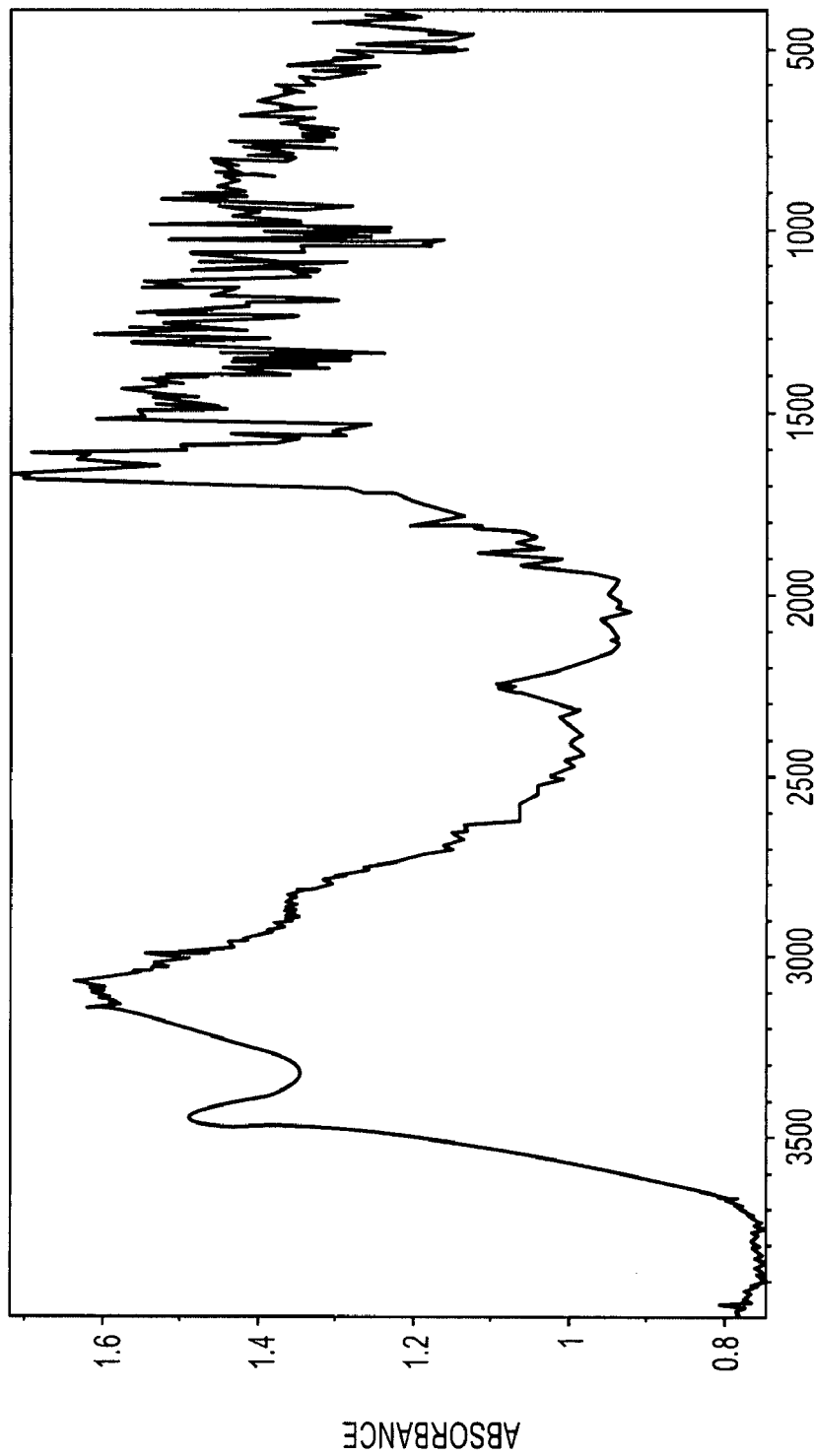

CRYSTALLINE ANTIFUNGAL COMPOUNDS

This application claims benefit of priority to U.S. provisional application No. 60/835,863, filed on Aug. 7, 2006, and U.S. provisional application No. 60/929,408, filed on Jun. 26, 2007.

FIELD OF THE INVENTION

The present subject matter relates to novel crystalline forms of (1R,2R)-7-chloro-3-[2-(2,4-difluorophenyl)-2-hydroxy-1-methyl-3-(1H-1,2,4-triazol-1-yl)propyl]quinazolin-4(3H)-one, pharmaceutical compositions containing these crystalline forms, methods of using these crystalline forms for treating and/or preventing various microbial and/or fungal infections or disorders, and processes for obtaining these crystalline forms. In particular, the present subject matter relates to the specific crystalline Forms I, II, III, IV V, and VI of (1R,2R)-7-chloro-3-[2-(2,4-difluorophenyl)-2-hydroxy-1-methyl-3-(1H-1,2,4-triazol-1-yl)propyl]quinazolin-4(3H)-one.

BACKGROUND OF THE INVENTION

U.S. Pat. No. 5,807,854 discloses various novel antifungal compounds of the formula I:

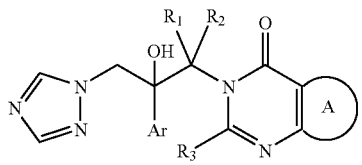

methods of making these compounds, pharmaceutical compositions containing these compounds, and their use in the treatment or prevention of fungal infections in animals. One of the specifically exemplified compounds falling within this genus is albaconazole, which also has the chemical name (1R,2R)-7-chloro-3-[2-(2,4-difluorophenyl)-2-hydroxy-1-methyl-3-(1H-1,2,4-triazol-1-yl)propyl]quinazolin-4(3H)-one. However, this patent does not disclose, refer to, or even suggest the benefits to obtaining specific crystalline forms of the compounds of formula I.

To prepare pharmaceutical compositions containing (1R,2R)-7-chloro-3-[2-(2,4-difluorophenyl)-2-hydroxy-1-methyl-3-(1H-1,2,4-triazol-1-yl)propyl]quinazolin-4(3H)-one for administration to mammals in accordance with exacting health registration requirements of the U.S. and international health registration authorities, e.g. the U.S. Food and Drug Administration's Good Manufacturing Practice ("GMP") requirements, there is a need to produce (1R,2R)-7-chloro-3-[2-(2,4-difluorophenyl)-2-hydroxy-1-methyl-3-(1H-1,2,4-triazol-1-yl)propyl]quinazolin-4(3H)-one in as pure a form as possible, especially a form having constant and consistent physical properties.

SUMMARY OF THE INVENTION

Accordingly, the present subject matter provides various crystalline forms of (1R,2R)-7-chloro-3-[2-(2,4-difluorophenyl)-2-hydroxy-1-methyl-3-(1H-1,2,4-triazol-1-yl)propyl]quinazolin-4(3H)-one represented by formula II:

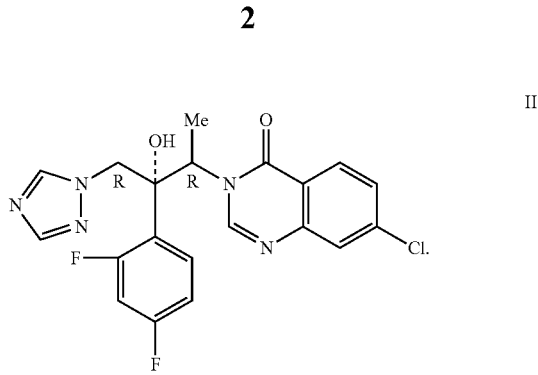

This compound was previously known to exist in an amorphous form. It has now been recognized that the compound can exist as one of six crystalline forms that are presently identified. Accordingly, a crystalline form of this compound is contemplated herein, such as a pure crystalline form substantially devoid of the compound's amorphous form and any residual solvent. In this regard, substantially pure crystalline forms of each of Forms I, II, III, IV, V, and VI of (1R,2R)-7-chloro-3-[2-(2,4-difluorophenyl)-2-hydroxy-1-methyl-3-(1H-1,2,4-triazol-1-yl)propyl]quinazolin-4(3H)-one are contemplated herein.

In this regard, a preferred embodiment of the present subject matter relates to a crystalline form of (1R,2R)-7-chloro-3-[2-(2,4-difluorophenyl)-2-hydroxy-1-methyl-3-(1H-1,2,4-triazol-1-yl)propyl]quinazolin-4(3H)-one comprising the reaction product of (1R,2R)-7-chloro-3-[2-(2,4-difluorophenyl)-2-hydroxy-1-methyl-3-(1H-1,2,4-triazol-1-yl)propyl]quinazolin-4(3H)-one and an organic solvent. In a further preferred embodiment, the present subject matter relates to a crystalline form of (1R,2R)-7-chloro-3-[2-(2,4-difluorophenyl)-2-hydroxy-1-methyl-3-(1H-1,2,4-triazol-1-yl)propyl]quinazolin-4(3H)-one comprising the reaction product of (1R,2R)-7-chloro-3-[2-(2,4-difluorophenyl)-2-hydroxy-1-methyl-3-(1H-1,2,4-triazol-1-yl)propyl]quinazolin-4(3H)-one and an organic solvent in the presence of water.

Another preferred embodiment of the present subject matter relates to a substantially pure crystalline form of (1R,2R)-7-chloro-3-[2-(2,4-difluorophenyl)-2-hydroxy-1-methyl-3-(1H-1,2,4-triazol-1-yl)propyl]quinazolin-4(3H)-one selected from the group consisting of Form I, Form II, Form III, Form IV, Form V, and Form VI.

Still another preferred embodiment of the present subject matter relates to a pharmaceutical composition comprising an anti-microbially or anti-fungally effective amount of a substantially pure crystalline Form I, II, III, IV, V, or VI of (1R,2R)-7-chloro-3-[2-(2,4-difluorophenyl)-2-hydroxy-1-methyl-3-(1H-1,2,4-triazol-1-yl)propyl]quinazolin-4(3H)-one or a pharmaceutically acceptable salt or derivative thereof and a pharmaceutically acceptable carrier. The crystalline Form II, Form IV, or Form VI is particularly preferred in this regard.

Still yet another preferred embodiment of the present subject matter relates to a method of treating and/or preventing microbial and/or fungal infections in a mammal comprising administering to a mammal in need thereof an effective amount of a substantially pure crystalline Form I, II, III, IV, V, or VI of (1R,2R)-7-chloro-3-[2-(2,4-difluorophenyl)-2-hydroxy-1-methyl-3-(1H-1,2,4-triazol-1-yl)propyl]quinazolin-4(3H)-one or a pharmaceutically acceptable salt or derivative thereof. The crystalline Form III, Form IV, or Form VI is particularly preferred in this regard.

Still yet another preferred embodiment of the present subject matter relates to a method of treating and/or preventing Chagas Disease in a mammal comprising administering to a mammal in need thereof an effective amount of a substantially pure crystalline Form I, II, III, IV, V, or VI of (1R,2R)-7-chloro-3-[2-(2,4-difluorophenyl)-2-hydroxy-1-methyl-3-(1H-1,2,4-triazol-1-yl)propyl]quinazolin-4(3H)-one or a pharmaceutically acceptable salt or derivative thereof. The crystalline Form III, Form IV, or Form VI is particularly preferred in this regard.

In still another preferred embodiment, the present subject matter relates to a process for preparing a crystalline Form I or II of (1R,2R)-7-chloro-3-[2-(2,4-difluorophenyl)-2-hydroxy-1-methyl-3-(1H-1,2,4-triazol-1-yl)propyl]quinazolin-4(3H)-one comprising:
  crystallizing a crystalline Form I or II of (1R,2R)-7-chloro-3-[2-(2,4-difluorophenyl)-2-hydroxy-1-methyl-3-(1H-1,2,4-triazol-1-yl)propyl]quinazolin-4(3H)-one from an amorphous form of (1R,2R)-7-chloro-3-[2-(2,4-difluorophenyl)-2-hydroxy-1-methyl-3-(1H-1,2,4-triazol-1-yl)propyl]quinazolin-4(3H)-one using supercritical $CO_2$ crystallization conditions.

Yet another preferred embodiment of the present subject matter relates to a process for preparing a crystalline Form III of (1R,2R)-7-chloro-3-[2-(2,4-difluorophenyl)-2-hydroxy-1-methyl-3-(1H-1,2,4-triazol-1-yl)propyl]quinazolin-4(3H)-one comprising:
  adding an amorphous form of (1R,2R)-7-chloro-3-[2-(2,4-difluorophenyl)-2-hydroxy-1-methyl-3-(1H-1,2,4-triazol-1-yl)propyl]quinazolin-4(3H)-one to a solvent selected from the group consisting of ethanol, ethyl acetate, dichloromethane, and a combination of ethanol and ethyl acetate to form a solution or suspension; and
  crystallizing a crystalline Form III of (1R,2R)-7-chloro-3-[2-(2,4-difluorophenyl)-2-hydroxy-1-methyl-3-(1H-1,2,4-triazol-1-yl)propyl]quinazolin-4(3H)-one from said solution or suspension.

Moreover, another preferred embodiment of the present subject matter relates to a process for preparing a crystalline Form III of (1R,2R)-7-chloro-3-[2-(2,4-difluorophenyl)-2-hydroxy-1-methyl-3-(1H-1,2,4-triazol-1-yl)propyl]quinazolin-4(3H)-one comprising:
  dissolving (1R,2R)-7-chloro-3-[2-(2,4-difluorophenyl)-2-hydroxy-1-methyl-3-(1H-1,2,4-triazol-1-yl)propyl]quinazolin-4(3H)-one in a solvent selected from the group consisting of ethanol, ethyl acetate, dichloromethane, and a combination of ethanol and ethyl acetate to form a solution;
  crystallizing crystalline Form III of (1R,2R)-7-chloro-3-[2-(2,4-difluorophenyl)-2-hydroxy-1-methyl-3-(1H-1,2,4-triazol-1-yl)propyl]quinazolin-4(3H)-one; and
  drying said crystalline Form III of (1R,2R)-7-chloro-3-[2-(2,4-difluorophenyl)-2-hydroxy-1-methyl-3-(1H-1,2,4-triazol-1-yl)propyl]quinazolin-4(3H)-one.

In a particularly preferred embodiment in this regard, the (1R,2R)-7-chloro-3-[2-(2,4-difluorophenyl)-2-hydroxy-1-methyl-3-(1H-1,2,4-triazol-1-yl)propyl]quinazolin-4(3H)-one dissolved in the solvent is the amorphous form of (1R,2R)-7-chloro-3-[2-(2,4-difluorophenyl)-2-hydroxy-1-methyl-3-(1H-1,2,4-triazol-1-yl)propyl]quinazolin-4(3H)-one. However, any form of (1R,2R)-7-chloro-3-[2-(2,4-difluorophenyl)-2-hydroxy-1-methyl-3-(1H-1,2,4-triazol-1-yl)propyl]quinazolin-4(3H)-one may be suitable for these purposes.

Still another preferred embodiment of the present subject matter relates to a process for preparing a crystalline Form III of (1R,2R)-7-chloro-3-[2-(2,4-difluorophenyl)-2-hydroxy-1-methyl-3-(1H-1,2,4-triazol-1-yl)propyl]quinazolin-4(3H)-one comprising:
  adding (1R,2R)-7-chloro-3-[2-(2,4-difluorophenyl)-2-hydroxy-1-methyl-3-(1H-1,2,4-triazol-1-yl)propyl]quinazolin-4(3H)-one to ethanol to form a solution or suspension;
  crystallizing crystalline Form III of (1R,2R)-7-chloro-3-[2-(2,4-difluorophenyl)-2-hydroxy-1-methyl-3-(1H-1,2,4-triazol-1-yl)propyl]quinazolin-4(3H)-one; and
  drying said crystalline Form III of (1R,2R)-7-chloro-3-[2-(2,4-difluorophenyl)-2-hydroxy-1-methyl-3-(1H-1,2,4-triazol-1-yl)propyl]quinazolin-4(3H)-one.

In another preferred embodiment, the present subject matter relates to a process for preparing a crystalline Form IV of (1R,2R)-7-chloro-3-[2-(2,4-difluorophenyl)-2-hydroxy-1-methyl-3-(1H-1,2,4-triazol-1-yl)propyl]quinazolin-4(3H)-one comprising:
  storing an amorphous form of (1R,2R)-7-chloro-3-[2-(2,4-difluorophenyl)-2-hydroxy-1-methyl-3-(1H-1,2,4-triazol-1-yl)propyl]quinazolin-4(3H)-one for 3 months at 40° C. and 75% HR;
  transforming some of said amorphous (1R,2R)-7-chloro-3-[2-(2,4-difluorophenyl)-2-hydroxy-1-methyl-3-(1H-1,2,4-triazol-1-yl)propyl]quinazolin-4(3H)-one to a crystalline Form IV of (1R,2R)-7-chloro-3-[2-(2,4-difluorophenyl)-2-hydroxy-1-methyl-3-(1H-1,2,4-triazol-1-yl)propyl]quinazolin-4(3H)-one during storage; and
  obtaining said crystalline Form IV of (1R,2R)-7-chloro-3-[2-(2,4-difluorophenyl)-2-hydroxy-1-methyl-3-(1H-1,2,4-triazol-1-yl)propyl]quinazolin-4(3H)-one.

In another preferred embodiment, the present subject matter relates to a process for preparing a crystalline Form IV of (1R,2R)-7-chloro-3-[2-(2,4-difluorophenyl)-2-hydroxy-1-methyl-3-(1H-1,2,4-triazol-1-yl)propyl]quinazolin-4(3H)-one comprising:
  dissolving (1R,2R)-7-chloro-3-[2-(2,4-difluorophenyl)-2-hydroxy-1-methyl-3-(1H-1,2,4-triazol-1-yl)propyl]quinazolin-4(3H)-one in ethanol to form a solution;
  adding the solution to water to form a suspension;
  stirring the suspension for more than 30 minutes;
  obtaining crystalline Form IV of (1R,2R)-7-chloro-3-[2-(2,4-difluorophenyl)-2-hydroxy-1-methyl-3-(1H-1,2,4-triazol-1-yl)propyl]quinazolin-4(3H)-one; and
  separating said crystalline Form IV of (1R,2R)-7-chloro-3-[2-(2,4-difluorophenyl)-2-hydroxy-1-methyl-3-(1H-1,2,4-triazol-1-yl)propyl]quinazolin-4(3H)-one.

In a particularly preferred embodiment in this regard, the (1R,2R)-7-chloro-3-[2-(2,4-difluorophenyl)-2-hydroxy-1-methyl-3-(1H-1,2,4-triazol-1-yl)propyl]quinazolin-4(3H)-one dissolved in the solvent is the amorphous form or Form III of (1R,2R)-7-chloro-3-[2-(2,4-difluorophenyl)-2-hydroxy-1-methyl-3-(1H-1,2,4-triazol-1-yl)propyl]quinazolin-4(3H)-one. However, any form of (1R,2R)-7-chloro-3-[2-(2,4-difluorophenyl)-2-hydroxy-1-methyl-3-(1H-1,2,4-triazol-1-yl)propyl]quinazolin-4(3H)-one may be suitable for these purposes.

In another preferred embodiment, the present subject matter relates to a process for preparing a crystalline Form V of (1R,2R)-7-chloro-3-[2-(2,4-difluorophenyl)-2-hydroxy-1-methyl-3-(1H-1,2,4-triazol-1-yl)propyl]quinazolin-4(3H)-one comprising:
  dissolving (1R,2R)-7-chloro-3-[2-(2,4-difluorophenyl)-2-hydroxy-1-methyl-3-(1H-1,2,4-triazol-1-yl)propyl]quinazolin-4(3H)-one in ethyl acetate to form a solution;
  adding hexane to the solution;
  optionally adding diethyl ether to the solution;

crystallizing crystalline Form V of (1R,2R)-7-chloro-3-[2-(2,4-difluorophenyl)-2-hydroxy-1-methyl-3-(1H-1,2,4-triazol-1-yl)propyl]quinazolin-4(3H)-one; and separating said crystalline Form V of (1R,2R)-7-chloro-3-[2-(2,4-difluorophenyl)-2-hydroxy-1-methyl-3-(1H-1,2,4-triazol-1-yl)propyl]quinazolin-4(3H)-one.

In a particularly preferred embodiment in this regard, the (1R,2R)-7-chloro-3-[2-(2,4-difluorophenyl)-2-hydroxy-1-methyl-3-(1H-1,2,4-triazol-1-yl)propyl]quinazolin-4(3H)-one dissolved in the solvent is the amorphous form of (1R,2R)-7-chloro-3-[2-(2,4-difluorophenyl)-2-hydroxy-1-methyl-3-(1H-1,2,4-triazol-1-yl)propyl]quinazolin-4(3H)-one. However, any form of (1R,2R)-7-chloro-3-[2-(2,4-difluorophenyl)-2-hydroxy-1-methyl-3-(1H-1,2,4-triazol-1-yl)propyl]quinazolin-4(3H)-one may be suitable for these purposes.

In another preferred embodiment, the present subject matter relates to a process for preparing a crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one comprising:

forming a solution or suspension of (1R,2R)-7-chloro-3-[2-(2,4-difluorophenyl)-2-hydroxy-1-methyl-3-(1H-1,2,4-triazol-1-yl)propyl]quinazolin-4(3H)-one in an aqueous ethanol solvent;

crystallizing Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one from said solution or suspension; and separating said crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one.

In one embodiment, the present subject matter relates to a process of making a substantially pure crystalline monohydrate form of (1R,2R)-7-chloro-3-[2-(2,4-difluorophenyl)-2-hydroxy-1-methyl-3-(1H-1,2,4-triazol-1-yl) propyl]quinazolin-4(3H)-one in certain organic solvents and water. This monohydrate form of (1R,2R)-7-chloro-3-[2-(2,4-difluorophenyl)-2-hydroxy-1-methyl-3-(1H-1,2,4-triazol-1-yl)propyl]quinazolin-4(3H)-one can also be known as Form VI of (1R,2R)-7-chloro-3-[2-(2,4-difluorophenyl)-2-hydroxy-1-methyl-3-(1H-1,2,4-triazol-1-yl) propyl]quinazolin-4(3H)-one. In one embodiment in this regard, the present subject matter relates to a process of making a substantially pure crystalline Form VI of (1R,2R)-7-chloro-3-[2-(2,4-difluorophenyl)-2-hydroxy-1-methyl-3-(1H-1,2,4-triazol-1-yl) propyl]quinazolin-4(3H)-one in certain organic solvents and water. In one particular embodiment of the present subject matter, the substantially pure crystalline Form VI of (1R,2R)-7-chloro-3-[2-(2,4-difluorophenyl)-2-hydroxy-1-methyl-3-(1H-1,2,4-triazol-1-yl) propyl]quinazolin-4(3H)-one, comprises the reaction product of (1R,2R)-7-chloro-3-[2-(2,4-difluorophenyl)-2-hydroxy-1-methyl-3-(1H-1,2,4-triazol-1-yl)propyl]quinazolin-4(3H)-one and an organic solvent and water. In a preferred embodiment, the organic solvent is a polar solvent. In a further preferred embodiment, the polar solvent is acetone or an alcohol. In a preferred embodiment in this regard, the alcohol is selected from the group consisting of ethanol, methanol, isopropanol, n-propanol, and acetone. In an especially preferred embodiment, the substantially pure crystalline Form VI of (1R,2R)-7-chloro-3-[2-(2,4-difluorophenyl)-2-hydroxy-1-methyl-3-(1H-1,2,4-triazol-1-yl) propyl]quinazolin-4(3H)-one, comprises the reaction product of (1R,2R)-7-chloro-3-[2-(2,4-difluorophenyl)-2-hydroxy-1-methyl-3-(1H-1,2,4-triazol-1-yl)propyl]quinazolin-4(3H)-one and ethanol and water. In another preferred embodiment, the substantially pure crystalline form of (1R,2R)-7-chloro-3-[2-(2,4-difluorophenyl)-2-hydroxy-1-methyl-3-(1H-1,2,4-triazol-1-yl) propyl]quinazolin-4(3H)-one comprises the monohydrate of (1R,2R)-7-chloro-3-[2-(2,4-difluorophenyl)-2-hydroxy-1-methyl-3-(1H-1,2,4-triazol-1-yl)propyl]quinazolin-4(3H)-one.

In another embodiment, the present subject matter relates to a process for preparing a crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one comprising:

forming a solution or suspension of (1R,2R)-7-chloro-3-[2-(2,4-difluorophenyl)-2-hydroxy-1-methyl-3-(1H-1,2,4-triazol-1-yl)propyl]quinazolin-4(3H)-one in an aqueous solvent and an organic solvent selected from the group consisting of ethanol, methanol, isopropanol, n-propanol, and acetone;

crystallizing Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one from said solution or suspension; and separating said crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one.

In another preferred embodiment, the present subject matter relates to a process for preparing a crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one comprising:

adding (1R,2R)-7-chloro-3-[2-(2,4-difluorophenyl)-2-hydroxy-1-methyl-3-(1H-1,2,4-triazol-1-yl)propyl]quinazolin-4(3H)-one to aqueous ethanol to form a solution or suspension;

crystallizing a crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one from said solution or suspension; and separating said crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one.

In an alternative preferred embodiment, the present subject matter relates to a process for preparing a crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one comprising:

adding (1R,2R)-7-chloro-3-[2-(2,4-difluorophenyl)-2-hydroxy-1-methyl-3-(1H-1,2,4-triazol-1-yl)propyl]quinazolin-4(3H)-one to ethanol to form a mixture;

adding said mixture to water to form a solution or suspension;

crystallizing a crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one from said solution or suspension; and separating said crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one. In a particularly preferred embodiment, the mixture of albaconazole and ethanol is a solution of albaconazole in ethanol.

In a particularly preferred embodiment in this regard, the (1R,2R)-7-chloro-3-[2-(2,4-difluorophenyl)-2-hydroxy-1-methyl-3-(1H-1,2,4-triazol-1-yl)propyl]quinazolin-4(3H)-one used to form the mixture, or the solution or suspension, is the amorphous form, Form III, Form IV, Form V, or combinations thereof of (1R,2R)-7-chloro-3-[2-(2,4-difluorophenyl)-2-hydroxy-1-methyl-3-(1H-1,2,4-triazol-1-yl)propyl]quinazolin-4(3H)-one. However, any form of (1R,2R)-7- chloro-3-[2-(2,4-difluorophenyl)-2-hydroxy-1-methyl-3-(1H-1,2,4-triazol-1-yl)propyl]quinazolin-4(3H)-one may be suitable for these purposes.

DETAILED DESCRIPTION OF THE INVENTION

Definitions

Figure 1:
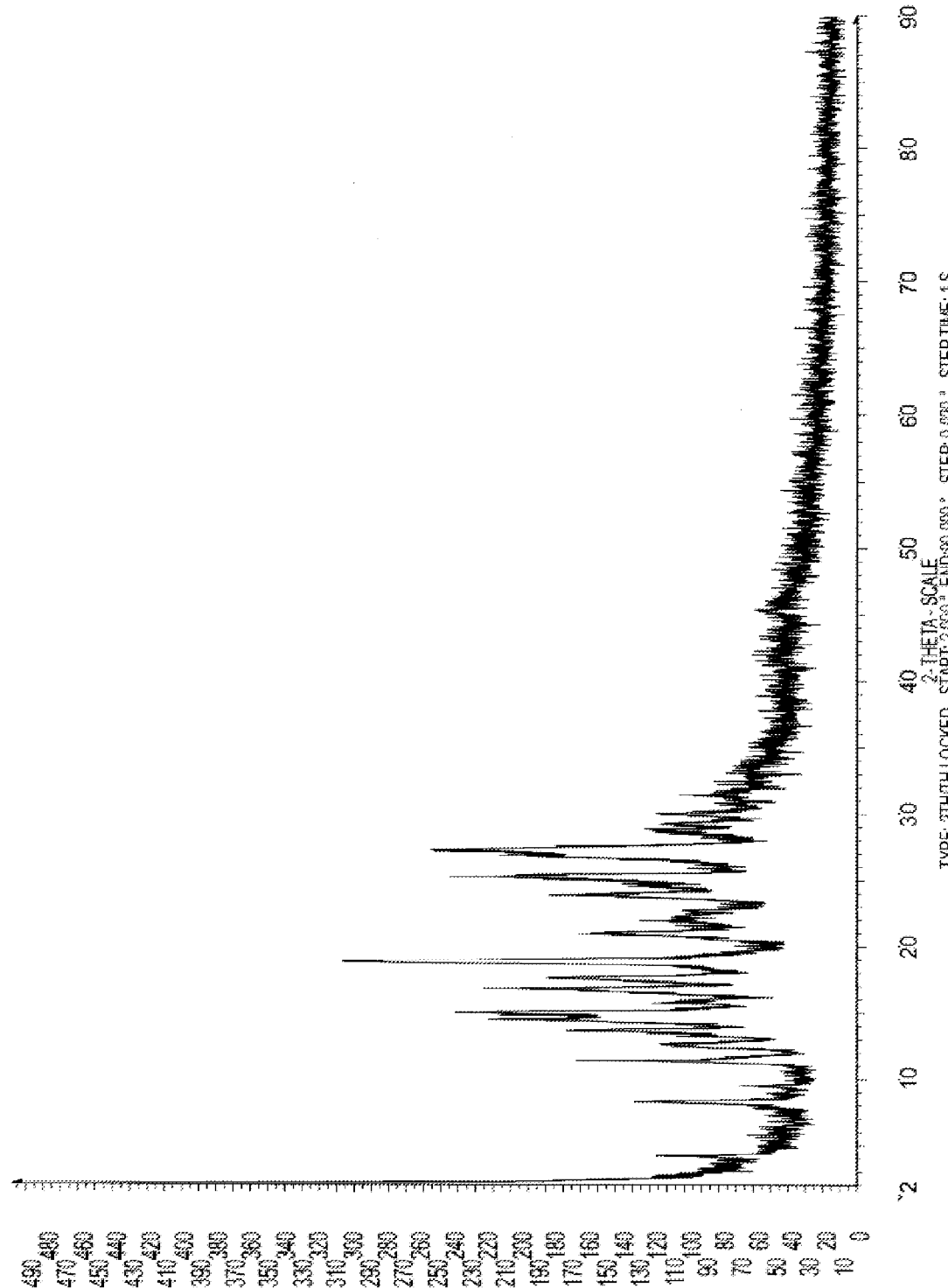
FIG. 1 presents a characteristic X-ray powder diffraction (XRPD) pattern of the crystalline Form I of (1R,2R)-7-chloro-3-[2-(2,4-difluorophenyl)-2-hydroxy-1-methyl-3-(1H-1,2,4-triazol-1-yl)propyl]quinazolin-4(3H)-one.

As used herein, the terms "administering", "administration", and like terms refer to any method which, in sound medical or cosmetic practice, delivers the composition to a subject in such a manner as to provide a therapeutic effect.

The phrase "aqueous solvent" as used herein refers to a solvent such as water or containing water. Other dissolved components may be present in small amounts, such as, for example, salts, buffers, and other components understood by one of ordinary skill in the art to be optionally present in an aqueous solution.

The phrase "crystalline form" as used herein refers to crystals of the same molecule having different physical properties as a result of the order of the molecules in the crystal lattice. Accordingly, as used herein the phrase "crystalline form" is intended to refer to different crystalline forms, polymorphs, pseudopolymorphs, and solvate forms of a single molecular entity. Different crystalline forms of a single compound may have different chemical, physical, mechanical, electrical, thermodynamic, and/or biological properties from each other. The differences in physical properties exhibited by crystalline forms affect pharmaceutical parameters such as storage stability, compressibility, density (important in formulation and product manufacturing), dissolution rates (an important factor in determining bio-availability), solubility, melting point, chemical stability, physical stability, powder flowability, compaction, and particle morphology. Each separate crystalline form of an individual compound will exhibit consistent chemical, physical, mechanical, electrical, thermodynamic, and biological properties.

The phrase "derivative" as used herein refers to any hydrate, solvate, salt, racemate, isomer, enantiomer, prodrug, metabolite, ester, or other analog or derivative of a particular chemical compound or molecule. The term "derivative" may also mean a modification to the disclosed compounds including, but not limited to, hydrolysis, reduction, or oxidation products, of the disclosed compounds. Hydrolysis, reduction, and oxidation reactions are known in the art.

Differences in stability can result from changes in chemical reactivity (e.g. differential oxidation, such that a dosage form discolors more rapidly when comprised of one crystalline form than when comprised of another crystalline form) or mechanical changes (e.g. tablets crumble on storage as a kinetically favored crystalline form converts to thermodynamically more stable crystalline form) or both (e.g. tablets of one crystalline form are more susceptible to breakdown at high humidity). As a result of solubility/dissolution differences, some crystalline form transitions affect potency and/or toxicity. In addition, the physical properties of the crystal may be important in processing; for example, one crystalline form might be more likely to form solvates or might be difficult to filter and wash free of impurities (i.e. particle shape and size distribution might be different between one crystalline form relative to the other).

As used herein, the phrases an "effective amount" or a "therapeutically effective amount" of an active agent or ingredient, or pharmaceutically active agent or ingredient, which are synonymous herein, refer to an amount of the pharmaceutically active agent sufficient enough to have a therapeutic effect upon administration. A therapeutically effective amount of the pharmaceutically active agent may, will, or is expected to cause a relief of symptoms. Effective amounts of the pharmaceutically active agent will vary with the particular condition or conditions being treated, the severity of the condition, the duration of the treatment, the specific components of the composition being used, and like factors.

As used herein, the phrase "pharmaceutically acceptable salts" refers to salts of certain ingredient(s) which possess the same activity as the unmodified compound(s) and which are neither biologically nor otherwise undesirable. A salt can be formed with, for example, organic or inorganic acids. Non-limiting examples of suitable acids include acetic acid, acetylsalicylic acid, adipic acid, alginic acid, ascorbic acid, aspartic acid, benzoic acid, benzenesulfonic acid, bisulfic acid, boric acid, butyric acid, camphoric acid, camphorsulfonic acid, carbonic acid, citric acid, cyclopentanepropionic acid, digluconic acid, dodecylsulfic acid, ethanesulfonic acid, formic acid, fumaric acid, glyceric acid, glycerophosphoric acid, glycine, glucoheptanoic acid, gluconic acid, glutamic acid, glutaric acid, glycolic acid, hemisulfic acid, heptanoic acid, hexanoic acid, hippuric acid, hydrobromic acid, hydrochloric acid, hydroiodic acid, hydroxyethanesulfonic acid, lactic acid, maleic acid, malic acid, malonic acid, mandelic acid, methanesulfonic acid, mucic acid, naphthylanesulfonic acid, naphthylic acid, nicotinic acid, nitrous acid, oxalic acid, pelargonic, phosphoric acid, propionic acid, saccharin, salicylic acid, sorbic acid, succinic acid, sulfuric acid, tartaric acid, thiocyanic acid, thioglycolic acid, thiosulfuric acid, tosylic acid, undecylenic acid, and naturally and synthetically derived amino acids.

If organic bases are used, poorly volatile bases are preferably employed, for example low molecular weight alkanolamines such as ethanolamine, diethanolamine, N-ethylethanolamine, N-methyldiethanolamine, triethanolamine, diethylaminoethanol, 2-amino-2-methyl-n-propanol, dimethylaminopropanol, 2-amino-2-methylpropanediol, and triisopropanolamine. Ethanolamine is particularly preferred in this regard. Further poorly volatile bases which may be mentioned are, for example, ethylenediamine, hexamethylenediamine, morpholine, piperidine, piperazine, cyclohexylamine, tributylamine, dodecylamine, N,N-dimethyldodecylamine, stearylamine, oleylamine, benzylamine, dibenzylamine, N-ethylbenzylamine, dimethylstearylamine, N-methylmorpholine, N-methylpiperazine, 4-methylcyclohexylamine, and N-hydroxyethylmorpholine.

Salts of quaternary ammonium hydroxides such as trimethylbenzylammonium hydroxide, tetramethylammonium hydroxide, or tetraethylammonium hydroxide can also by used, as can guanidine and its derivatives, in particular its alkylation products. However, it is also possible to employ as salt-forming agents, for example, low molecular weight alkylamines such as methylamine, ethylamine, or triethylamine. Suitable salts for the components to be employed according to the present subject matter are also those with inorganic cations, for example alkali metal salts, in particular sodium, potassium, or ammonium salts, alkaline earth metal salts such as, in particular, the magnesium or calcium salts, as well as salts with bi- or tetravalent cations, for example the zinc, aluminum, or zirconium salts. Also contemplated are salts with organic bases, such as dicyclohexylamine salts; methyl-D-glucamine; and salts with amino acids, such as arginine, lysine, and so forth. Also, the basic nitrogen-containing groups can be quaternized with such agents as lower alkyl halides, such as methyl, ethyl, propyl, and butyl chlorides, bromides, and iodides; dialkyl sulfates, such as dimethyl, diethyl, dibutyl, and diamyl sulfates; long chain halides, such as decyl, lauryl, myristyl, and stearyl chlorides, bromides, and iodides; asthma halides, such as benzyl and phenethyl bromides; and others. Water or oil-soluble or dispersible products are thereby obtained.

The phrase "reaction product" as used herein refers to any crystalline form obtained from the processes described herein, including but not limited to anhydrates, hydrates, polymorphs, solvates, N-oxides, and/or salts of these crystalline forms.

The phrase "substantially pure" as used herein refers to an individual crystalline form which is substantially devoid of all other crystalline forms, as well as degradation products of the crystalline form, the amorphous form, and any residual solvent, and is at least 85% pure on a % weight basis, unless otherwise specified. Preferably, the crystalline form has at least 90% purity on a % weight basis. More preferably, the crystalline form has at least 93% purity on a % weight basis. Yet more preferably, the crystalline form has at least 95% purity on a % weight basis. Yet even more preferably, the crystalline form has at least 97% purity on a % weight basis.

The term "treating" as used herein refers to the process of producing an effect on biological activity, function, health, or condition of an organism in which such activity is maintained, enhanced, diminished, or applied in a manner consistent with the general health and well-being of the organism.

Other terms as used herein are meant to be defined by their well-known meanings in the art.

Crystalline Forms of (1R,2R)-7-chloro-3-[2-(2,4-difluorophenyl)-2-hydroxy-1-methyl-3-(1H-1,2,4-triazol-1-yl)propyl]quinazolin-4(3H)-one Six different crystalline forms of the compound (1R,2R)-7-chloro-3-[2-(2,4-difluorophenyl)-2-hydroxy-1-methyl-3-(1H-1,2,4-triazol-1-yl)propyl]quinazolin-4(3H)-one have presently been identified: crystalline Forms I, II, III, IV, V, and VI. Of these different crystalline forms, the most preferred will provide an antifungal, antimicrobial drug having the lowest impurity content, most consistent product quality, most consistent physical characteristics including color, rate of dissolution, and ease of handling, and greatest long term stability in comparison to the other crystalline forms or the amorphous form.

Accordingly, the present subject matter relates to methods of identifying, obtaining, and purifying the various crystalline forms of (1R,2R)-7-chloro-3-[2-(2,4-difluorophenyl)-2-hydroxy-1-methyl-3-(1H-1,2,4-triazol-1-yl)propyl]quinazolin-4(3H)-one. These crystalline forms, namely Forms I-VI, were identified as six distinct crystal forms. Certain physical characteristics of these crystalline forms generated during crystallization studies, are as follows:

Form I: typically obtained by crystallizing the amorphous form using supercritical $CO_2$ crystallization conditions. This form displays a characteristic XRPD pattern, a characteristic IR spectrum, and a characteristic DSC profile.

Form II: typically obtained by crystallizing the amorphous form using supercritical $CO_2$ crystallization conditions. This form displays a characteristic XRPD pattern, a characteristic IR spectrum, and a characteristic DSC profile.

Form III: typically obtained under standard crystallization conditions using a variety of solvents such as ethanol, ethyl acetate, dichloromethane, and a combination of ethanol and ethyl acetate. This form displays a characteristic XRPD pattern, a characteristic IR spectrum, and a DSC profile with a strong endothermic peak onset at about 99° C. No degradation products of form III were detected after 6 months of storage at 30° C./65% RH and 25° C./60% RH.

Form IV: typically obtained by first dissolving any form in ethanol, then suspending this solution in water and stirring for a certain amount of time. This form may also be obtained directly from the amorphous form or Forms III or VI of (1R,2R)-7-chloro-3-[2-(2,4-difluorophenyl)-2-hydroxy-1-methyl-3-(1H-1,2,4-triazol-1-yl)propyl]quinazolin-4(3H)-one after storage for an extended period of time, for example after storage for 3 months at 40° C. and 75% RH, as some but not all of the original form converts to Form IV. This form displays a characteristic XRPD pattern, a characteristic IR spectrum, and a DSC profile with a strong endothermic peak onset at about 121° C.

Form V: typically obtained under standard crystallization conditions, typically by first dissolving the amorphous form in ethyl acetate, then adding hexane to this solution. Diethyl ether can then be optionally added. This form displays a characteristic XRPD pattern, a characteristic IR spectrum, and a DSC profile with a strong endothermic peak onset at about 108° C. Form V can best be characterized as a crystalline phase containing between about 2 and about 7% by weight of ethyl acetate and about 0.5 to about 2.5% by weight of hexane.

Form VI: typically obtained by slurrying (1R,2R)-7-chloro-3-[2-(2,4-difluorophenyl)-2-hydroxy-1-methyl-3-(1H-1,2,4-triazol-1-yl)propyl] quinazolin-4(3H)-one in aqueous ethanol or by slowly cooling a saturated aqueous ethanol solution that was seeded. This form may be obtained when the slurry comprises any other Form of (1R,2R)-7-chloro-3-[2-(2,4-difluorophenyl)-2-hydroxy-1-methyl-3-(1H-1,2,4-triazol-1-yl)propyl] quinazolin-4(3H)-one, such as, for example, the amorphous form, Form III, Form IV, Form V, or combinations thereof. Complete conversion of a Form III slurry at 45° C. to Form VI was noted after 3 hours in ethanol-water (1:9). High water activities are preferred for preparing Form VI to ensure that Forms III and/or V are not generated. This form displays a characteristic XRPD pattern, a characteristic IR spectrum, and a DSC profile with a strong endothermic peak ranging from about 102° C. to 108° C. Form VI can best be characterized as a non-hygroscopic monohydrate.

Purity

The present subject matter contemplates substantially pure and/or isolated crystalline Forms I, II, III, IV, V, and/or VI of (1R,2R)-7-chloro-3-[2-(2,4-difluorophenyl)-2-hydroxy-1-methyl-3-(1H-1,2,4-triazol-1-yl)propyl]quinazolin-4(3H)-one. In this regard, the present subject matter contemplates each of these crystalline forms which is substantially devoid of the amorphous form and of any residual solvent on a weight % basis, except as otherwise noted herein. In a preferred embodiment, the present subject matter particularly contemplates each of these crystalline forms free of any residual solvent, except as otherwise noted herein. Notwithstanding the above, crystalline forms contemplated herein may be in a hydrated form and thus may contain a certain amount of water. In preferred embodiments in this regard, crystalline forms may be formed as hydrates containing about 10% or less of water. In an alternative preferred embodiment, the present subject matter contemplates each of these crystalline forms further substantially devoid of the other crystalline forms.

In a preferred embodiment, the substantially pure crystalline form of (1R,2R)-7-chloro-3-[2-(2,4-difluorophenyl)-2-hydroxy-1-methyl-3-(1H-1,2,4-triazol-1-yl)propyl]quinazolin-4(3H)-one has less than about 10% by weight of a different crystalline form or an amorphous form of (1R,2R)-7-chloro-3-[2-(2,4-difluorophenyl)-2-hydroxy-1-methyl-3-(1H-1,2,4-triazol-1-yl)propyl]quinazolin-4(3H)-one as determined on a % weight basis.

In another preferred embodiment, the substantially pure crystalline form of (1R,2R)-7-chloro-3-[2-(2,4-difluorophenyl)-2-hydroxy-1-methyl-3-(1H-1,2,4-triazol-1-yl)propyl]quinazolin-4(3H)-one has at least 90% purity as defined by X-ray powder diffraction.

In another embodiment, the substantially pure crystalline form of (1R,2R)-7-chloro-3-[2-(2,4-difluorophenyl)-2-hydroxy-1-methyl-3-(1H-1,2,4-triazol-1-yl)propyl]quinazolin-4(3H)-one has less than about 10% by weight of any residual solvent.

In yet another embodiment, the substantially pure crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one is storage stable for at least 6 months at about 25° C. and 60% HR.

For example, the present subject matter contemplates crystalline Form I of (1R,2R)-7-chloro-3-[2-(2,4-difluorophenyl)-2-hydroxy-1-methyl-3-(1H-1,2,4-triazol-1-yl)propyl]quinazolin-4(3H)-one which has less than about 10% by weight of any residual solvent and the amorphous form of (1R,2R)-7-chloro-3-[2-(2,4-difluorophenyl)-2-hydroxy-1-methyl-3-(1H-1,2,4-triazol-1-yl)propyl]quinazolin-4(3H)-one as determined on a weight % basis; crystalline Form II of (1R,2R)-7-chloro-3-[2-(2,4-difluorophenyl)-2-hydroxy-1-methyl-3-(1H-1,2,4-triazol-1-yl)propyl]quinazolin-4(3H)-one which has less than about 10% by weight of any residual solvent and the amorphous form of (1R,2R)-7-chloro-3-[2-(2,4-difluorophenyl)-2-hydroxy-1-methyl-3-(1H-1,2,4-triazol-1-yl)propyl]quinazolin-4(3H)-one as determined on a weight % basis; crystalline Form III of (1R,2R)-7-chloro-3-[2-(2,4-difluorophenyl)-2-hydroxy-1-methyl-3-(1H-1,2,4-triazol-1-yl)propyl]quinazolin-4(3H)-one which has less than about 10% by weight of any residual solvent and the amorphous form of (1R,2R)-7-chloro-3-[2-(2,4-difluorophenyl)-2-hydroxy-1-methyl-3-(1H-1,2,4-triazol-1-yl)propyl]quinazolin-4(3H)-one as determined on a weight % basis; crystalline Form IV of (1R,2R)-7-chloro-3-[2-(2,4-difluorophenyl)-2-hydroxy-1-methyl-3-(1H-1,2,4-triazol-1-yl)propyl]quinazolin-4(3H)-one which has less than about 10% by weight of any residual solvent and the amorphous form of (1R,2R)-7-chloro-3-[2-(2,4-difluorophenyl)-2-hydroxy-1-methyl-3-(1H-1,2,4-triazol-1-yl)propyl]quinazolin-4(3H)-one as determined on a weight % basis; crystalline Form V of (1R,2R)-7-chloro-3-[2-(2,4-difluorophenyl)-2-hydroxy-1-methyl-3-(1H-1,2,4-triazol-1-yl)propyl]quinazolin-4(3H)-one which has less than about 10% by weight of any residual solvent and the amorphous form of (1R,2R)-7-chloro-3-[2-(2,4-difluorophenyl)-2-hydroxy-1-methyl-3-(1H-1,2,4-triazol-1-yl)propyl]quinazolin-4(3H)-one as determined on a weight % basis; and crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one which has less than about 10% by weight of any residual solvent and the amorphous form of (1R,2R)-7-chloro-3-[2-(2,4-difluorophenyl)-2-hydroxy-1-methyl-3-(1H-1,2,4-triazol-1-yl)propyl]quinazolin-4(3H)-one as determined on a weight % basis. Accordingly, the present subject matter contemplates each of these crystalline forms having at least 90% purity as defined by X-ray powder diffraction.

In an alternative example, the present subject matter further contemplates crystalline Form I of (1R,2R)-7-chloro-3-[2-(2,4-difluorophenyl)-2-hydroxy-1-methyl-3-(1H-1,2,4-triazol-1-yl)propyl]quinazolin-4(3H)-one which also has less than about 10% by weight of the crystalline forms II, III, IV, V, or VI of (1R,2R)-7-chloro-3-[2-(2,4-difluorophenyl)-2-hydroxy-1-methyl-3-(1H-1,2,4-triazol-1-yl)propyl]quinazolin-4(3H)-one as determined on a weight % basis; crystalline Form II of (1R,2R)-7-chloro-3-[2-(2,4-difluorophenyl)-2-hydroxy-1-methyl-3-(1H-1,2,4-triazol-1-yl)propyl]quinazolin-4(3H)-one which also has less than about 10% by weight of the crystalline forms 1, III, IV, V, or VI of (1R,2R)-7-chloro-3-[2-(2,4-difluorophenyl)-2-hydroxy-1-methyl-3-(1H-1,2,4-triazol-1-yl)propyl]quinazolin-4(3H)-one as determined on a weight % basis; crystalline Form III of (1R,2R)-7-chloro-3-[2-(2,4-difluorophenyl)-2-hydroxy-1-methyl-3-(1H-1,2,4-triazol-1-yl)propyl]quinazolin-4(3H)-one which also has less than about 10% by weight of the crystalline forms 1, II, IV, V, or VI of (1R,2R)-7-chloro-3-[2-(2,4-difluorophenyl)-2-hydroxy-1-methyl-3-(1H-1,2,4-triazol-1-yl)propyl]quinazolin-4(3H)-one as determined on a weight % basis; crystalline Form IV of (1R,2R)-7-chloro-3-[2-(2,4-difluorophenyl)-2-hydroxy-1-methyl-3-(1H-1,2,4-triazol-1-yl)propyl]quinazolin-4(3H)-one which also has less than about 10% by weight of the crystalline forms I, II, III, V, or VI of (1R,2R)-7-chloro-3-[2-(2,4-difluorophenyl)-2-hydroxy-1-methyl-3-(1H-1,2,4-triazol-1-yl)propyl]quinazolin-4(3H)-one as determined on a weight % basis; crystalline Form V of (1R,2R)-7-chloro-3-[2-(2,4-difluorophenyl)-2-hydroxy-1-methyl-3-(1H-1,2,4-triazol-1-yl)propyl]quinazolin-4(3H)-one which also has less than about 10% by weight of the crystalline forms 1, II, III, IV, or VI of (1R,2R)-7-chloro-3-[2-(2,4-difluorophenyl)-2-hydroxy-1-methyl-3-(1H-1,2,4-triazol-1-yl)propyl]quinazolin-4(3H)-one as determined on a weight % basis; and crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one which also has less than about 10% by weight of the crystalline forms I, II, III, IV, or V of (1R,2R)-7-chloro-3-[2-(2,4-difluorophenyl)-2-hydroxy-1-methyl-3-(1H-1,2,4-triazol-1-yl)propyl]quinazolin-4(3H)-one as determined on a weight % basis.

In a preferred embodiment, the present subject matter contemplates each of the crystalline forms I, II, III, IV, V, and VI of (1R,2R)-7-chloro-3-[2-(2,4-difluorophenyl)-2-hydroxy-1-methyl-3-(1H-1,2,4-triazol-1-yl)propyl]quinazolin-4(3H)-one which have less than about 7% by weight of any residual solvent and the amorphous form of (1R,2R)-7-chloro-3-[2-(2,4-difluorophenyl)-2-hydroxy-1-methyl-3-(1H-1,2,4-triazol-1-yl)propyl]quinazolin-4(3H)-one as determined on a weight % basis, or have a 93% purity as defined by X-ray powder diffraction. In an alternative preferred embodiment in this regard, the present subject matter may further contemplate each of the crystalline forms I, II, III, IV, V, and VI of (1R,2R)-7-chloro-3-[2-(2,4-difluorophenyl)-2-hydroxy-1-methyl-3-(1H-1,2,4-triazol-1-yl)propyl]quinazolin-4(3H)-one which also have less than about 7% by weight of the other crystalline forms of (1R,2R)-7-chloro-3-[2-(2,4-difluorophenyl)-2-hydroxy-1-methyl-3-(1H-1,2,4-triazol-1-yl)propyl]quinazolin-4(3H)-one as determined on a weight % basis.

In a particularly preferred embodiment, the present subject matter contemplates each of the crystalline forms 1, II, III, IV, V, and VI of (1R,2R)-7-chloro-3-[2-(2,4-difluorophenyl)-2-hydroxy-1-methyl-3-(1H-1,2,4-triazol-1-yl)propyl]quinazolin-4(3H)-one which have less than about 5% by weight of any residual solvent and the amorphous form of (1R,2R)-7-chloro-3-[2-(2,4-difluorophenyl)-2-hydroxy-1-methyl-3-(1H-1,2,4-triazol-1-yl)propyl]quinazolin-4(3H)-one as determined on a weight % basis, or have a 95% purity as defined by X-ray powder diffraction. In an alternative preferred embodiment in this regard, the present subject matter may further contemplate each of the crystalline forms I, II, III, IV, V, and VI of (1R,2R)-7-chloro-3-[2-(2,4-difluorophenyl)-2-hydroxy-1-methyl-3-(1H-1,2,4-triazol-1-yl)propyl]quinazolin-4(3H)-one which also have less than about 5% by weight of the other crystalline forms of (1R,2R)-7-chloro-3-[2-(2,4-difluorophenyl)-2-hydroxy-1-methyl-3-(1H-1,2,4-triazol-1-yl)propyl]quinazolin-4(3H)-one as determined on a weight % basis.

In another preferred embodiment, the present subject matter contemplates each of the crystalline forms I, II, III, IV, V, and VI of (1R,2R)-7-chloro-3-[2-(2,4-difluorophenyl)-2-hydroxy-1-methyl-3-(1H-1,2,4-triazol-1-yl)propyl]quinazolin-4(3H)-one which have less than about 10% by weight of any residual solvent. In a further preferred embodiment in this regard, the present subject matter contemplates each of the crystalline forms I, II, III, IV, and V of (1R,2R)-7-chloro-3-[2-(2,4-difluorophenyl)-2-hydroxy-1-methyl-3-(1H-1,2,4-triazol-1-yl)propyl]quinazolin-4(3H)-one which have less than 7%, more preferably less than 5% by weight, of any residual solvent. In another further preferred embodiment in this regard, the present subject matter contemplates the crystalline form VI of (1R,2R)-7-chloro-3-[2-(2,4-difluorophenyl)-2-hydroxy-1-methyl-3-(1H-1,2,4-triazol-1-yl)propyl]quinazolin-4(3H)-one which has less than 7%, more preferably less than 5% by weight of any residual solvent. In a most preferred embodiment, the crystalline form free of residual solvent is crystalline Form VI. Notwithstanding the above, Form VI contemplated herein is a monohydrated form and thus contains a certain amount of water. In preferred embodiments in this regard, Form VI is a monohydrate containing about 4% water.

In one embodiment, the substantially pure crystalline form of (1R,2R)-7-chloro-3-[2-(2,4-difluorophenyl)-2-hydroxy-1-methyl-3-(1H-1,2,4-triazol-1-yl)propyl]quinazolin-4(3H)-one has a characteristic X-ray powder diffraction (XRPD) pattern that may contain at least one, more preferably at least 3, most preferably at least 5,2-theta position selected from the group consisting of those at about 2.72, 3.74, 4.08, 4.11, 4.15, 4.17, 5.31, 5.73, 5.83, 6.22, 6.28, 6.35, 7.5, 7.77, 7.96, 7.98, 8.15, 8.22, 8.33, 8.35, 8.37, 8.80, 9.01, 9.39, 9.61, 10.1, 11.16, 11.25, 11.29, 11.35, 11.4, 11.47, 11.61, 11.66, 11.7, 12.1, 12.41, 12.44, 12.49, 12.57, 12.6, 13.06, 13.09, 13.15, 13.21, 13.29, 13.3, 13.34, 13.62, 13.64, 14.11, 14.33, 14.34, 14.41, 14.42, 14.43, 14.5, 14.52, 14.68, 14.89, 14.93, 14.98, 15.0, 15.09, 15.43, 15.57, 15.7, 15.74, 15.93, 15.95, 16.0, 16.35, 16.6, 16.68, 16.74, 16.77, 16.90, 16.98, 17.0, 17.21, 17.27, 17.3, 17.4, 17.49, 17.56, 17.57, 17.63, 17.71, 17.91, 18.25, 18.66, 18.74, 18.79, 18.8, 18.82, 18.86, 18.9, 19.2, 19.30, 19.32, 19.37, 19.7, 20.36, 20.43, 20.85, 20.88, 21.08, 21.1, 21.47, 21.78, 21.79, 21.88, 22.12, 22.27, 22.3, 22.31, 22.49, 22.62, 22.82, 22.88, 23.20, 23.58, 23.64, 23.82, 23.84, 23.86, 23.9, 24.2, 24.26, 24.63, 24.78, 24.8, 25.02, 25.11, 25.2, 25.3, 25.32, 25.7, 25.95, 26, 26.03, 26.2, 26.65, 26.7, 26.74, 26.77, 26.83, 26.86, 27.04, 27.12, 27.21, 27.25, 27.35, 27.44, 27.6, 28.00, 28.43, 28.5, 28.57, 28.6, 28.74, 28.9, 28.96, 28.98, 29.05, 29.11, 29.16, 29.3, 29.38, 29.41, 29.7, 29.81, 29.97, 30.0, 30.07, 30.13, 30.14, 30.5, 30.73, 30.75, 30.8, 30.91, 30.98, 31.3, 31.35, 31.35, 31.58, 31.78, 32.05, 32.36, 32.41, 33.3, 33.48, 33.61, 33.63, 33.7, 33.9, 34.3, 34.35, 34.62, 34.94, 35.0, 35.5, 36.5, 36.7, 37.4, 39.5, 45.28, 46.1, 48.87, and 55.02+/−0.2.

In a preferred embodiment, the substantially pure crystalline form of (1R,2R)-7-chloro-3-[2-(2,4-difluorophenyl)-2-hydroxy-1-methyl-3-(1H-1,2,4-triazol-1-yl)propyl]quinazolin-4(3H)-one has a characteristic X-ray powder diffraction (XRPD) pattern containing at least one, more preferably at least 3, most preferably at least 5, 2-theta position selected from the group consisting of those at about 4.08, 4.11, 4.15, 4.17, 5.73, 5.83, 6.22, 6.28, 6.35, 7.5, 7.77, 7.96, 7.98, 8.15, 8.22, 8.33, 8.35, 8.37, 8.8, 9.39, 9.61, 10.1, 11.16, 11.25, 11.29, 11.35, 11.4, 11.47, 11.66, 11.7, 12.41, 12.44, 12.49, 12.57, 12.6, 13.09, 13.15, 13.29, 13.62, 13.64, 14.34, 14.41, 14.42, 14.5, 14.89, 14.98, 15.57, 15.95, 16.0, 16.74, 16.77, 16.9, 17.49, 17.56, 17.57, 17.63, 18.66, 18.74, 18.79, 18.86, 18.9, 20.85, 21.08, 21.2, 21.2, 21.2, 23.82, 23.84, 23.86, 24.78, 24.8, 25.3, 25.11, 25.2, 25.32, 25.7, 26.65, 26.83, 27.04, 27.12, 27.35, 27.44, and 30.13+/−0.2. In other preferred embodiments, the substantially pure crystal form of (1R,2R)-7-chloro-3-[2-(2,4-difluorophenyl)-2-hydroxy-1-methyl-3-(1H-1,2,4-triazol-1-yl)propyl]quinazolin-4(3H)-one has two or more of the XRPD peaks identified above. In further embodiments, the crystal form has three or more of the XRPD peaks identified above. In yet further embodiments, the crystal form has four or more of the XRPD peaks identified above.

In one embodiment, the substantially pure crystalline form of (1R,2R)-7-chloro-3-[2-(2,4-difluorophenyl)-2-hydroxy-1-methyl-3-(1H-1,2,4-triazol-1-yl)propyl]quinazolin-4(3H)-one has an infrared spectra pattern that may contain at least one spectral line position selected from the group consisting of those at 1723.8, 1677.0, 1676.0, 1673.3, 1671.0, 1607, 1601.0, 1600.0, 1599.0, 1557.5, 1555, 1503.3, 1501.2, 1499.4, 1498.8, 1498.3, 1468, 1462.7, 1462.6, 1462.3, 1462.2, 1404.1, 1403.9, 1403.0, 1402.4, 1400, 1361, 1319.8, 1319.4, 1318.4, 1318.2, 1318.0, 1316, 1280, 1274.4, 1273.9, 1272.5, 1272.4, 1254.9, 1254.6, 1254.1, 1253.7, 1253.0, 1218, 1210.2, 1170.2, 1170.0, 1169.9, 1165, 1139.1, 1139.0, 1138.7, 1138.0, 1137.7, 1102.7, 1102.1, 1102, 1101.8, 1101.6, 1062.2, 1061.8, 1061.4, 1060.7, 1060.2, 1016.4, 1014, 976, 967.4, 967.2, 967.0, 966.7, 938, 933.5, 932.8, 932.7, 932.6, 902.8, 902.7, 902.4, 902.0, 857.4, 857.2, 855.5, 845.0, 801.5, 801.4, 801.3, 801.3, 801.2, 785.9, 785.8, 785.1, 783.6, 782.9, 760, 698, 694.0, 693.9, 693.8, 693.5, 677.9, 677.7, 677.2, 665.4, 665.1, 664.9, 664.1, 663.6, 631.8, 631.7, 630.7, 630.2, 630.1, 533.4, 532.7, and 411.6 cm$^{-1}$. In another embodiment, the substantially pure crystalline form of (1R, 2R)-7-chloro-3-[2-(2,4-difluorophenyl)-2-hydroxy-1-methyl-3-(1H-1,2,4-triazol-1-yl)propyl]quinazolin-4(3H)-one is characterized as having an infrared spectra having at least two of the characteristic infrared spectral peak positions identified above. In yet another embodiment, the substantially pure crystalline form is characterized as having an infrared spectra having at least three of the characteristic infrared spectral peak positions identified above. In a further embodiment, the substantially pure crystalline form is characterized as having an infrared spectra having at least four of the characteristic infrared spectral peak positions identified above.

In a preferred embodiment, the substantially pure crystalline form of (1R,2R)-7-chloro-3-[2-(2,4-difluorophenyl)-2-hydroxy-1-methyl-3-(1H-1,2,4-triazol-1-yl)propyl]quinazolin-4(3H)-one has a characteristic X-ray powder diffraction (XRPD) pattern selected from the group consisting of (A) 2-theta positions at about 4.11, 8.22, 9.39, 11.29, 12.41, 13.62, 16.74, 17.57, 18.79, 23.82, and 25.2+/−0.2; (B) 2-theta positions at about 6.35, 7.98, 8.37, 11.4, 11.7, 12.6, 13.15, 14.42, 14.98, 16.77, 17.56, 18.86, 21.08, 23.84, 25.32, 26.83, and 27.35+/−0.2; (C) 2-theta positions at about 4.08, 5.73, 6.22, 7.77, 8.15, 8.80, 11.25, 11.47, 12.44, 13.09, 15.57, 17.63, 18.66, 20.85, 26.65, and 27.12+/−0.2; (D) 2-theta positions at about 4.15, 7.5, 8.33, 9.61, 11.16, 12.49, 13.29, 13.64, 14.41, 16.90, 18.74, 24.78, and 25.11+/−0.2; (E) 2-theta positions at about 4.17, 5.83, 6.28, 7.96, 8.35, 11.35, 11.66, 12.57, 14.34, 14.89, 15.95, 16.74, 17.49, 18.9, 21.1, 23.86, 25.3, 27.04, 27.44, and 30.13+/−0.2; and (F) 2-theta positions at about 21.1, 24.8, and 25.7+/−0.2.

In one embodiment, the substantially pure crystalline Form I of (1R,2R)-7-chloro-3-[2-(2,4-difluorophenyl)-2-hydroxy-1-methyl-3-(1H-1,2,4-triazol-1-yl)propyl]quinazolin-4(3H)-one has a characteristic X-ray powder diffraction (XRPD) pattern that may contain at least one 2-theta position selected from the group consisting of those at about 4.11, 8.22, 9.39, 11.29, 12.41, 13.21, 13.62, 14.43, 14.93, 15.7, 16.74, 17.3, 17.57, 18.79, 20.88, 21.88, 22.62, 23.64, 23.82, 25.2, 26.77, 27.21, 28.57, 29.16, 29.97, 30.75, 31.35, 45.28, 48.87, and 55.02+/−0.2.

In a preferred embodiment, the substantially pure crystalline Form I of (1R,2R)-7-chloro-3-[2-(2,4-difluorophenyl)-2-hydroxy-1-methyl-3-(1H-1,2,4-triazol-1-yl)propyl]quinazolin-4(3H)-one has a characteristic X-ray powder diffraction (XRPD) pattern that may contain at least one 2-theta position selected from the group consisting of those at about 4.11, 8.22, 9.39, 11.29, 12.41, 13.62, 16.74, 17.57, 18.79, 23.82, and 25.2+/−0.2. In other preferred embodiments, the substantially pure crystal Form I has two or more of the XRPD peaks identified above. In further embodiments, the crystal form has three or more of the XRPD peaks identified above. In yet further embodiments, the crystal form has four or more of the XRPD peaks identified above.

In one embodiment, the substantially pure crystalline Form I of (1R,2R)-7-chloro-3-[2-(2,4-difluorophenyl)-2-hydroxy-1-methyl-3-(1H-1,2,4-triazol-1-yl)propyl]quinazolin-4 (3H)-one has an infrared spectra pattern that may contain at least one spectral line position selected from the group consisting of those at 1673.3, 1600.0, 1557.5, 1501.2, 1462.7, 1403.9, 1319.4, 1273.9, 1254.6, 1139.0, 1101.8, 1061.8, 967.2, 902.7, 801.3, 783.6, 664.1, and 630.1 cm$^{-1}$.

In another embodiment, the substantially pure crystalline Form II of (1R,2R)-7-chloro-3-[2-(2,4-difluorophenyl)-2-hydroxy-1-methyl-3-(1H-1,2,4-triazol-1-yl)propyl]quinazolin-4(3H)-one has a characteristic X-ray powder diffraction 0 pattern that may contain at least one 2-theta position selected from the group consisting of those at about 2.72, 5.31, 6.35, 7.98, 8.37, 9.01, 11.4, 11.7, 12.6, 13.15, 14.42, 14.98, 15.93, 16.77, 17.56, 17.91, 18.86, 19.37, 21.08, 21.78, 22.31, 22.82, 23.84, 25.32, 26, 26.83, 27.35, 28.5, 28.96, 29.38, 30.14, 31.58, 32.41, 33.63, 34.94, and 46.1+/−0.2.

In a preferred embodiment, the substantially pure crystalline Form II of (1R,2R)-7-chloro-3-[2-(2,4-difluorophenyl)-2-hydroxy-1-methyl-3-(1H-1,2,4-triazol-1-yl)propyl]quinazolin-4(3H)-one has a characteristic X-ray powder diffraction (XRPD) pattern that may contain at least one 2-theta position selected from the group consisting of those at about 6.35, 7.98, 8.37, 11.4, 11.7, 12.6, 13.15, 14.42, 14.98, 16.77, 17.56, 18.86, 21.08, 23.84, 25.32, 26.83, and 27.35+/−0.2. In other preferred embodiments, the substantially pure crystal Form II has two or more of the XRPD peaks identified above. In further embodiments, the crystal form has three or more of the XRPD peaks identified above. In yet further embodiments, the crystal form has four or more of the XRPD peaks identified above.

In one embodiment, the substantially pure crystalline Form II of (1R,2R)-7-chloro-3-[2-(2,4-difluorophenyl)-2-hydroxy-1-methyl-3-(1H-1,2,4-triazol-1-yl)propyl]quinazolin-4(3H)-one has an infrared spectra pattern that may contain at least one spectral line position selected from the group consisting of those at 1677.0, 1600.0, 1557.5, 1498.8, 1462.3, 1318.2, 1272.4, 1253.0, 1170.2, 1137.7, 1102.0, 1060.7, 967.0, 932.6, 902.0, 857.2, 801.3, 785.1, 693.5, 664.9, and 630.7 cm$^{-1}$.

In another embodiment, the substantially pure crystalline Form III of (1R,2R)-7-chloro-3-[2-(2,4-difluorophenyl)-2-hydroxy-1-methyl-3-(1H-1,2,4-triazol-1-yl)propyl]quinazolin-4(3H)-one has a characteristic X-ray powder diffraction (XRPD) pattern that may contain at least one 2-theta position selected from the group consisting of those at about 4.08, 5.73, 6.22, 7.77, 8.15, 8.80, 11.25, 11.47, 12.44, 13.09, 14.33, 14.68, 14.89, 15.57, 16.35, 16.68, 17.27, 17.63, 18.66, 19.32, 20.85, 22.12, 22.49, 23.58, 24.63, 25.02, 26.65, 27.12, 28.74, 29.11, 29.81, 31.35, and 33.48+/−0.2.

In a preferred embodiment, the substantially pure crystalline Form III of (1R,2R)-7-chloro-3-[2-(2,4-difluorophenyl)-2-hydroxy-1-methyl-3-(1H-1,2,4-triazol-1-yl)propyl]quinazolin-4(3H)-one has a characteristic X-ray powder diffraction (XRPD) pattern that may contain at least one 2-theta position selected from the group consisting of those at about 4.08, 5.73, 6.22, 7.77, 8.15, 8.80, 11.25, 11.47, 12.44, 13.09, 15.57, 17.63, 18.66, 20.85, 26.65, and 27.12+/−0.2. In other preferred embodiments, the substantially pure crystal Form III has two or more of the XRPD peaks identified above. In further embodiments, the crystal form has three or more of the XRPD peaks identified above. In yet further embodiments, the crystal form has four or more of the XRPD peaks identified above.

In one embodiment, the substantially pure crystalline Form III of (1R,2R)-7-chloro-3-[2-(2,4-difluorophenyl)-2-hydroxy-1-methyl-3-(1H-1,2,4-triazol-1-yl)propyl]quinazolin-4(3H)-one has an infrared spectra pattern that may contain at least one spectral line position selected from the group consisting of those at 1677.0, 1600.0, 1557.5, 1498.3, 1462.6, 1403.0, 1318.4, 1272.5, 1254.1, 1170.0, 1138.7, 1101.6, 1060.2, 1016.4, 966.7, 932.7, 902.4, 855.5, 801.5, 785.8, 694.0, 677.9, 665.4, 631.7, 532.7, and 411.6 cm$^{-1}$.

In another embodiment, the substantially pure crystalline Form IV of (1R,2R)-7-chloro-3-[2-(2,4-difluorophenyl)-2-hydroxy-1-methyl-3-(1H-1,2,4-triazol-1-yl)propyl]quinazolin-4(3H)-one has a characteristic X-ray powder diffraction (XRPD) pattern that may contain at least one 2-theta position selected from the group consisting of those at about 3.74, 4.15, 7.5, 8.33, 9.61, 11.16, 11.61, 12.49, 13.29, 13.64, 14.41, 15.43, 15.74, 16.90, 17.71, 18.25, 18.74, 19.30, 20.43, 21.78, 23.20, 24.26, 24.78, 25.11, 26.03, 26.86, 27.25, 28.00, 29.05, 30.07, 30.91, and 32.05+/−0.2.

In a preferred embodiment, the substantially pure crystalline Form IV of (1R,2R)-7-chloro-3-[2-(2,4-difluorophenyl)-2-hydroxy-1-methyl-3-(1H-1,2,4-triazol-1-yl)propyl] quinazolin-4(3H)-one has a characteristic X-ray powder diffraction (XRPD) pattern that may contain at least one 2-theta position selected from the group consisting of those at about 4.15, 7.5, 8.33, 9.61, 11.16, 12.49, 13.29, 13.64, 14.41, 16.90, 18.74, 24.78, and 25.11+/−0.2. In other preferred embodiments, the substantially pure crystal Form IV has two or more of the XRPD peaks identified above. In further embodiments, the crystal form has three or more of the XRPD peaks identified above. In yet further embodiments, the crystal form has four or more of the XRPD peaks identified above.

In one embodiment, the substantially pure crystalline Form IV of (1R,2R)-7-chloro-3-[2-(2,4-difluorophenyl)-2-hydroxy-1-methyl-3-(1H-1,2,4-triazol-1-yl)propyl]quinazolin-4(3H)-one has an infrared spectra pattern that may contain at least one spectral line position selected from the group consisting of those at 1671.0, 1601.0, 1557.5, 1503.3, 1462.7, 1404.1, 1319.8, 1274.4, 1254.9, 1210.2, 1139.1, 1102.1, 1062.2, 967.4, 933.5, 902.8, 845.0, 801.4, 782.9, 693.8, 677.7, 663.6, and 630.2 cm$^{-1}$.

In another embodiment, the substantially pure crystalline Form V of (1R,2R)-7-chloro-3-[2-(2,4-difluorophenyl)-2-hydroxy-1-methyl-3-(1H-1,2,4-triazol-1-yl)propyl]quinazolin-4(3H)-one has a characteristic X-ray powder diffraction (XRPD) pattern that may contain at least one 2-theta position selected from the group consisting of those at about 4.17, 5.83, 6.28, 7.96, 8.35, 11.35, 11.66, 12.57, 13.06, 13.34, 14.11, 14.34, 14.52, 14.89, 15.09, 15.95, 16.74, 16.98, 17.21, 17.49, 17.91, 18.82, 18.9, 20.36, 21.1, 21.47, 21.79, 22.27, 22.88, 23.86, 25.3, 25.95, 26.2, 26.74, 27.04, 27.44, 28.43, 28.98, 29.41, 30.13, 30.73, 30.98, 31.78, 32.36, 33.61, 33.9, 34.35, and 34.62+/−0.2.

In a preferred embodiment, the substantially pure crystalline Form V of (1R,2R)-7-chloro-3-[2-(2,4-difluorophenyl)-2-hydroxy-1-methyl-3-(1H-1,2,4-triazol-1-yl)propyl] quinazolin-4(3H)-one has a characteristic X-ray powder diffraction (XRPD) pattern that may contain at least one 2-theta position selected from the group consisting of those at about 4.17, 5.83, 6.28, 7.96, 8.35, 11.35, 11.66, 12.57, 14.34, 14.89, 15.95, 16.74, 17.49, 18.9, 21.1, 23.86, 25.3, 27.04, 27.44, and 30.13+/−0.2. In other preferred embodiments, the substantially pure crystal Form V has two or more of the XRPD peaks identified above. In further embodiments, the crystal form has three or more of the XRPD peaks identified above. In yet further embodiments, the crystal form has four or more of the XRPD peaks identified above.

In one embodiment, the substantially pure crystalline Form V of (1R,2R)-7-chloro-3-[2-(2,4-difluorophenyl)-2-hydroxy-1-methyl-3-(1H-1,2,4-triazol-1-yl)propyl]quinazolin-4(3H)-one has an infrared spectra pattern that may contain at least one spectral line position selected from the group consisting of those at 1723.8, 1676.0, 1599.0, 1557.5, 1499.4, 1462.2, 1402.4, 1318.0, 1272.4, 1253.7, 1169.9, 1138.0, 1102.7, 1061.4, 967.2, 932.8, 902.0, 857.4, 801.2, 785.9, 693.9, 677.2, 665.1, 631.8, and 533.4 cm$^{-1}$.

In another embodiment, the substantially pure crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one has a characteristic X-ray powder diffraction (XRPD) pattern that may contain at least one 2-theta position selected from the group consisting of those at about 10.1, 12.1, 13.3, 14.5, 15.0, 16.0, 16.6, 17.0, 17.4, 18.8, 19.2, 19.7, 21.1, 22.3, 23.9, 24.2, 24.8, 25.7, 26.7, 27.6, 28.6, 28.9, 29.3, 29.7, 30.0, 30.5, 30.8, 31.3, 33.3, 33.7, 34.3, 35.0, 35.5, 36.5, 36.7, 37.4, and 39.5+/−0.2. In other preferred embodiments, the substantially pure crystal Form VI has two or more of the XRPD peaks identified above. In further embodiments, the crystal form has three or more of the XRPD peaks identified above.

In a preferred embodiment, the substantially pure crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one has a characteristic X-ray powder diffraction (XRPD) pattern that may contain at least one 2-theta position selected from the group consisting of those at about 10.1, 14.5, 16.0, 21.1, 24.8, and 25.7+/−0.2. In a further preferred embodiment, the substantially pure crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one has a characteristic X-ray powder diffraction (XRPD) pattern selected from the group consisting of (F1) 2-theta positions at about 10.1, 14.5, 16.0, 21.1, 24.8, and 25.7+/−0.2; (F2) 2-theta positions at about 14.5, 16.0, 21.1, 24.8, and 25.7+/−0.2; (F3) 2-theta positions at about 21.1, 24.8, and 25.7+/−0.2; and (F4) a 2-theta position at about 10.1+/−0.2.

In one embodiment, the substantially pure crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one has an infrared spectra pattern that may contain at least one spectral line position selected from the group consisting of those at 1607, 1555, 1468, 1400, 1361, 1316, 1280, 1218, 1165, 1102, 1014, 976, 938, 760, and 698 cm$^{-1}$.

In other preferred embodiments, the crystal form has two or more of the XRPD peaks identified in any one of the embodiments disclosed herein. In further embodiments, the crystal form has three or more of the XRPD peaks identified in any one of the embodiments disclosed herein. In yet further embodiments, the crystal form has four or more of the XRPD peaks identified in any one of the embodiments disclosed herein.

In another embodiment, the substantially pure crystalline form of (1R,2R)-7-chloro-3-[2-(2,4-difluorophenyl)-2-hydroxy-1-methyl-3-(1H-1,2,4-triazol-1-yl)propyl]quinazolin-4(3H)-one is characterized by at least one of the following properties: an X-ray powder diffraction pattern substantially similar to that presented in the figure selected from the group consisting of FIG. 1, FIG. 4, FIG. 7, FIG. 10, FIG. 13, and FIG. 16; a differential scanning calorimetry thermogram substantially similar to that presented in the figure selected from the group consisting of FIG. 3, FIG. 6, FIG. 9, FIG. 12, FIG. 15, FIG. 18a, FIG. 18b, and FIG. 18c; or an infrared spectra substantially similar to that presented in the figure selected from the group consisting of FIGS. 17a, 17b, 17c, and 17d.

In a preferred embodiment, the substantially pure crystalline form of (1R,2R)-7-chloro-3-[2-(2,4-difluorophenyl)-2-hydroxy-1-methyl-3-(1H-1,2,4-triazol-1-yl)propyl]quinazolin-4(3H)-one is characterized by at least one of the following properties: a differential scanning calorimetry thermogram exhibiting a large endotherm at about 102° C., and having an onset temperature at about 87° C.; or an infrared spectra having characteristic infrared spectral peak positions at 1607, 1555, 1468, 1400, 1361, 1316, 1280, 1218, 1165, 1102, 1014, 976, 938, 760, and 698 cm$^{-1}$. In one preferred embodiment, the substantially pure crystalline form is characterized as having an infrared spectra having at least two of the characteristic infrared spectral peak positions at 1607, 1555, 1468, 1400, 1361, 1316, 1280, 1218, 1165, 1102, 1014, 976, 938, 760, and 698 cm$^{-1}$. In another preferred embodiment, the substantially pure crystalline form is characterized as having an infrared spectra having at least three of the characteristic infrared spectral peak positions. In yet another preferred embodiment, the substantially pure crystalline form is characterized as having an infrared spectra having at least four of the characteristic infrared spectral peak positions.

In a particularly preferred embodiment, the present subject matter contemplates the substantially pure crystalline Form VI, wherein the crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one has characteristic X-ray powder diffraction (XRPD) 2-theta positions at about 21.1, 24.8, and 25.7+/−0.2. In another preferred embodiment, the present subject matter contemplates the substantially pure crystalline Form VI, wherein the crystalline Form VI of (1R, 2R)-7-chloro-3-[2-(2,4-difluorophenyl)-2-hydroxy-1-methyl-3-(1H-1,2,4-triazol-1-yl)propyl]quinazolin-4(3H)-one has characteristic X-ray powder diffraction (XRPD) 2-theta positions at about 14.5, 16.0, 21.1, 24.8, and 25.7+/−0.2. In a further preferred embodiment, the present subject matter contemplates the substantially pure crystalline Form VI, wherein the crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one has characteristic X-ray powder diffraction (XRPD) 2-theta positions at about 10.1, 14.5, 16.0, 21.1, 24.8, and 25.7+/−0.2. In a further preferred embodiment, the present subject matter contemplates the substantially pure crystalline Form VI, wherein the crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one has characteristic X-ray powder diffraction (XRPD) 2-theta position at about 10.1+/−0.2.

Figure 16:
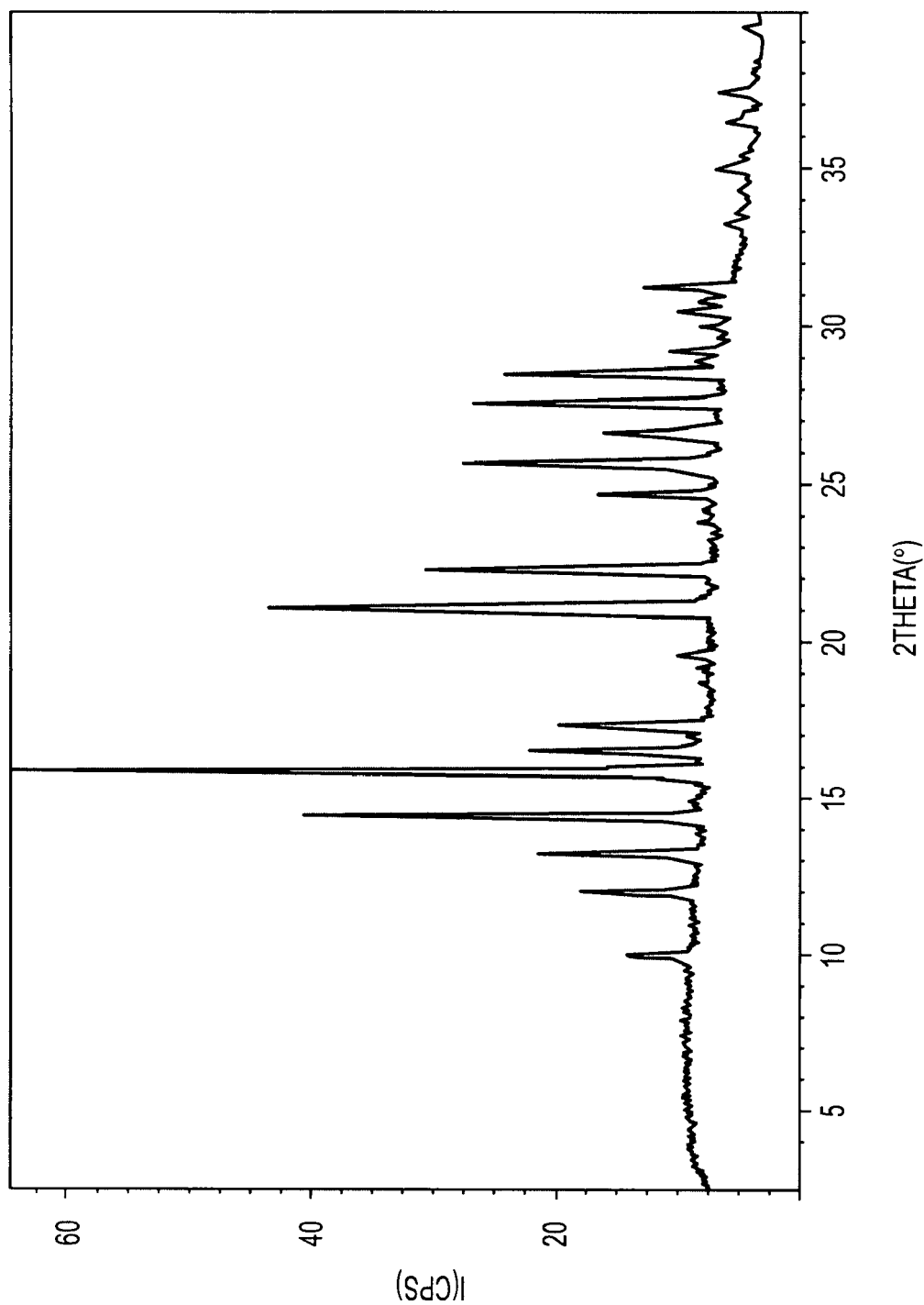
FIG. 16 presents a characteristic XRPD pattern of the crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one.
Figure 17B:
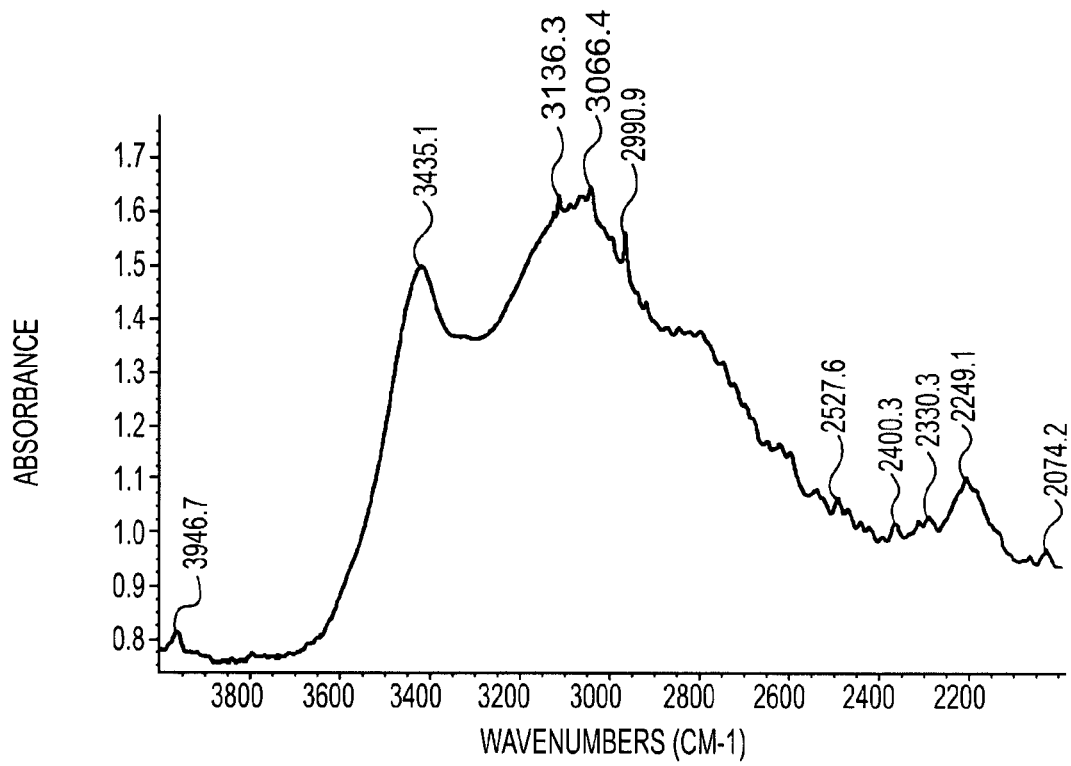
FIGS. 17a-c present a characteristic IR spectrum of the crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one. The complete IR Spectrum of FIG. 17a is displayed in higher resolution in FIGS. 17b, 17c, and 17d to show characteristic peaks.
Figure 17C:
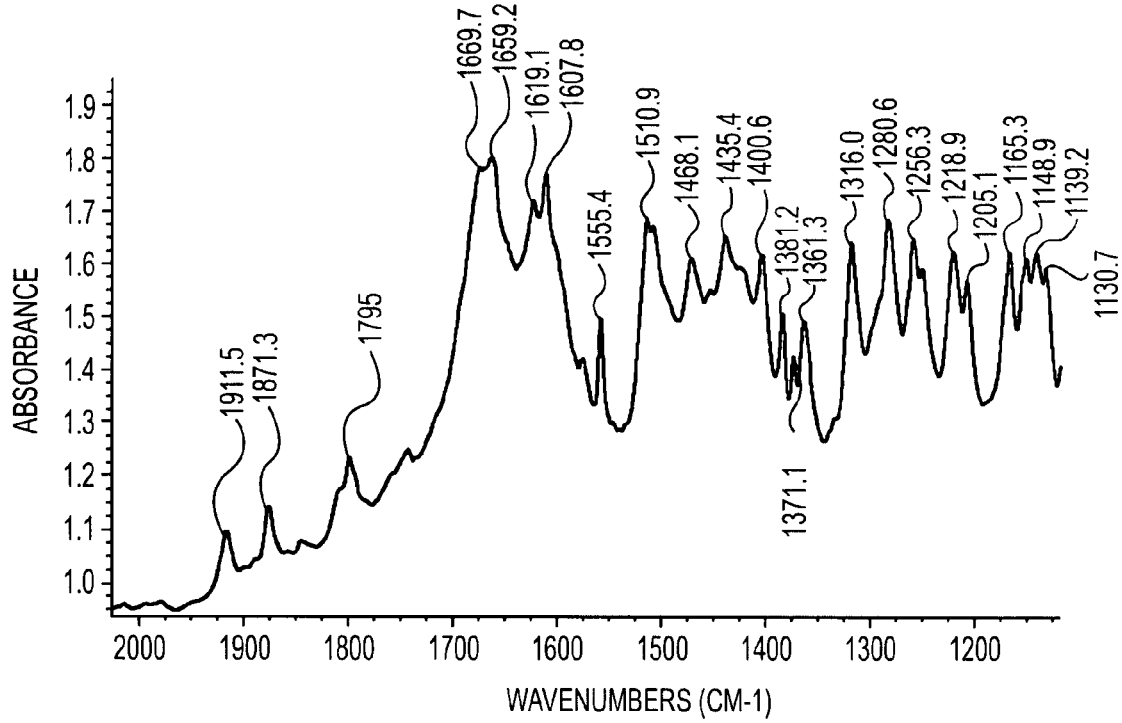
Figure 17D:
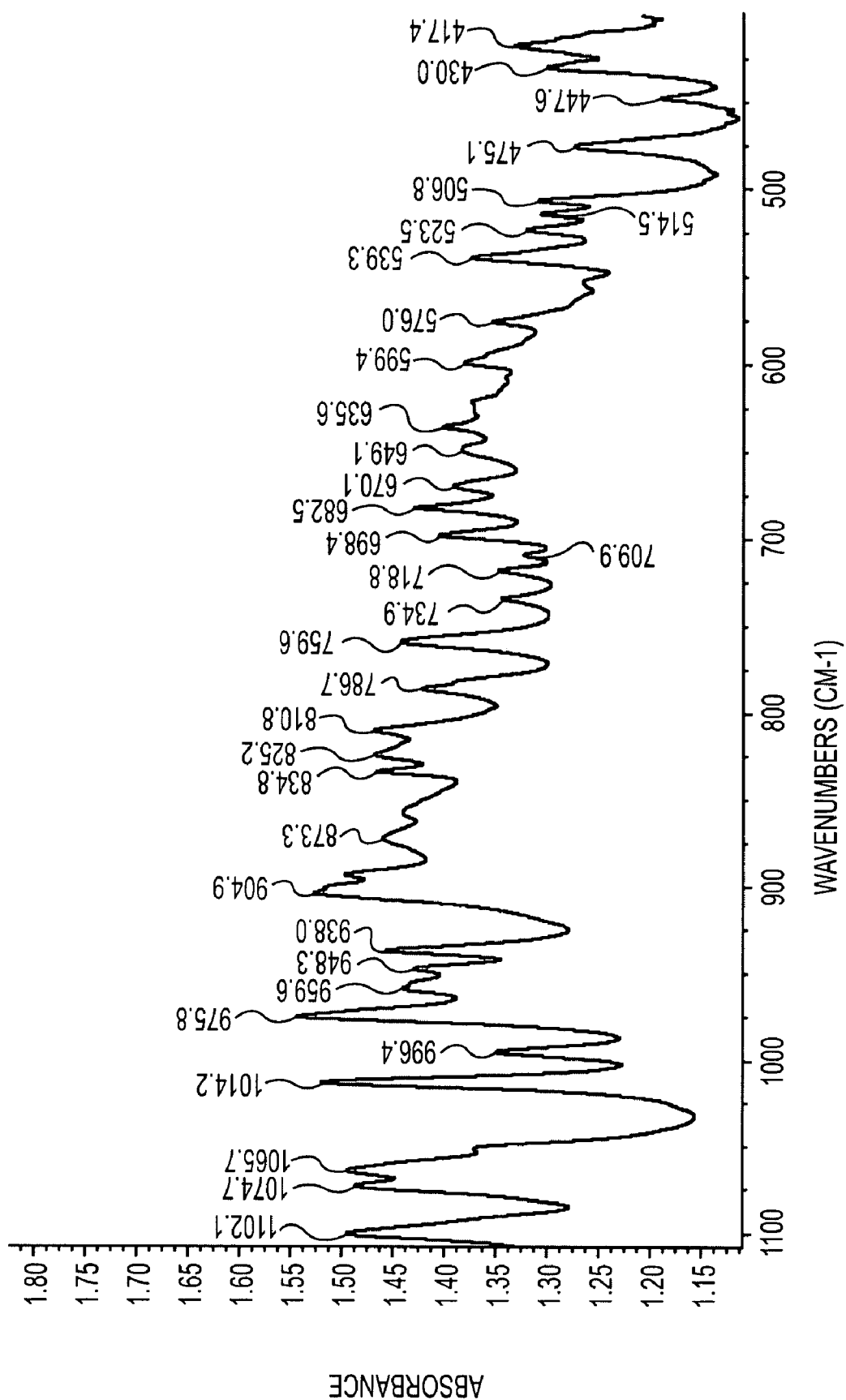
Figure 18A:
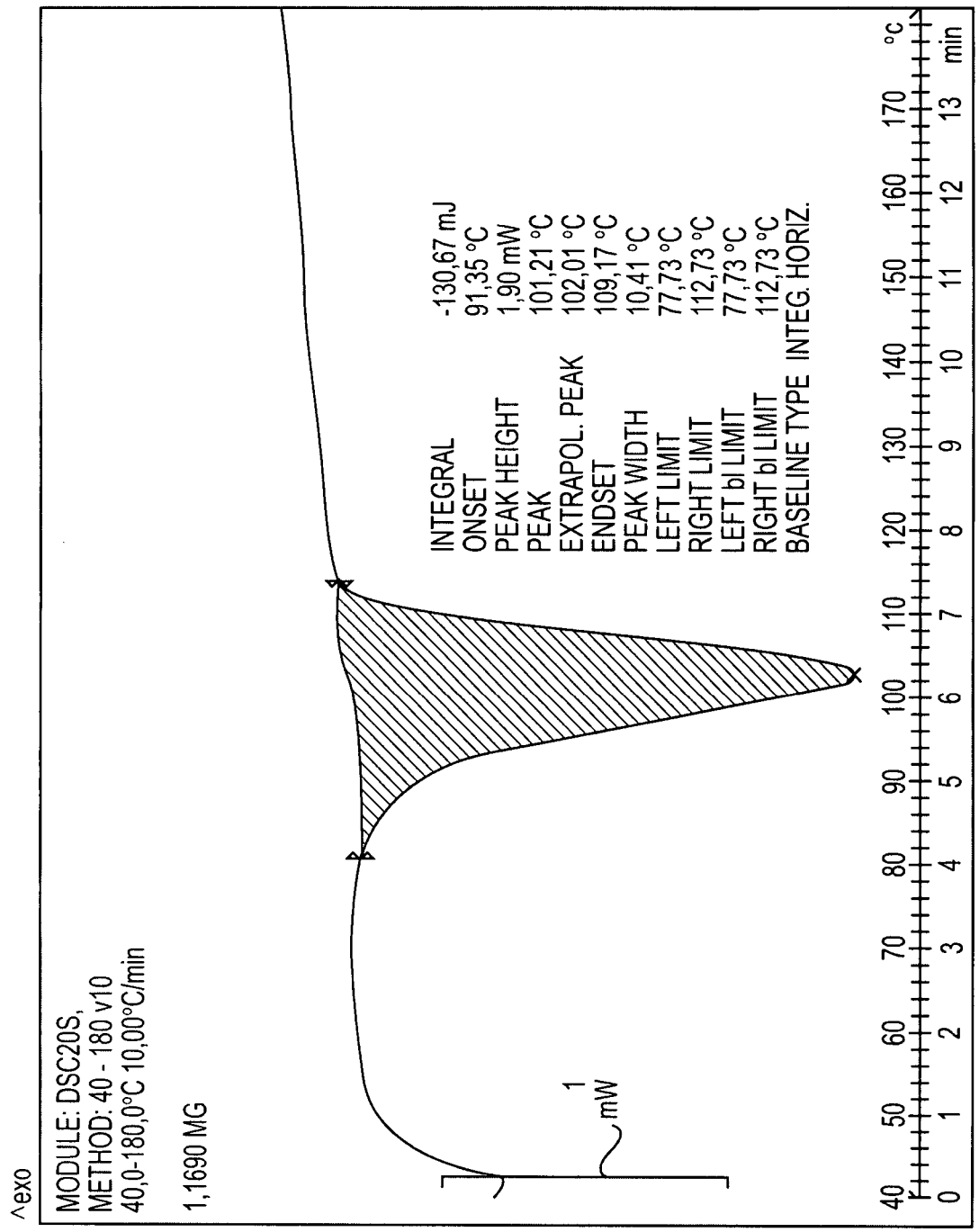
FIGS. 18a-c present three characteristic DSC thermograms of the crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one.
Figure 18B:
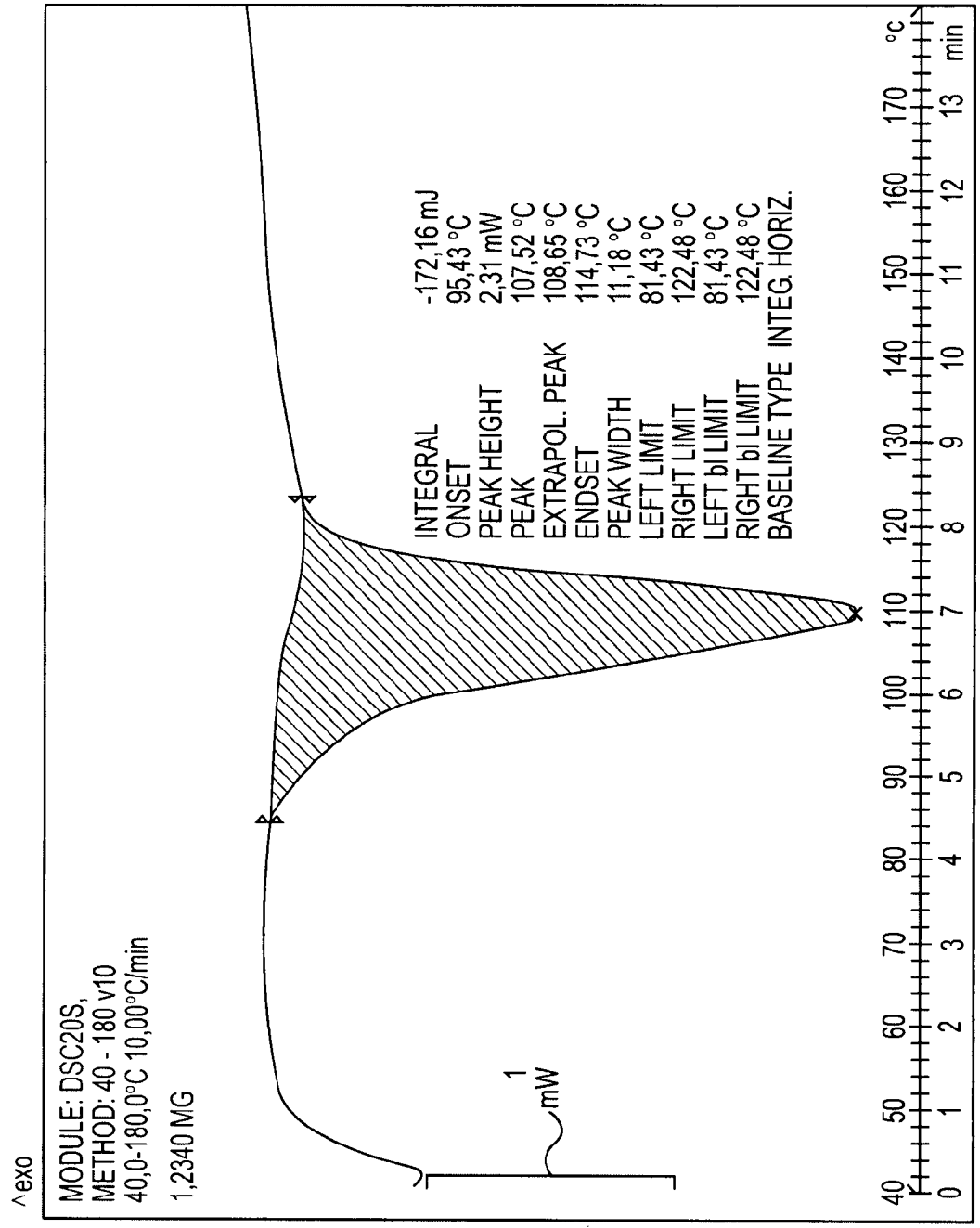
Figure 18C:
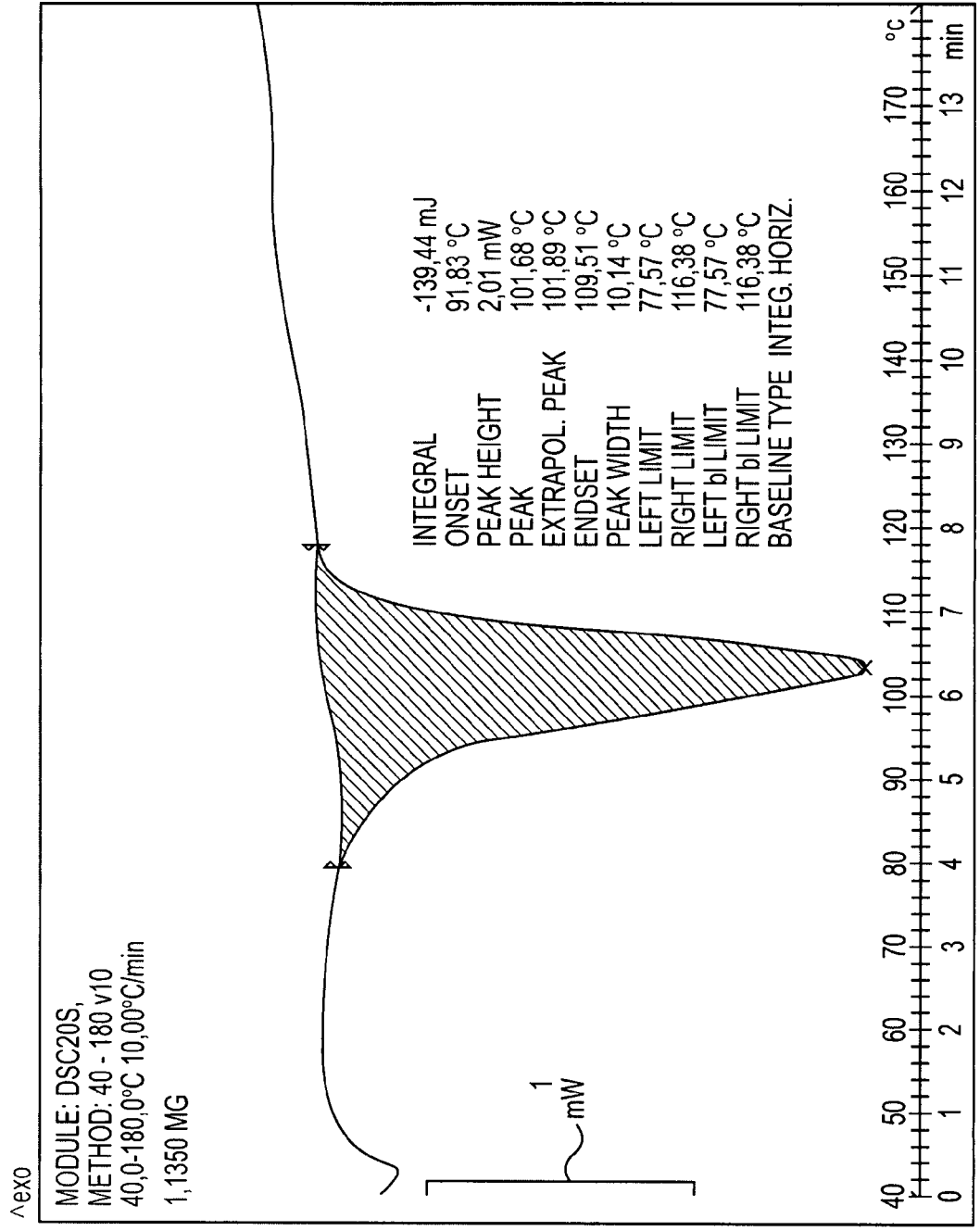

In a particularly preferred embodiment, the present subject matter contemplates the substantially pure crystalline Form VI, wherein the crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one is characterized by at least one of the following properties: an X-ray powder diffraction pattern substantially similar to that presented in FIG. 16; a differential scanning calorimetry thermogram substantially similar to that presented in FIG. 18a, FIG. 18b, or FIG. 18c; or an infrared spectra substantially similar to that presented in FIG. 17a, 17b, or 17c.

In a preferred embodiment, the present subject matter contemplates the substantially pure crystalline Form VI, wherein the crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one is characterized by a differential scanning calorimetry thermogram exhibiting a large endotherm at a temperature ranging from about 102° C. to 108° C. due to the melt. In a particularly preferred embodiment, the present subject matter contemplates the substantially pure crystalline Form VI, wherein the crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one is characterized by a differential scanning calorimetry thermogram exhibiting a large endotherm at about 102° C. due to the melt, and wherein the onset temperature is at about 87° C.

In a particularly preferred embodiment, the present subject matter contemplates the substantially pure crystalline Form VI, wherein the crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one has characteristic Fourier transform infrared spectral peak positions at 1607, 1555, 1468, 1400, 1361, 1316, 1280, 1218, 1165, 1102, 1014, 976, 938, 760, and 698 $cm^{-1}$.

Additionally, the present subject matter contemplates substantially pure crystalline forms of (1R,2R)-7-chloro-3-[2-(2,4-difluorophenyl)-2-hydroxy-1-methyl-3-(1H-1,2,4-triazol-1-yl)propyl]quinazolin-4(3H)-one substantially devoid of degradation products of the (1R,2R)-7-chloro-3-[2-(2,4-difluorophenyl)-2-hydroxy-1-methyl-3-(1H-1,2,4-triazol-1-yl)propyl]quinazolin-4(3H)-one. In this regard, the present subject matter further contemplates a substantially pure crystalline Form I, II, III, IV, V, or VI of (1R,2R)-7-chloro-3-[2-(2,4-difluorophenyl)-2-hydroxy-1-methyl-3-(1H-1,2,4-triazol-1-yl)propyl]quinazolin-4(3H)-one having not less than 97% purity with respect to other forms of the compound or any degradation products.

Physical Characteristics

The six crystalline forms of (1R,2R)-7-chloro-3-[2-(2,4-difluorophenyl)-2-hydroxy-1-methyl-3-(1H-1,2,4-triazol-1-yl)propyl]quinazolin-4(3H)-one designated as Form I, II, III, IV, V, and VI can readily be distinguished from one another by examination of their respective characteristic x-ray diffraction (XRPD) patterns (see FIGS. 1, 4, 7, 10, 13, and 16, respectively), characteristic IR spectra (see FIGS. 2, 5, 8, 11, 14, and 17a-c, respectively), or differential scanning calorimetry (DSC) thermograms (see FIGS. 3, 6, 9, 12, 15, and 18a-c, respectively). Form VI can also be characterized by its physical structure and atomic bond orientation (see FIG. 19) and by packing diagrams of Form VI along the a, b, and c, crystallographic axes (see FIGS. 20, 21, 22, and 23).

Form I

Crystalline Form I of (1R,2R)-7-chloro-3-[2-(2,4-difluorophenyl)-2-hydroxy-1-methyl-3-(1H-1,2,4-triazol-1-yl)propyl]quinazolin-4(3H)-one was in part identified by its characteristic XRPD pattern. The XRPD pattern for Form I was measured on a D5000 Siemens X-ray diffractometer, having a graphite secondary monochromator and a scintillation detector. The anode was of copper (wavelength CuKα: 1.541838 Å, V=50 kV, I=20 mA) and the ambient temperature was kept at 21° C.

A characteristic XRPD pattern distinctive to Form I was observed, as represented by FIG. 1. The characteristic 2-theta positions and corresponding intensities observed for this specific pattern are summarized below in Table 1.

TABLE 1

Characteristic XRPD 2-Theta Positions and Intensities for Form I

| Characteristic XRPD 2-theta positions (+/−0.2) | Characteristic XRPD Intensities (counts) |
| --- | --- |
| 4.11 | 115 |
| 8.22 | 128 |
| 9.39 | 66 |
| 11.29 | 161 |
| 12.41 | 102 |
| 13.21 | 95 |
| 13.62 | 160 |
| 14.43 | 206 |
| 14.93 | 231 |
| 15.7 | 104 |
| 16.74 | 215 |
| 17.3 | 134 |
| 17.57 | 178 |
| 18.79 | 296 |
| 20.88 | 151 |
| 21.88 | 125 |
| 22.62 | 98 |
| 23.64 | 119 |
| 23.82 | 177 |
| 25.2 | 234 |
| 26.77 | 206 |
| 27.21 | 245 |
| 28.57 | 116 |
| 29.16 | 113 |
| 29.97 | 110 |
| 30.75 | 81 |
| 31.35 | 93 |
| 45.28 | 56 |
| 48.87 | 42 |
| 55.02 | 36 |

The most relevant 2-theta positions and corresponding intensities observed for this specific XRPD pattern for Form I are summarized below in Table 2.

TABLE 2

Most Relevant XRPD 2-Theta Positions and Intensities for Form I

| Characteristic XRPD 2-theta positions (+/−0.2) | Characteristic XRPD Intensities (counts) |
| --- | --- |
| 4.11 | 115 |
| 8.22 | 128 |
| 9.39 | 66 |
| 11.29 | 161 |
| 12.41 | 102 |
| 13.62 | 160 |
| 16.74 | 215 |
| 17.57 | 178 |
| 18.79 | 296 |
| 23.82 | 177 |
| 25.2 | 234 |

A set of XRPD peaks that uniquely characterizes Form I has 2-theta positions at about 4.11, 8.22, 9.39, 11.29, 12.41, 13.62, 16.74, 17.57, 18.79, 23.82, and 25.2+/−0.2.

Figure 2:
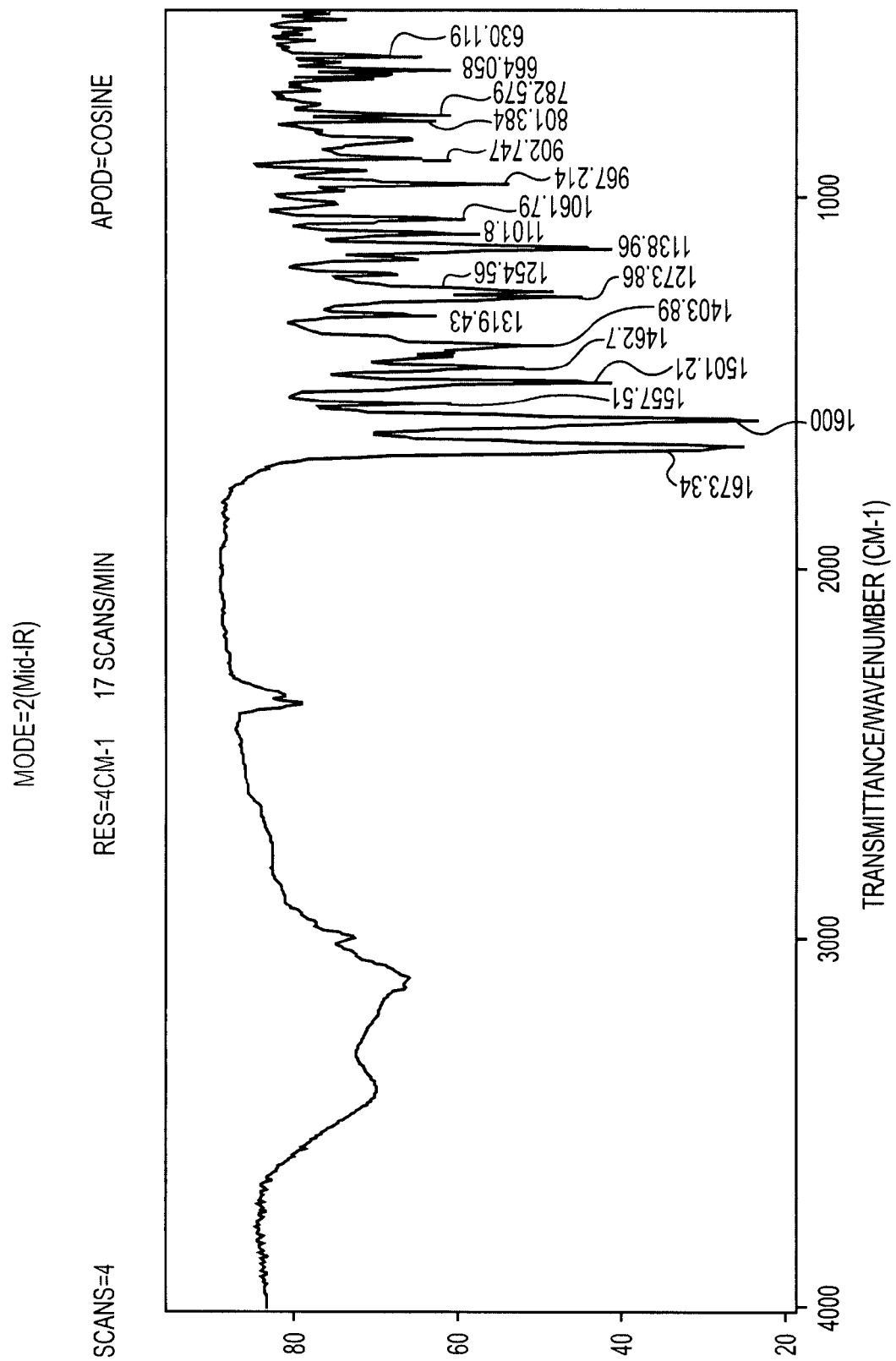
FIG. 2 presents a characteristic infrared (IR) spectrum of the crystalline Form I of (1R,2R)-7-chloro-3-[2-(2,4-difluorophenyl)-2-hydroxy-1-methyl-3-(1H-1,2,4-triazol-1-yl)propyl]quinazolin-4(3H)-one.

The complete infrared (IR) spectrum of the crystalline Form I is shown in FIG. 2 and is characterized as summarized below in Table 3. All IR spectrum analyses obtained and discussed herein were generated on a Bomem BM-100 spectrophotometer, unless otherwise specified.

TABLE 3

Infrared Spectrum for Form I
Frequency (cm$^{-1}$) (+/−0.1)

| |
|---|
| 1673.3 |
| 1600.0 |
| 1557.5 |
| 1501.2 |
| 1462.7 |
| 1403.9 |
| 1319.4 |
| 1273.9 |
| 1254.6 |
| 1139.0 |
| 1101.8 |
| 1061.8 |
| 967.2 |
| 902.7 |
| 801.3 |
| 783.6 |
| 664.1 |
| 630.1 |

Figure 3:
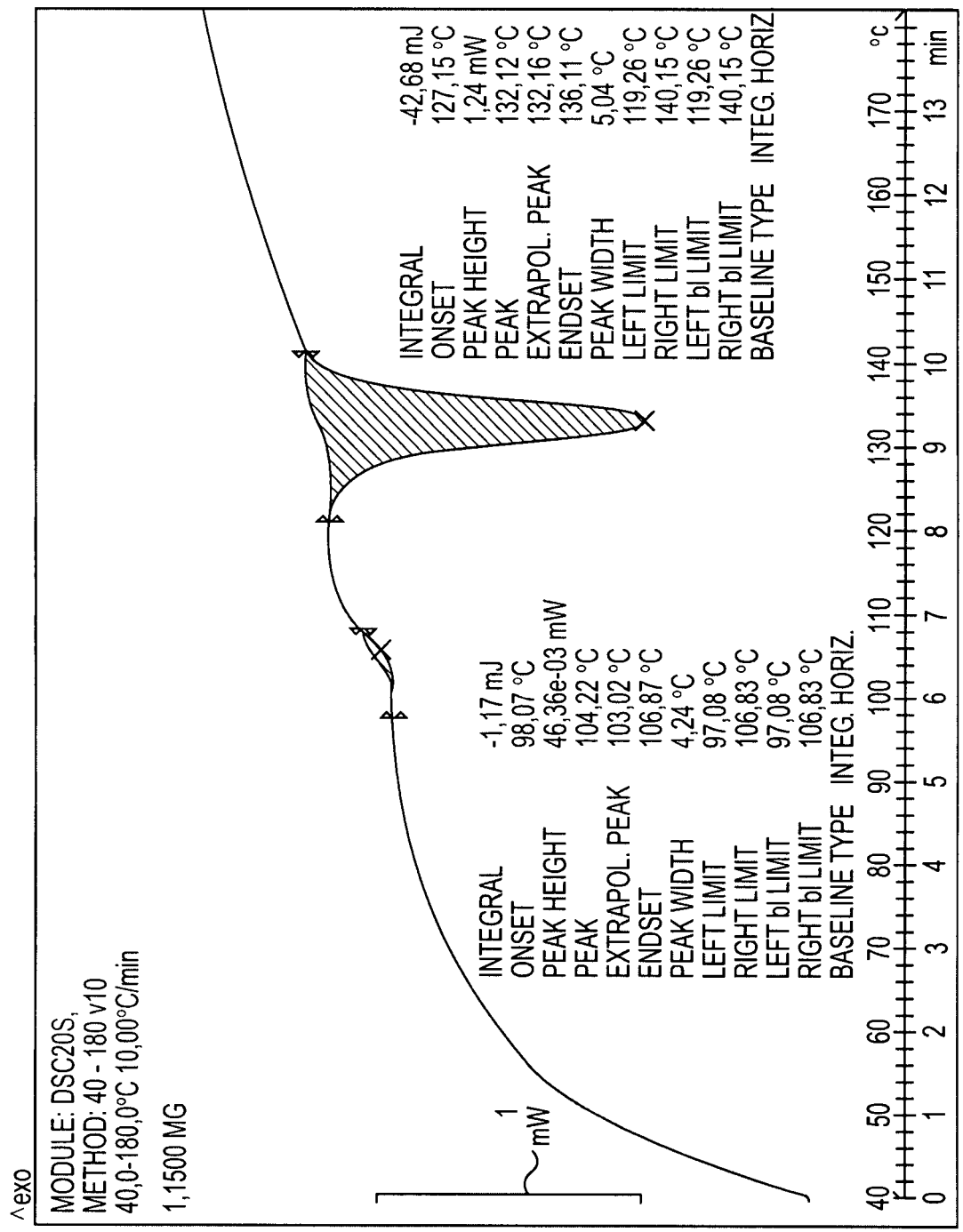
FIG. 3 presents a characteristic differential scanning calorimetry (DSC) thermogram of the crystalline Form I of (1R,2R)-7-chloro-3-[2-(2,4-difluorophenyl)-2-hydroxy-1-methyl-3-(1H-1,2,4-triazol-1-yl)propyl]quinazolin-4(3H)-one.

Form I was further observed to have a characteristic endothermic peak using DSC analysis, as represented by FIG. 3. All DSC analyses obtained herein were measured on a Mettler-Toledo DSC-20 instrument, unless otherwise specified. The samples (each of about 1 mg), were enclosed in aluminium pans having small holes accurately weighted, heated over a temperature range of 40-180° C., at a scan rate of 10°/min, under a nitrogen purge. The apparatus was calibrated with (99.9% pure) indium.

Form II

Crystalline Form II of (1R,2R)-7-chloro-3-[2-(2,4-difluorophenyl)-2-hydroxy-1-methyl-3-(1H-1,2,4-triazol-1-yl) propyl]quinazolin-4(3H)-one was likewise in part identified by its characteristic XRPD pattern. The XRPD pattern for Form II was measured on a D5000 Siemens X-ray diffractometer, having a graphite secondary monochromator and a scintillation detector. The anode was of copper (wavelength CuKα: 1.541838 Å, V=50 kV, I=20 mA) and the ambient temperature was kept at 21° C.

Figure 4:
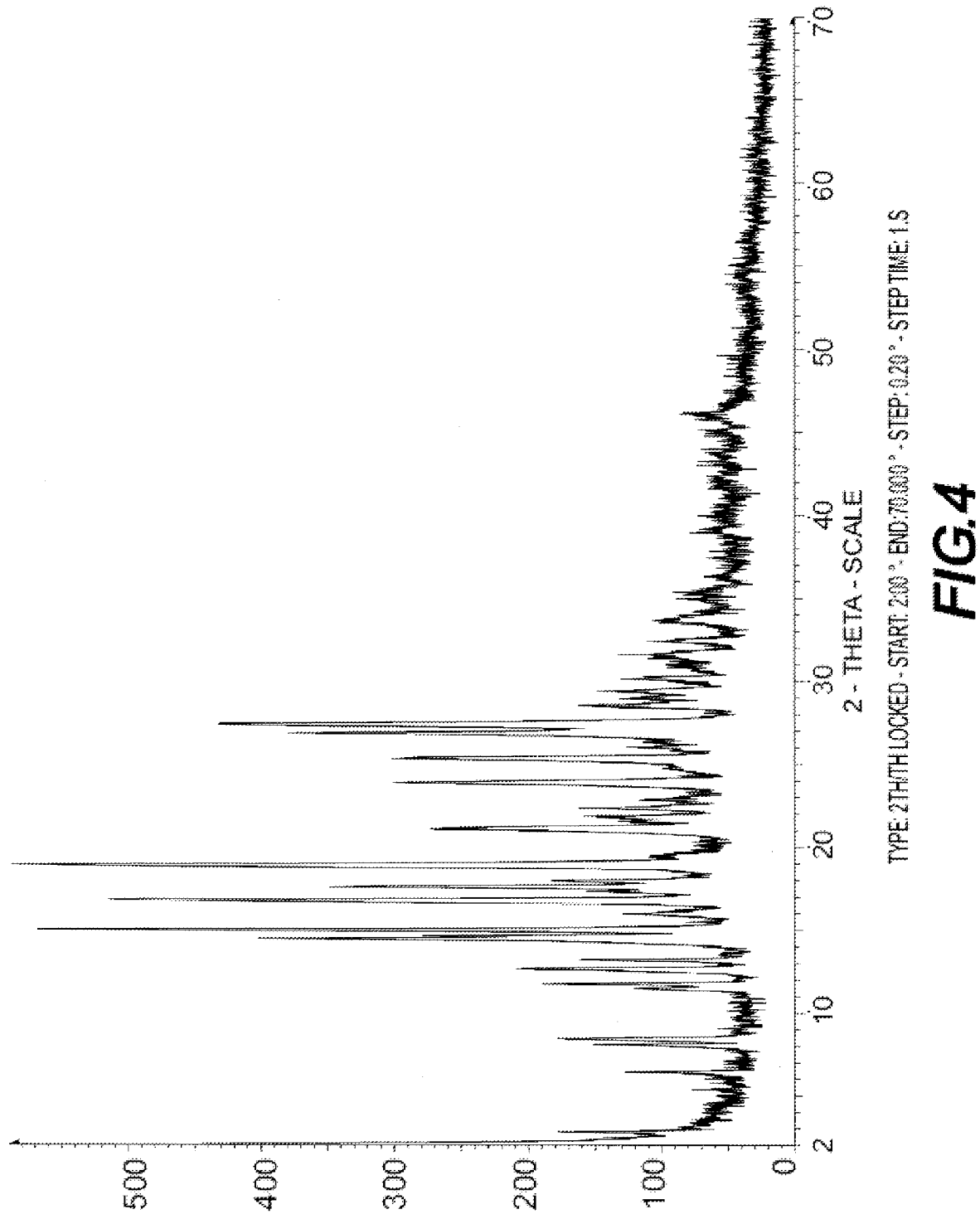
FIG. 4 presents a characteristic XRPD pattern of the crystalline Form II of (1R,2R)-7-chloro-3-[2-(2,4-difluorophenyl)-2-hydroxy-1-methyl-3-(1H-1,2,4-triazol-1-yl)propyl]quinazolin-4(3H)-one.

A characteristic XRPD pattern distinctive to Form II was observed, as represented by FIG. 4. The characteristic 2-theta positions and corresponding intensities observed for this specific pattern are summarized below in Table 4.

TABLE 4

Characteristic XRPD 2-Theta Positions and Intensities for Form II

| Characteristic XRPD 2-theta positions (+/−0.2) | Characteristic XRPD Intensities (counts) |
|---|---|
| 2.72 | 176 |
| 5.31 | 62 |
| 6.35 | 126 |
| 7.98 | 124 |
| 8.37 | 177 |
| 9.01 | 56 |
| 11.4 | 112 |
| 11.7 | 188 |
| 12.6 | 208 |
| 13.15 | 160 |
| 14.42 | 402 |
| 14.98 | 568 |
| 15.93 | 128 |
| 16.77 | 511 |
| 17.56 | 348 |
| 17.91 | 181 |
| 18.86 | 589 |
| 19.37 | 108 |
| 21.08 | 272 |
| 21.78 | 147 |
| 22.31 | 161 |
| 22.82 | 115 |
| 23.84 | 300 |
| 25.32 | 294 |
| 26 | 125 |
| 26.83 | 379 |
| 27.35 | 432 |
| 28.5 | 161 |
| 28.96 | 122 |
| 29.38 | 147 |
| 30.14 | 120 |
| 31.58 | 131 |
| 32.41 | 109 |
| 33.63 | 105 |
| 34.94 | 77 |
| 46.1 | 85 |

The most relevant 2-theta positions and corresponding intensities observed for this specific XRPD pattern for Form II are summarized below in Table 5.

TABLE 5

Most Relevant XRPD 2-Theta Positions and Intensities for Form II

| Characteristic XRPD 2-theta positions (+/−0.2) | Characteristic XRPD Intensities (counts) |
|---|---|
| 6.35 | 126 |
| 7.98 | 124 |
| 8.37 | 177 |
| 11.4 | 112 |
| 11.7 | 188 |
| 12.6 | 208 |
| 13.15 | 160 |
| 14.42 | 402 |
| 14.98 | 568 |
| 16.77 | 511 |
| 17.56 | 348 |
| 18.86 | 589 |
| 21.08 | 272 |
| 23.84 | 300 |
| 25.32 | 294 |
| 26.83 | 379 |
| 27.35 | 432 |

A set of XRPD peaks that uniquely characterizes Form II has 2-theta positions at about 6.35, 7.98, 8.37, 11.4, 11.7, 12.6, 13.15, 14.42, 14.98, 16.77, 17.56, 18.86, 21.08, 23.84, 25.32, 26.83, and 27.35+/−0.2.

Figure 5:
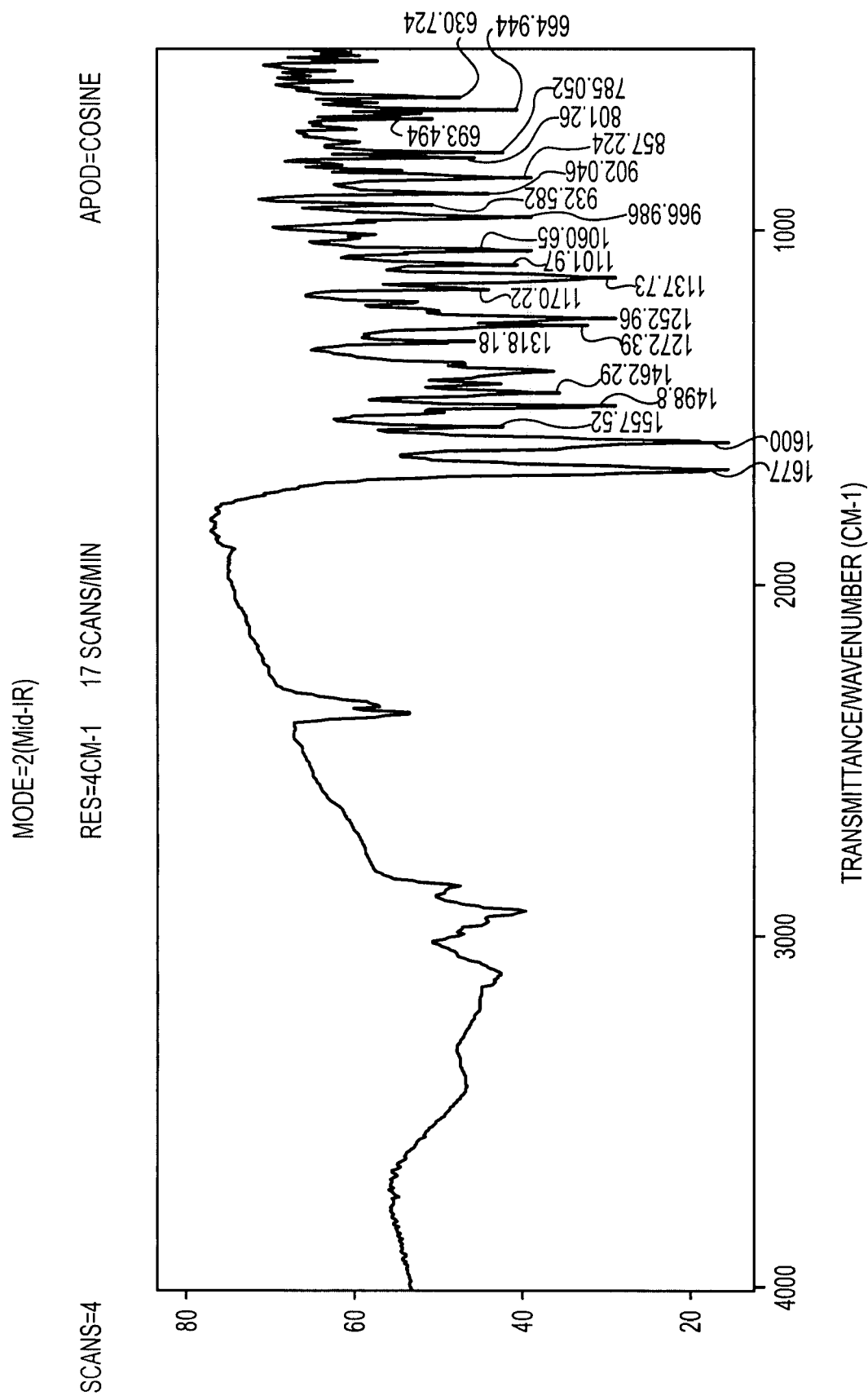
FIG. 5 presents a characteristic IR spectrum of the crystalline Form II of (1R,2R)-7-chloro-3-[2-(2,4-difluorophenyl)-2-hydroxy-1-methyl-3-(1H-1,2,4-triazol-1-yl)propyl]quinazolin-4(3H)-one.

The complete infrared spectrum of the crystalline Form II is shown in FIG. 5 and is characterized as summarized below in Table 6.

TABLE 6

Infrared Spectrum for Form II
Frequency (cm$^{-1}$) (+/−0.1)

| |
|---|
| 1677.0 |
| 1600.0 |
| 1557.5 |
| 1498.8 |
| 1462.3 |
| 1318.2 |

TABLE 6-continued

Infrared Spectrum for Form II
Frequency (cm$^{-1}$) (+/−0.1)

| |
|---|
| 1272.4 |
| 1253.0 |
| 1170.2 |
| 1137.7 |
| 1102.0 |
| 1060.7 |
| 967.0 |
| 932.6 |
| 902.0 |
| 857.2 |
| 801.3 |
| 785.1 |
| 693.5 |
| 664.9 |
| 630.7 |

Figure 6:
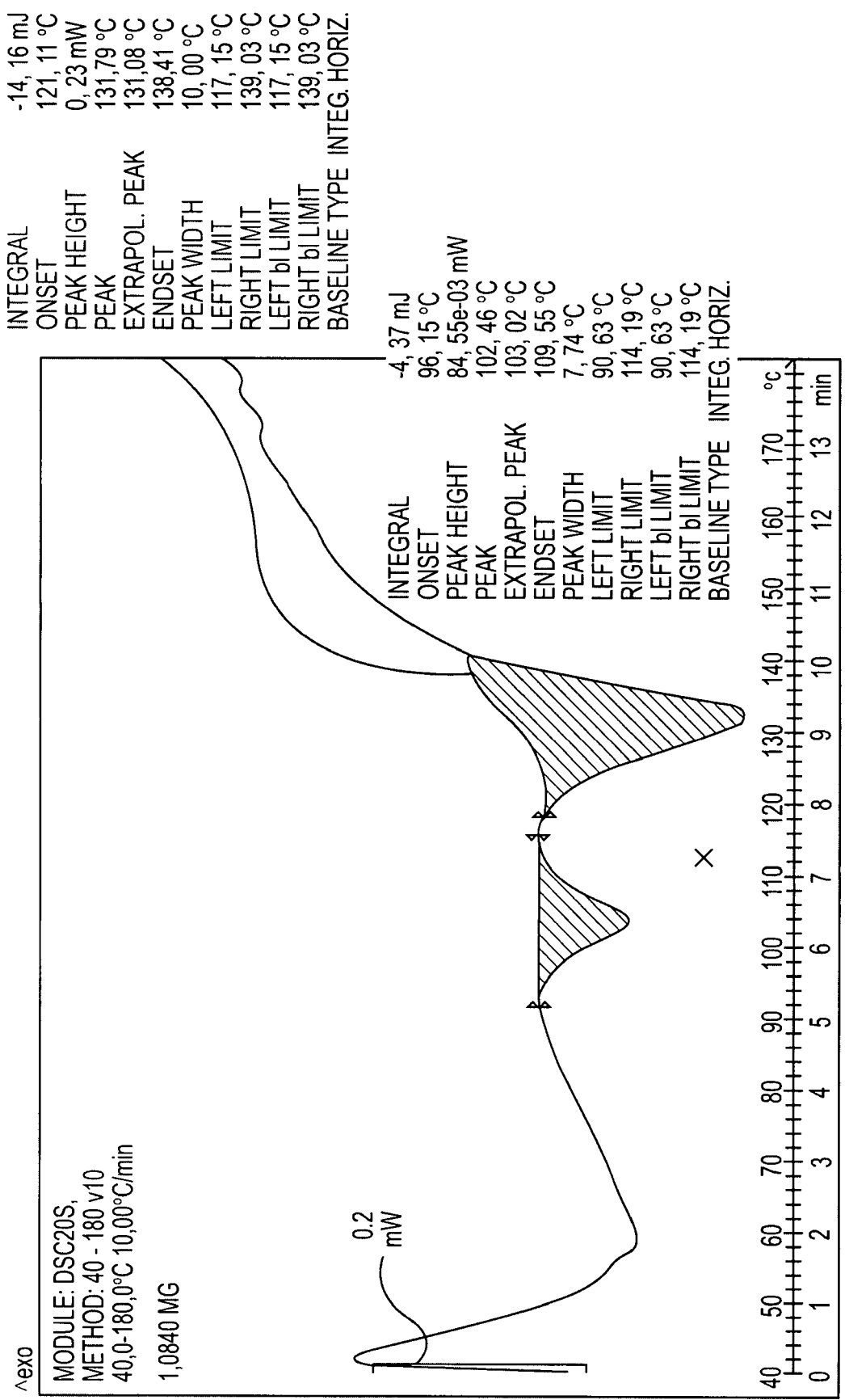
FIG. 6 presents a characteristic DSC thermogram of the crystalline Form II of (1R,2R)-7-chloro-3-[2-(2,4-difluorophenyl)-2-hydroxy-1-methyl-3-(1H-1,2,4-triazol-1-yl)propyl]quinazolin-4(3H)-one.

Form II was further observed to have a characteristic endothermic peak using DSC analysis, as represented by FIG. 6.

Form III

Crystalline Form III of (1R,2R)-7-chloro-3-[2-(2,4-difluorophenyl)-2-hydroxy-1-methyl-3-(1H-1,2,4-triazol-1-yl)propyl]quinazolin-4(3H)-one was in part identified by its characteristic XRPD pattern. The XRPD pattern for Form III was measured at room temperature using a Philips X'Pert diffractometer equipped with a θ/2θ goniometer, a Cu tube working at 50 kV and 40 mA (CuKα radiation, λ=1.5419 Å), a divergence slit=1/4°, Soller slits=0.04 rad, an anti-scatter slit=1/4°, a receiving slit=0.10 mm, and a secondary curved graphite monochromator. Data were collected in the range 2-35° of 2theta using a step-scan technique with a step size=0.02° and a time per step=20 s.

Figure 7:
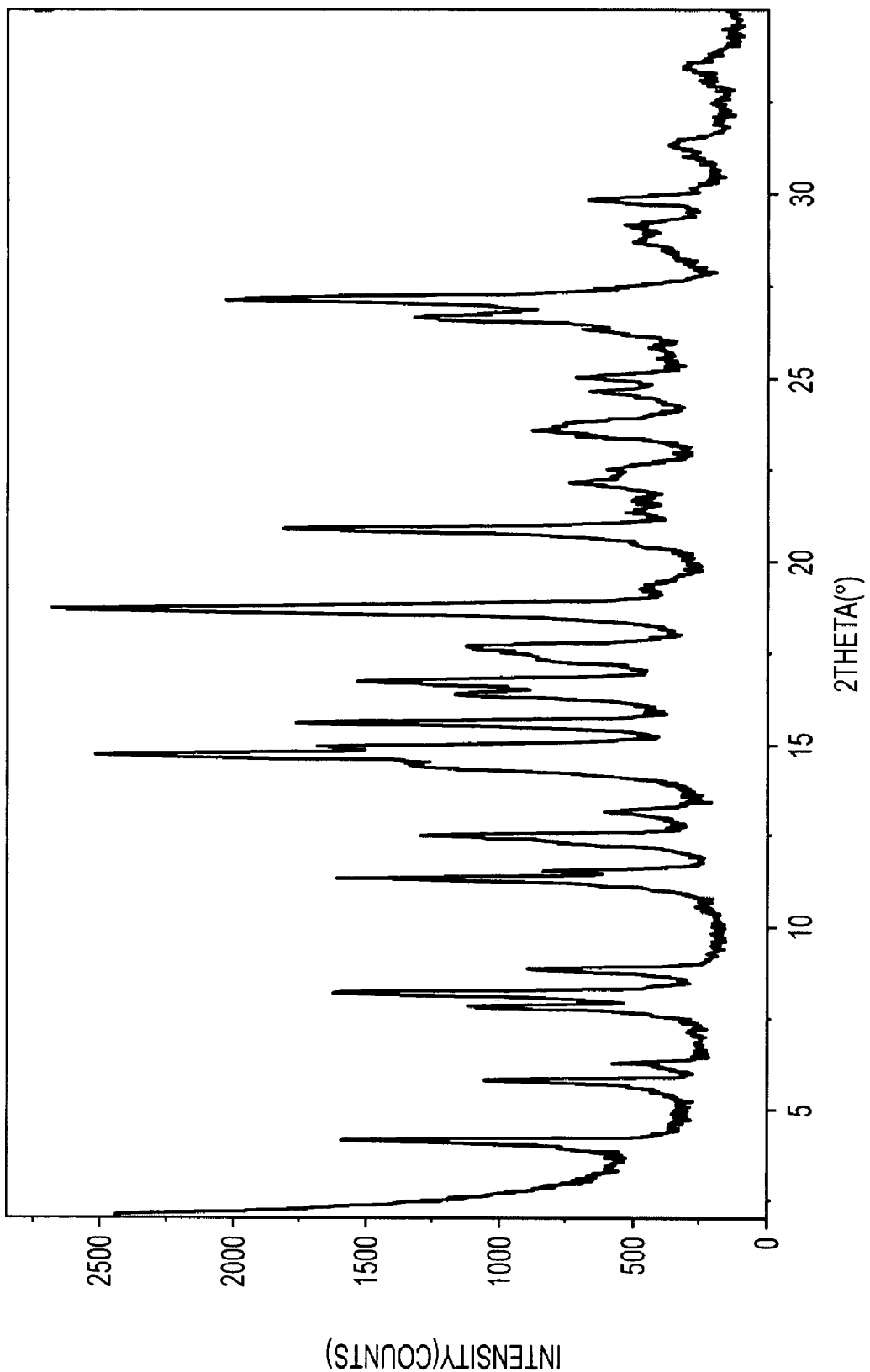
FIG. 7 presents a characteristic XRPD pattern of the crystalline Form III of (1R,2R)-7-chloro-3-[2-(2,4-difluorophenyl)-2-hydroxy-1-methyl-3-(1H-1,2,4-triazol-1-yl)propyl]quinazolin-4(3H)-one.

A characteristic XRPD pattern distinctive to Form III was observed, as represented by FIG. 7. The characteristic 2-theta positions and corresponding intensities observed for this specific pattern are summarized below in Table 7.

TABLE 7

Characteristic XRPD 2-Theta Positions and Intensities for Form III

| Characteristic XRPD 2-theta positions (+/−0.2) | Characteristic XRPD Relative Intensity (%) |
|---|---|
| 4.08 | 51 |
| 5.73 | 34 |
| 6.22 | 13 |
| 7.77 | 36 |
| 8.15 | 60 |
| 8.80 | 30 |
| 11.25 | 61 |
| 11.47 | 29 |
| 12.44 | 48 |
| 13.09 | 17 |
| 14.33 | 46 |
| 14.68 | 98 |
| 14.89 | 60 |
| 15.57 | 68 |
| 16.35 | 43 |
| 16.68 | 58 |
| 17.27 | 29 |
| 17.63 | 40 |
| 18.66 | 100 |
| 19.32 | 12 |
| 20.85 | 71 |
| 22.12 | 25 |
| 22.49 | 18 |
| 23.58 | 29 |

TABLE 7-continued

Characteristic XRPD 2-Theta Positions and Intensities for Form III

| Characteristic XRPD 2-theta positions (+/−0.2) | Characteristic XRPD Relative Intensity (%) |
|---|---|
| 24.63 | 20 |
| 25.02 | 24 |
| 26.65 | 48 |
| 27.12 | 77 |
| 28.74 | 15 |
| 29.11 | 17 |
| 29.81 | 23 |
| 31.35 | 10 |
| 33.48 | 8 |

The most relevant 2-theta positions and corresponding intensities observed for this specific XRPD pattern for Form III are summarized below in Table 8.

TABLE 8

Most Relevant XRPD 2-Theta Positions and Intensities for Form III

| Characteristic XRPD 2-theta positions (+/−0.2) | Characteristic XRPD Relative Intensity (%) |
|---|---|
| 4.08 | 51 |
| 5.73 | 34 |
| 6.22 | 13 |
| 7.77 | 36 |
| 8.15 | 60 |
| 8.80 | 30 |
| 11.25 | 61 |
| 11.47 | 29 |
| 12.44 | 48 |
| 13.09 | 17 |
| 15.57 | 68 |
| 17.63 | 40 |
| 18.66 | 100 |
| 20.85 | 71 |
| 26.65 | 48 |
| 27.12 | 77 |

A set of XRPD peaks that uniquely characterizes Form III has 2-theta positions at about 4.08, 5.73, 6.22, 7.77, 8.15, 8.80, 11.25, 11.47, 12.44, 13.09, 15.57, 17.63, 18.66, 20.85, 26.65, and 27.12+/−0.2.

Figure 8:
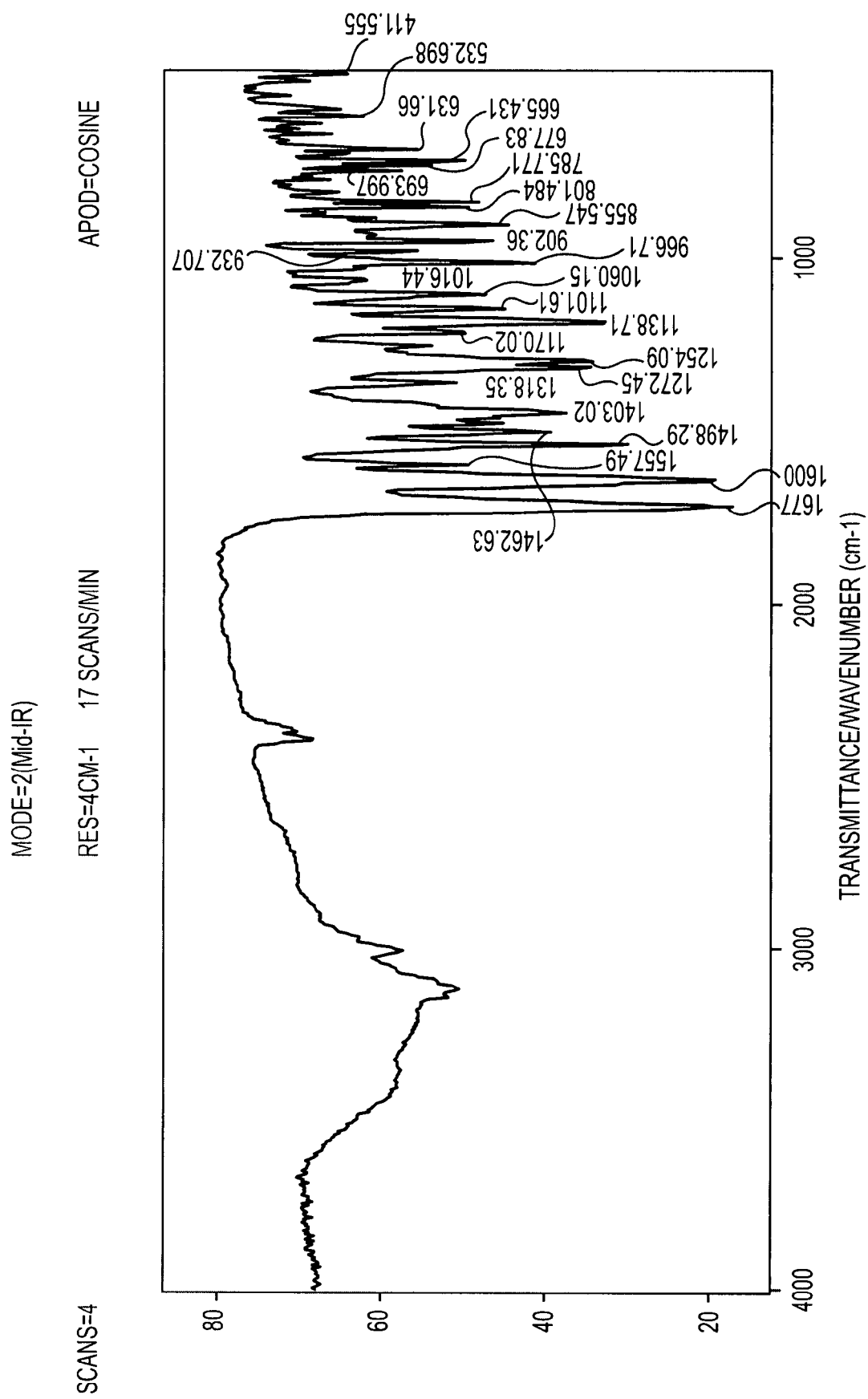
FIG. 8 presents a characteristic IR spectrum of the crystalline Form III of (1R,2R)-7-chloro-3-[2-(2,4-difluorophenyl)-2-hydroxy-1-methyl-3-(1H-1,2,4-triazol-1-yl)propyl]quinazolin-4(3H)-one.

The complete infrared spectrum of the crystalline Form III is shown in FIG. 8 and is characterized as summarized below in Table 9.

TABLE 9

Infrared Spectrum for Form III
Frequency (cm$^{-1}$) (+/−0.1)

| |
|---|
| 1677.0 |
| 1600.0 |
| 1557.5 |
| 1498.3 |
| 1462.6 |
| 1403.0 |
| 1318.4 |
| 1272.5 |
| 1254.1 |
| 1170.0 |
| 1138.7 |
| 1101.6 |
| 1060.2 |
| 1016.4 |
| 966.7 |
| 932.7 |
| 902.4 |
| 855.5 |

TABLE 9-continued

Infrared Spectrum for Form III
Frequency (cm$^{-1}$) (+/−0.1)

801.5
785.8
694.0
677.9
665.4
631.7
532.7
411.6

Figure 9:
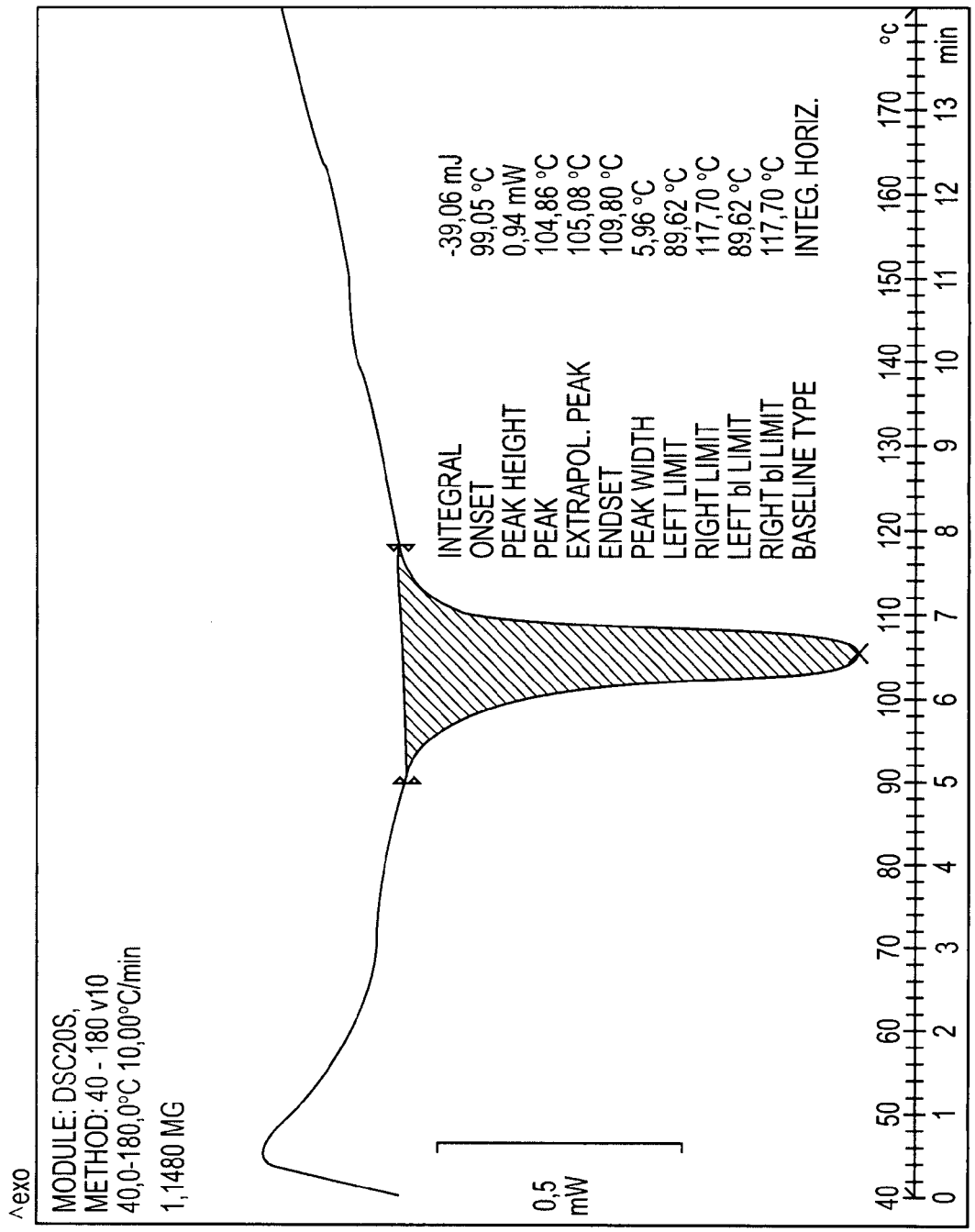
FIG. 9 presents a characteristic DSC thermogram of the crystalline Form III of (1R,2R)-7-chloro-3-[2-(2,4-difluorophenyl)-2-hydroxy-1-methyl-3-(1H-1,2,4-triazol-1-yl)propyl]quinazolin-4(3H)-one.

Form III was further observed to have a characteristic endothermic peak onset observed at about 99+/−5 degrees C. using DSC analysis, as represented by FIG. 9.

Form IV

Crystalline Form IV of (1R,2R)-7-chloro-3-[2-(2,4-difluorophenyl)-2-hydroxy-1-methyl-3-(1H-1,2,4-triazol-1-yl)propyl]quinazolin-4(3H)-one was likewise in part identified by its characteristic XRPD pattern. The XRPD pattern for Form IV was measured at room temperature using a Philips X'Pert diffractometer equipped with a θ/2θ goniometer, a Cu tube working at 50 kV and 40 mA (CuKα radiation, λ=1.5419 Å), a divergence slit=1/4°, Soller slits=0.04 rad, an anti-scatter slit=1/4°, a receiving slit=0.10 mm, and a secondary curved graphite monochromator. Data were collected in the range 2-35° of 2theta using a step-scan technique with a step size=0.02° and a time per step=20 s.

Figure 10:
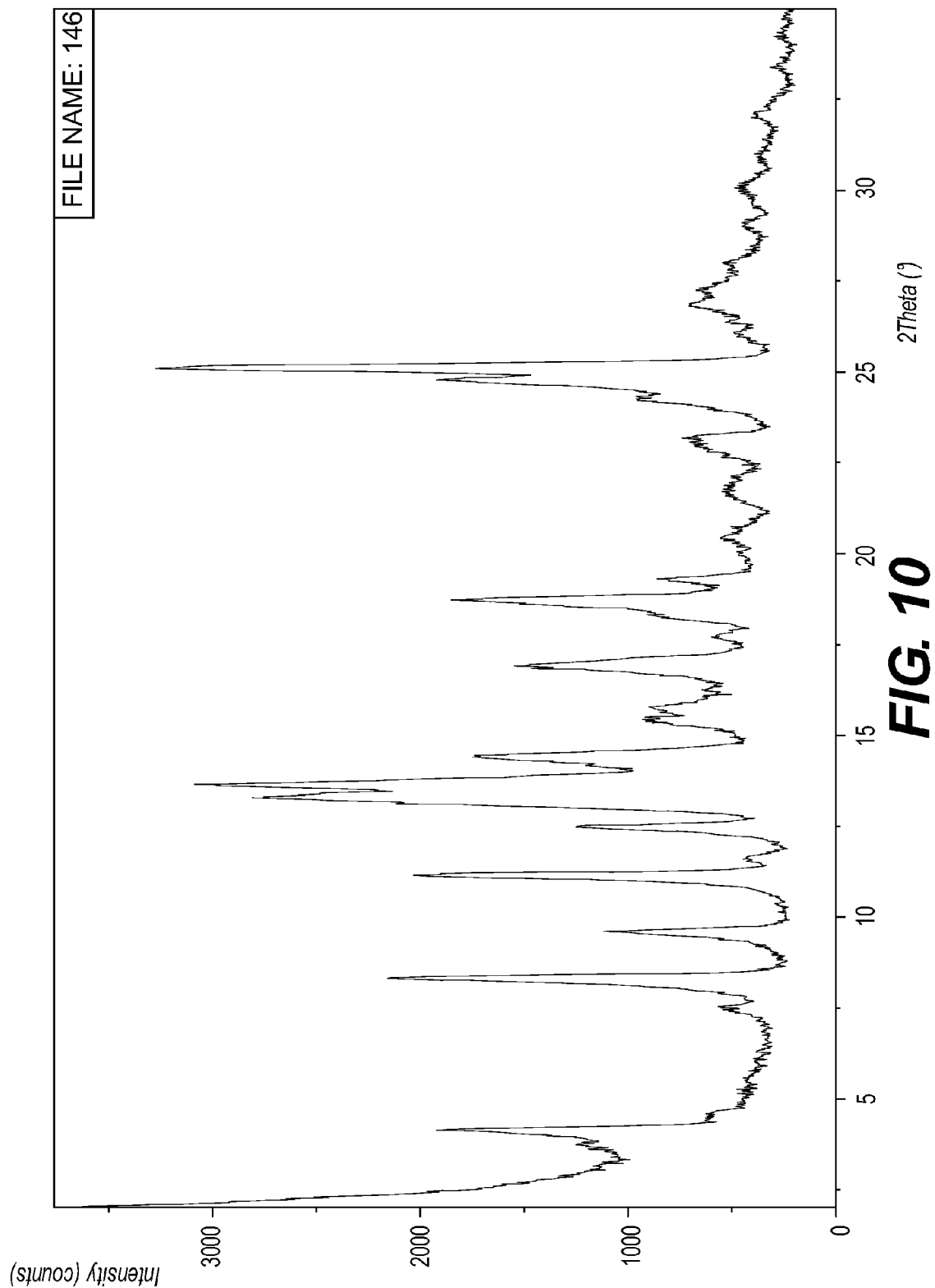
FIG. 10 presents a characteristic XRPD pattern of the crystalline Form IV of (1R,2R)-7-chloro-3-[2-(2,4-difluorophenyl)-2-hydroxy-1-methyl-3-(1H-1,2,4-triazol-1-yl)propyl]quinazolin-4(3H)-one.

A characteristic XRPD pattern distinctive to Form IV was observed, as represented by FIG. 10. The characteristic 2-theta positions and corresponding intensities observed for this specific pattern are summarized below in Table 10.

TABLE 10

Characteristic XRPD 2-Theta Positions and Intensities for Form IV

| Characteristic XRPD 2-theta positions (+/−0.2) | Characteristic XRPD Relative Intensity (%) |
|---|---|
| 3.74 | 14 |
| 4.15 | 39 |
| 7.5 | 8 |
| 8.33 | 64 |
| 9.61 | 30 |
| 11.16 | 60 |
| 11.61 | 7 |
| 12.49 | 34 |
| 13.29 | 84 |
| 13.64 | 96 |
| 14.41 | 51 |
| 15.43 | 22 |
| 15.74 | 22 |
| 16.90 | 42 |
| 17.71 | 12 |
| 18.25 | 20 |
| 18.74 | 51 |
| 19.30 | 21 |
| 20.43 | 11 |
| 21.78 | 10 |
| 23.20 | 15 |
| 24.26 | 24 |
| 24.78 | 57 |
| 25.11 | 100 |
| 26.03 | 8 |
| 26.86 | 16 |
| 27.25 | 15 |
| 28.00 | 10 |
| 29.05 | 7 |
| 30.07 | 8 |

TABLE 10-continued

Characteristic XRPD 2-Theta Positions and Intensities for Form IV

| Characteristic XRPD 2-theta positions (+/−0.2) | Characteristic XRPD Relative Intensity (%) |
|---|---|
| 30.91 | 5 |
| 32.05 | 5 |

The most relevant 2-theta positions and corresponding intensities observed for this specific XRPD pattern for Form IV are summarized below in Table 11.

TABLE 11

Most Relevant XRPD 2-Theta Positions and Intensities for Form IV

| Characteristic XRPD 2-theta positions (+/−0.2) | Characteristic XRPD Relative Intensity (%) |
|---|---|
| 4.15 | 39 |
| 7.5 | 8 |
| 8.33 | 64 |
| 9.61 | 30 |
| 11.16 | 60 |
| 12.49 | 34 |
| 13.29 | 84 |
| 13.64 | 96 |
| 14.41 | 51 |
| 16.90 | 42 |
| 18.74 | 51 |
| 24.78 | 57 |
| 25.11 | 100 |

A set of XRPD peaks that uniquely characterizes Form IV has 2-theta positions at about 4.15, 7.5, 8.33, 9.61, 11.16, 12.49, 13.29, 13.64, 14.41, 16.90, 18.74, 24.78, and 25.11+/−0.2.

Figure 11:
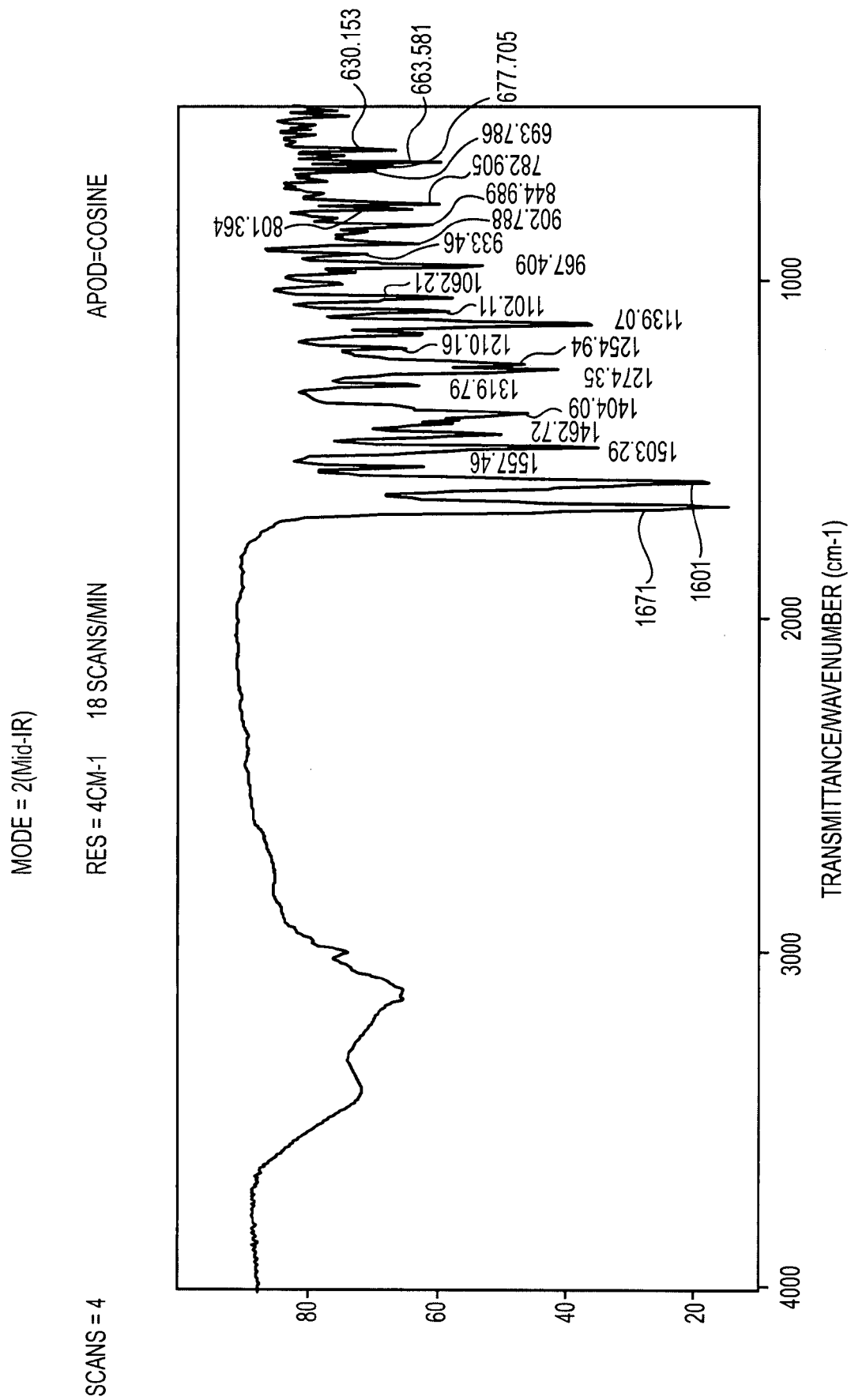
FIG. 11 presents a characteristic IR spectrum of the crystalline Form IV of (1R,2R)-7-chloro-3-[2-(2,4-difluorophenyl)-2-hydroxy-1-methyl-3-(1H-1,2,4-triazol-1-yl)propyl]quinazolin-4(3H)-one.

The complete infrared spectrum of the crystalline Form IV is shown in FIG. 11 and is characterized as summarized below in Table 12.

TABLE 12

Infrared Spectrum for Form IV
Frequency (cm$^{-1}$) (+/−0.1)

1671.0
1601.0
1557.5
1503.3
1462.7
1404.1
1319.8
1274.4
1254.9
1210.2
1139.1
1102.1
1062.2
967.4
933.5
902.8
845.0
801.4
782.9
693.8
677.7
663.6
630.2

Figure 12:
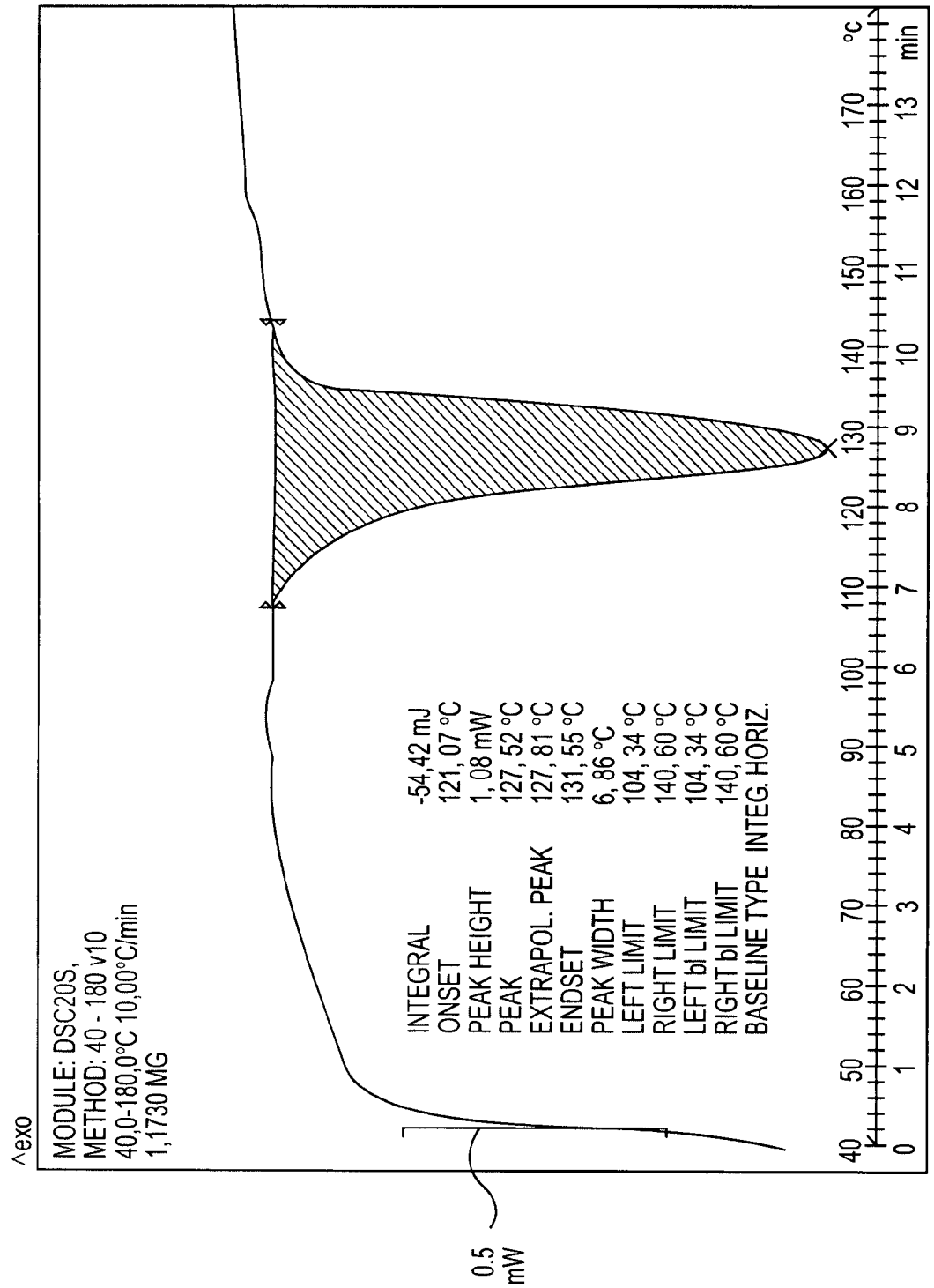
FIG. 12 presents a characteristic DSC thermogram of the crystalline Form IV of (1R,2R)-7-chloro-3-[2-(2,4-difluorophenyl)-2-hydroxy-1-methyl-3-(1H-1,2,4-triazol-1-yl)propyl]quinazolin-4(3H)-one.

Form IV was further observed to have a characteristic endothermic peak onset observed at about 121+/−5 degrees C. using DSC analysis, as represented by FIG. 12.

Form V

Crystalline Form V of (1R,2R)-7-chloro-3-[2-(2,4-difluorophenyl)-2-hydroxy-1-methyl-3-(1H-1,2,4-triazol-1-yl)propyl]quinazolin-4(3H)-one was likewise in part identified by its characteristic XRPD pattern. The XRPD pattern for Form V was measured at room temperature using a Philips X'Pert diffractometer equipped with a θ/2θ goniometer, a Cu tube working at 50 kV and 40 mA (CuKα radiation, λ=1.5419 Å), a divergence slit=1/4°, Soller slits=0.04 rad, an anti-scatter slit=1/4°, a receiving slit=0.10 mm, and a secondary curved graphite monochromator. Data were collected in the range 2-350 of 2theta using a step-scan technique with a step size=0.02° and a time per step=20 s.

Figure 13:
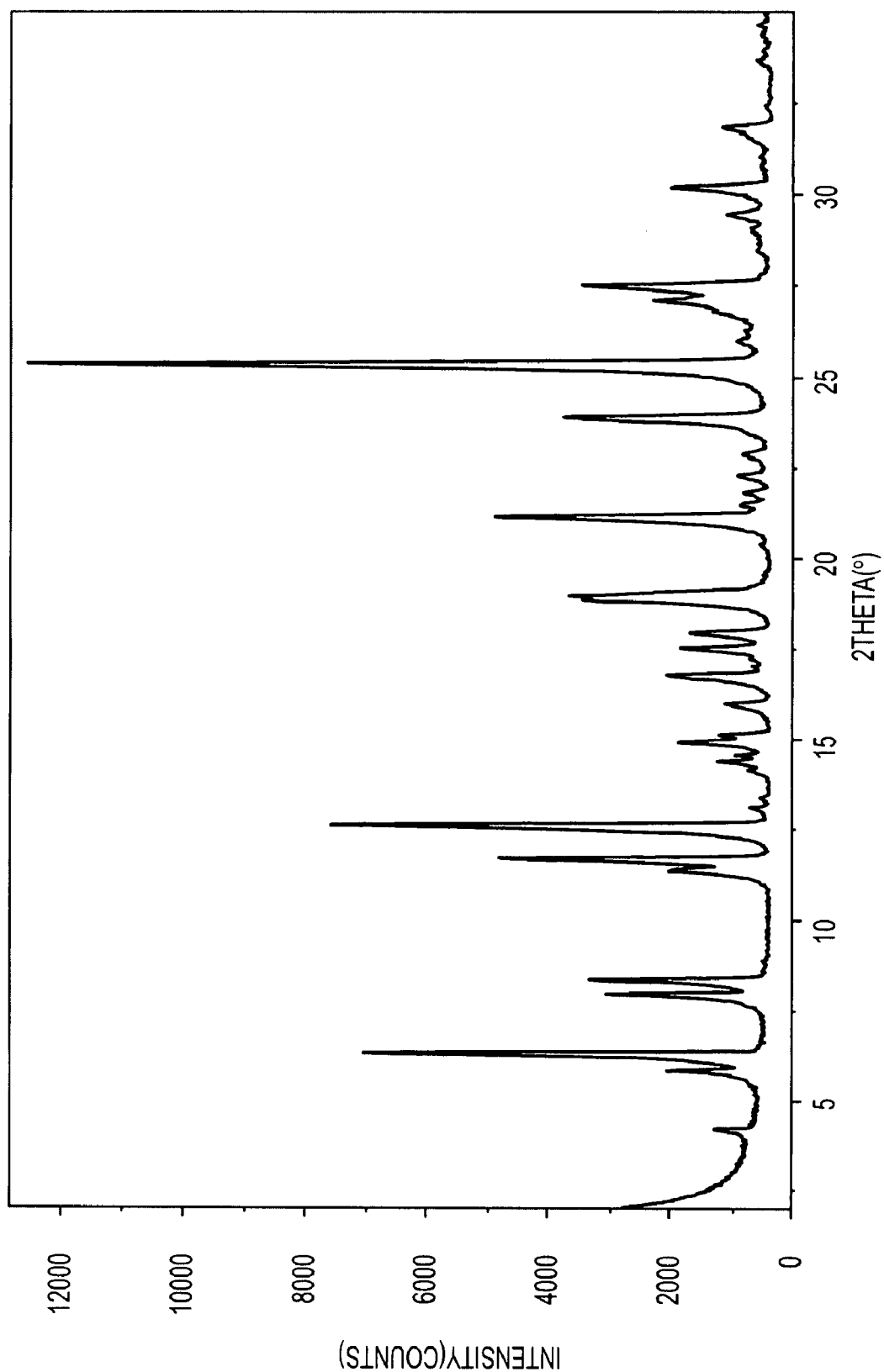
FIG. 13 presents a characteristic XRPD pattern of the crystalline Form V of (1R,2R)-7-chloro-3-[2-(2,4-difluorophenyl)-2-hydroxy-1-methyl-3-(1H-1,2,4-triazol-1-yl)propyl]quinazolin-4(3H)-one.

A characteristic XRPD pattern distinctive to Form V was observed, as represented by FIG. 13. The characteristic 2-theta positions and corresponding intensities observed for this specific pattern are summarized below in Table 13.

TABLE 13

Characteristic XRPD 2-Theta Positions and Intensities for Form V

| Characteristic XRPD 2-theta positions (+/−0.2) | Characteristic XRPD Relative Intensity (%) |
|---|---|
| 4.17 | 5 |
| 5.83 | 12 |
| 6.28 | 51 |
| 7.96 | 21 |
| 8.35 | 23 |
| 11.35 | 13 |
| 11.66 | 36 |
| 12.57 | 59 |
| 13.06 | 2 |
| 13.34 | 1 |
| 14.11 | 3 |
| 14.34 | 7 |
| 14.52 | 4 |
| 14.89 | 12 |
| 15.09 | 7 |
| 15.95 | 5 |
| 16.74 | 14 |
| 16.98 | 2 |
| 17.21 | 3 |
| 17.49 | 12 |
| 17.91 | 11 |
| 18.82 | 25 |
| 18.9 | 27 |
| 20.36 | 1 |
| 21.1 | 37 |
| 21.47 | 4 |
| 21.79 | 4 |
| 22.27 | 4 |
| 22.88 | 4 |
| 23.86 | 28 |
| 25.3 | 100 |
| 25.95 | 5 |
| 26.2 | 3 |
| 26.74 | 7 |
| 27.04 | 16 |
| 27.44 | 25 |
| 28.43 | 2 |
| 28.98 | 2 |
| 29.41 | 6 |
| 30.13 | 13 |
| 30.73 | 1 |
| 30.98 | 1 |
| 31.78 | 7 |
| 32.36 | 1 |
| 33.61 | 2 |
| 33.9 | 1 |
| 34.35 | 1 |
| 34.62 | 2 |

The most relevant 2-theta positions and corresponding intensities observed for this specific XRPD pattern for Form V are summarized below in Table 14.

TABLE 14

Most Relevant XRPD 2-Theta Positions and Intensities for Form V

| Characteristic XRPD 2-theta positions (+/−0.2) | Characteristic XRPD Relative Intensity (%) |
|---|---|
| 4.17 | 5 |
| 5.83 | 12 |
| 6.28 | 51 |
| 7.96 | 21 |
| 8.35 | 23 |
| 11.35 | 13 |
| 11.66 | 36 |
| 12.57 | 59 |
| 14.34 | 7 |
| 14.89 | 12 |
| 15.95 | 5 |
| 16.74 | 14 |
| 17.49 | 12 |
| 18.9 | 27 |
| 21.1 | 37 |
| 23.86 | 28 |
| 25.3 | 100 |
| 27.04 | 16 |
| 27.44 | 25 |
| 30.13 | 13 |

A set of XRPD peaks that uniquely characterizes Form V has 2-theta positions at about 4.17, 5.83, 6.28, 7.96, 8.35, 11.35, 11.66, 12.57, 14.34, 14.89, 15.95, 16.74, 17.49, 18.9, 21.1, 23.86, 25.3, 27.04, 27.44, and 30.13+/−0.2.

Figure 14:
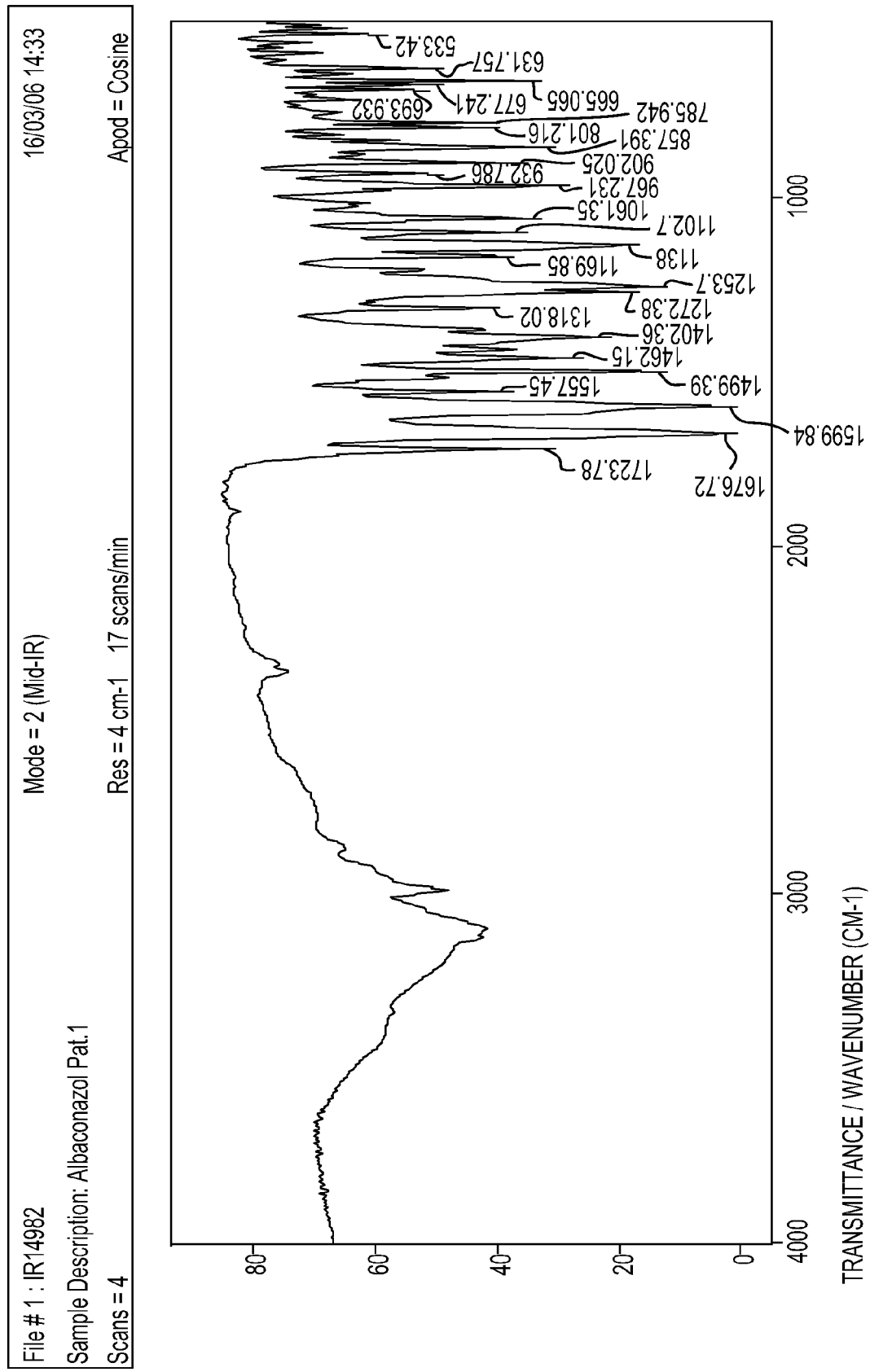
FIG. 14 presents a characteristic IR spectrum of the crystalline Form V of (1R,2R)-7-chloro-3-[2-(2,4-difluorophenyl)-2-hydroxy-1-methyl-3-(1H-1,2,4-triazol-1-yl)propyl]quinazolin-4(3H)-one.

The complete infrared spectrum of the crystalline Form V is shown in FIG. 14 and is characterized as summarized below in Table 15.

TABLE 15

| Infrared Spectrum for Form V Frequency (cm$^{-1}$) (+/−0.1) |
|---|
| 1723.8 |
| 1676.0 |
| 1599.0 |
| 1557.5 |
| 1499.4 |
| 1462.2 |
| 1402.4 |
| 1318.0 |
| 1272.4 |
| 1253.7 |
| 1169.9 |
| 1138.0 |
| 1102.7 |
| 1061.4 |
| 967.2 |
| 932.8 |
| 902.0 |
| 857.4 |
| 801.2 |
| 785.9 |
| 693.9 |
| 677.2 |
| 665.1 |
| 631.8 |
| 533.4 |

Figure 15:
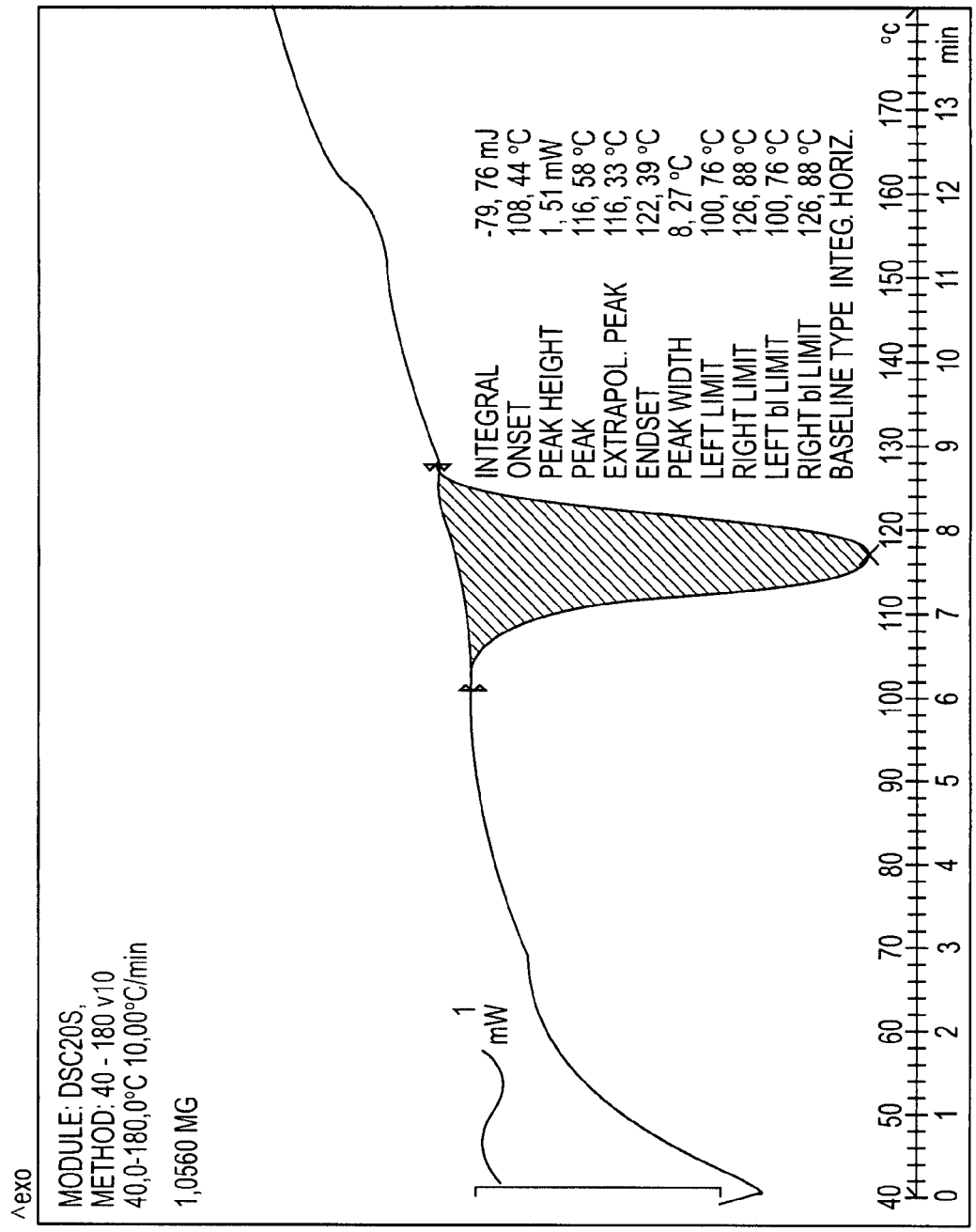
FIG. 15 presents a characteristic DSC thermogram of the crystalline Form V of (1R,2R)-7-chloro-3-[2-(2,4-difluorophenyl)-2-hydroxy-1-methyl-3-(1H-1,2,4-triazol-1-yl)propyl]quinazolin-4(3H)-one.

Form V was further observed to have a characteristic endothermic peak onset observed at about 108+−5 degrees C. using DSC analysis, as represented by FIG. 15.

Form VI

Crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one was likewise in part identified by its characteristic XRPD pattern. Optimal XRPD methods to analyze Form VI can typically either entail spinning a capillary (Inel) using t method (1) shown below or spinning a flat sample (Shimadzu) using a method (2) shown below. FIG. 16 is obtained using the following method (1).

(1) The XRPD pattern for Form VI was measured using an Inel XRG-3000 diffractometer equipped with a CPS (Curved Position Sensitive) detector with a 2θ range of 120°. Real time data were collected using Cu—Kα radiation. The tube voltage and amperage were set to 40 kV and 30 mA, respectively. The monochromator slit was set at 5 mm by 160 μm. The pattern is displayed from 2.5-40 °2θ. Samples were prepared for analysis by packing them into thin-walled glass capillaries. Each capillary was mounted onto a goniometer head that is motorized to permit spinning of the capillary during data acquisition. The samples were analyzed for 300 sec. Instrument calibration was performed using a silicon reference standard.

(2) Alternatively, X-ray powder diffraction (XRPD) analyses were performed using a Shimadzu XRD-6000 X-ray powder diffractometer using Cu Kα radiation. The instrument was equipped with a long fine focus X-ray tube. The tube voltage and amperage were set to 40 kV and 40 mA, respectively. The divergence and scattering slits were set at 1° and the receiving slit was set at 0.15 mm. Diffracted radiation was detected by a NaI scintillation detector. A θ-2θ continuous scan at 1°/min (0.4 sec/0.02° step) from 2.5 to 40° 2θ was used. The sample was spun at a rate of 25 rpm. A silicon standard was analyzed to check the instrument alignment. Data were collected and analyzed using XRD-6100/7000 v. 5.0. Samples were prepared for analysis by placing them in an aluminum holder with silicon well.

A characteristic XRPD pattern distinctive to Form VI was observed using the above method (1), as represented by FIG. 16. The characteristic 2-theta positions and corresponding intensities observed for this specific pattern are summarized below in Table 16.

TABLE 16

Characteristic XRPD 2-Theta Positions and Intensities for Form VI

| Characteristic XRPD 2-theta positions (+/−0.2) | Characteristic XRPD Relative Intensity (%) |
|---|---|
| 10.1 | 20 |
| 12.1 | 26 |
| 13.3 | 31 |
| 14.5 | 60 |
| 15.0 | 13 |
| 16.0 | 100 |
| 16.6 | 32 |
| 17.0 | 14 |
| 17.4 | 29 |
| 18.8 | 12 |
| 19.2 | 12 |
| 19.7 | 15 |
| 21.1 | 63 |
| 22.3 | 45 |
| 23.9 | 12 |
| 24.2 | 12 |

TABLE 16-continued

Characteristic XRPD 2-Theta Positions and Intensities for Form VI

| Characteristic XRPD 2-theta positions (+/−0.2) | Characteristic XRPD Relative Intensity (%) |
|---|---|
| 24.8 | 24 |
| 25.7 | 39 |
| 26.7 | 23 |
| 27.6 | 39 |
| 28.6 | 35 |
| 28.9 | 13 |
| 29.3 | 16 |
| 29.7 | 10 |
| 30.0 | 12 |
| 30.5 | 15 |
| 30.8 | 13 |
| 31.3 | 19 |
| 33.3 | 9 |
| 33.7 | 8 |
| 34.3 | 8 |
| 35.0 | 11 |
| 35.5 | 8 |
| 36.5 | 9 |
| 36.7 | 8 |
| 37.4 | 10 |
| 39.5 | 8 |

The most relevant 2-theta positions and corresponding intensities observed for this specific XRPD pattern for Form VI are summarized below in Table 17.

TABLE 17

Most Relevant XRPD 2-Theta Positions and Intensities for Form VI

| Characteristic XRPD 2-theta positions (+/−0.2) | Characteristic XRPD Relative Intensity (%) |
|---|---|
| 10.1 | 20 |
| 14.5 | 60 |
| 16.0 | 100 |
| 16.6 | 32 |
| 17.0 | 14 |
| 17.4 | 29 |
| 19.7 | 15 |
| 21.1 | 63 |
| 22.3 | 45 |
| 24.8 | 24 |
| 25.7 | 39 |
| 26.7 | 23 |
| 27.6 | 39 |
| 28.6 | 35 |
| 28.9 | 13 |
| 29.3 | 16 |
| 30.5 | 15 |
| 30.8 | 13 |
| 31.3 | 19 |

A first set of XRPD peaks that uniquely characterizes Form VI has 2-theta positions at about 21.1, 24.8, and 25.7+/−0.2. A second set of XRPD peaks that uniquely characterizes Form VI has 2-theta positions at about 14.5, 16.0, 21.1, 24.8, and 25.7+/−0.2. A third set of XRPD peaks that uniquely characterizes Form VI has 2-theta positions at about 10.1, 14.5, 16.0, 21.1, 24.8, and 25.7+/−0.2. A fourth set of XRPD peaks that uniquely characterizes Form VI has a 2-theta position at about 10.1+/−0.2.

Infrared spectra were acquired on a Magna-IR 860® Fourier transform infrared (FT-IR) spectrophotometer (Thermo Nicolet) equipped with an Ever-Glo mid/far IR source, an extended range potassium bromide (KBr) beamsplitter, and a deuterated triglycine sulfate (DTGS) detector. A diffuse reflectance accessory (the Collector™, Thermo Spectra- Tech) was used for sampling. Each spectrum represents 256 co-added scans collected at a spectral resolution of 2 cm$^{-1}$. Sample preparation consisted of placing the sample into a 13-mm diameter cup and leveling the material with a frosted glass slide. A background data set was acquired with an alignment mirror in place. A Log 1/R (R=reflectance) spectrum was acquired by taking a ratio of these two data sets against each other. Wavelength calibration was performed using polystyrene.

The infrared spectrum of the crystalline Form VI is shown in FIGS. 17a-c and is characterized as summarized below in Table 18.

TABLE 18

| Infrared Spectrum for Form VI Frequency (cm$^{-1}$) (+/−0.1) |
|---|
| 1607 |
| 1555 |
| 1468 |
| 1400 |
| 1361 |
| 1316 |
| 1280 |
| 1218 |
| 1165 |
| 1102 |
| 1014 |
| 976 |
| 938 |
| 760 |
| 698 |

Form VI was further observed to have a characteristic endothermic peak onset observed at a temperature ranging from about 102 to about 108+/−5 degrees C. using DSC analysis, as represented by FIGS. 18a-c.

Hot stage Microscopic Analysis was also performed on Form VI as follows. A sample of Form VI was sandwiched between glass coverslips and placed on a hot stage. The sample was heated at a controlled rate and visually observed using a microscope with crossed-polarized light. Visual changes with the sample were recorded. The melting temperature of Form VI was 100-103° C. and no further changes were noted at 154° C.

Hot stage microscopy (HSM) was performed using a Linkam hot stage (model FTIR 600) mounted on a Leica DMLP microscope. Samples were observed using crossed polarized light. Images were captured using a SPOT Insight™ color digital camera with SPOT Software v. 4.5.9. The hot stage was calibrated using USP melting point standards.

Structure Determination of Form VI

Crystal Data and Data Collection Parameters Used for Determining the Structure of Form VI are provided (Table 19), calculated positional parameters and their estimated standard deviations (Table 20), calculated anisotropic temperature factor coefficients (Tables 21), calculated bond distances (Table 22), calculated bond angles (Table 23), calculated torsion angles (Tables 24), and calculated hydrogen bond distances and angles (Table 25).

Data Collection

A colorless needle of $C_{20}H_{16}ClF_2N_5O_2 \cdot H_2O$ was isolated from 1:1 ethanol-water slurry and the structure determined by single crystal X-ray diffraction. The needle having approximate dimensions of 0.45×0.13×0.13 mm was mounted on a glass fiber in a random orientation. Preliminary examination and data collection were performed using Mo Kα radiation (λ=0.71073 Å) on a Nonius KappaCCD equipped with a graphite crystal, incident beam monochromator.

Cell constants for data collection were obtained from least-squares refinement, using the setting angles of 6937 reflections in the range 3<θ<25°. The refined mosaicity from DENZO/SCALEPACK (Z. Otwinowski and W. Minor, *Methods Enzymol.*, 276, 307, 1997, the contents of which are hereby incorporated by reference in their entirety) was 1.24° indicating poor crystal quality. The space group was determined by the program XPREP (XPREP in SHELXTL version 6.12, Bruker AXS Inc., Madison, Wis., USA, 2002, the contents of the program, and user manuals of the program, are hereby incorporated by reference in their entirety.) From the systematic presences of h00 h=2n, 0k0 k=2n, 00l l=2n, and from subsequent least-squares refinement, the space group was determined to be $P2_12_12_1$ (No. 19).

The data were collected at a temperature of 150 K. Data were collected to a maximum 2θ of 50.1°.

Data Reduction

A total of 6937 reflections were collected, of which 3516 were unique. Frames were integrated with DENZO-SMN (Z. Otwinowski and W. Minor, *Methods Enzymol.*, 276, 307, 1997).

Lorentz and polarization corrections were applied to the data. The linear absorption coefficient is 2.3/cm for Mo Kα radiation. An empirical absorption correction using SCALEPACK (Z. Otwinowski and W. Minor, *Methods Enzymol.*, 276, 307, 1997) was applied. Transmission coefficients ranged from 0.934 to 0.970. Intensities of equivalent reflections were averaged. The agreement factor for the averaging was 14.2% based on intensity.

Structure Solution and Refinement

The structure was solved by direct methods using SIR2004 (M. C. Burla, R. Caliandro, M. Camalli, B. Carrozzini, G. L. Cascarano, L. De Caro, C. Giacovazzo, G. Polidori, and R. Spagna., *J. Appl. Cryst.*, 38, 381, 2005, the contents of which are hereby incorporated by reference in their entirety). The remaining atoms were located in succeeding difference Fourier syntheses. Hydrogen atoms were included in the refinement but restrained to ride on the atom to which they are bonded. The structure was refined in full-matrix least-squares by minimizing the function:

$$\Sigma w (|F_o|^2 - |F_c|^2)^2$$

The weight w is defined as $1/[\sigma^2(F_o^2)+1.9322P]$ where $P=(F_o^2+2F_c^2)/3$.

Scattering factors were taken from the "International Tables for Crystallography" ("International Tables for Crystallography", Vol. C, Kluwer Academic Publishers, Utrecht, The Netherlands, 1992, Tables 4.2.6.8 and 6.1.1.4., the contents of which are hereby incorporated by reference in their entirety). Of the 3516 reflections used in the refinements only 2654 reflections with $F_o^2 > 2\sigma(F_o^2)$ were used in calculating R1. The final cycle of refinement included 293 variable parameters and converged (largest parameter shift was <0.01 times its estimated standard deviation) with unweighted and weighted agreement factors of:

$$R = \Sigma |F_o - F_c|/\Sigma F_o = 0.069$$

$$R_w = \sqrt{(\Sigma w(F_o^2 - F_c^2)^2 / \Sigma w(F_o^2)^2)} = 0.102$$

The standard deviation of an observation of unit weight was 1.09. The highest peak in the final difference Fourier had a height of 0.26 e/Å$^3$. The minimum negative peak had a height of −0.30 e/Å$^3$. The factor for the determination of the absolute structure (H. D. Flack, *Acta Cryst.*, A39, 876, 1983, the contents of which are hereby incorporated by reference in their entirety) refined to 0.02.

Refinement was performed on a LINUX PC using SHELX-97 (G. M. Sheldrick, SHELXL97. *A Program for Crystal Structure Refinement*. Univ. of Gottingen, Germany, 1997, the contents of the program, and user manuals of the program, are hereby incorporated by reference in their entirety). Crystallographic drawings were done using programs ORTEP (C. K. Johnson, ORTEPII, Report ORNL-5138, Oak Ridge National Laboratory, Tennessee, USA, 1976 the contents of the report, the program, and user manuals of the program, are hereby incorporated by reference in their entirety) and Mercury (Mercury 1.4.1, Cambridge Crystallographic Diffraction Center, Cambridge, 2005, the contents of the program, and user manuals of the program, are hereby incorporated by reference in their entirety).

The orthorhombic cell parameters and calculated volume were: a=12.0968(15)Å, b=12.6245(16)Å, c=13.3520(19)Å, α=β=γ=90°, V=2039.1(5)Å$^3$. For Z=4 and formula weight=449.85 g/mol, the calculated density is 1.47 g/cm$^3$. The quality of the structure obtained was reasonable, as indicated by the R-value of 6.9%. Usually R-values in the range of 2 to 6% are quoted for the most reliably determined structures (J. Glusker, K. Trueblood, *Crystal Structure Analysis: A Primer*, 2$^{nd}$ ed.; Oxford University press: New York, 1985; p. 87, the contents of the entire book are hereby incorporated by reference in their entirety).

Structure Drawings and Packing Diagrams

Figure 19:
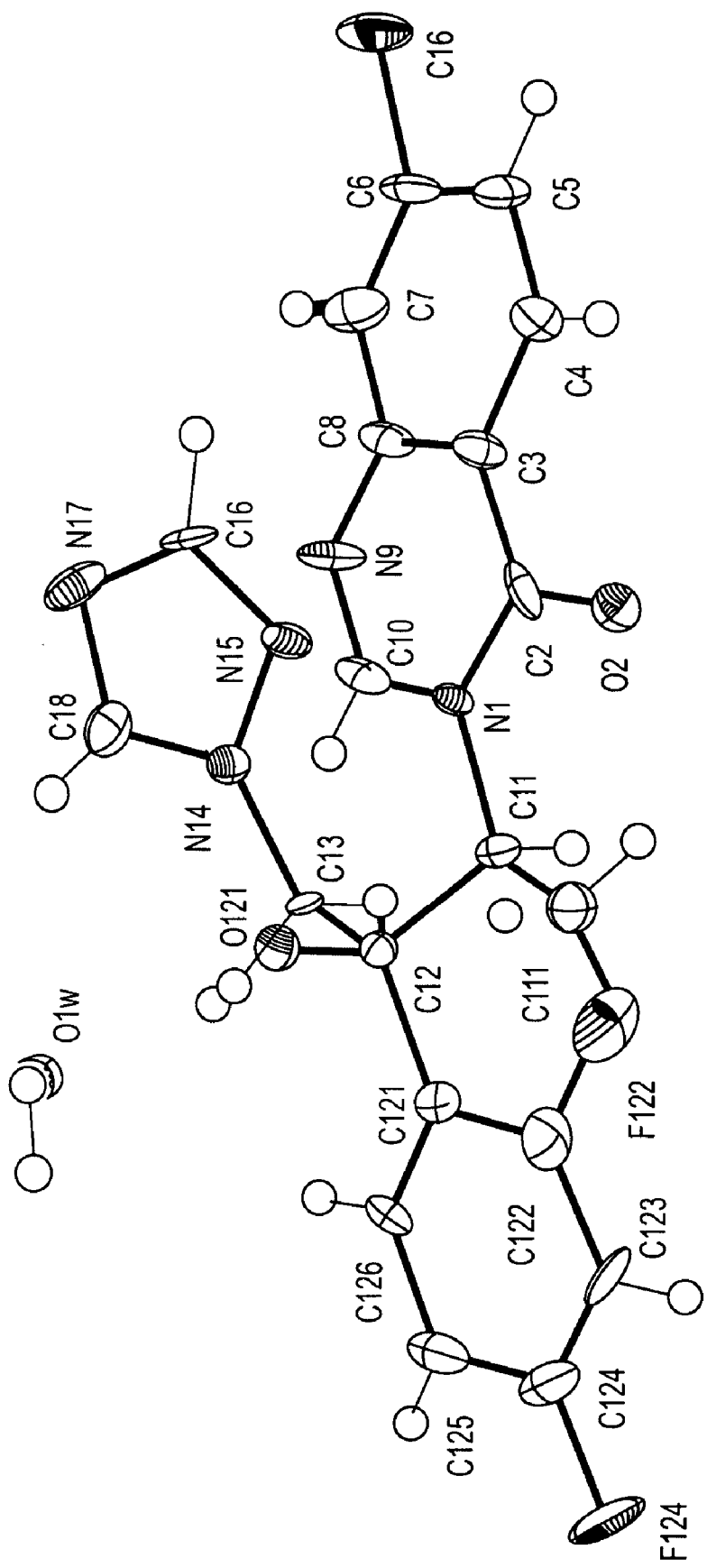
FIG. 19 presents an ORTEP drawing of the crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one. Atoms are represented by 50% probability anisotropic ellipsoids.

An ORTEP drawing of Form VI is shown in FIG. 19. The asymmetric unit shown in FIG. 19 contains one molecule of Form VI and one water molecule.

Figure 20:
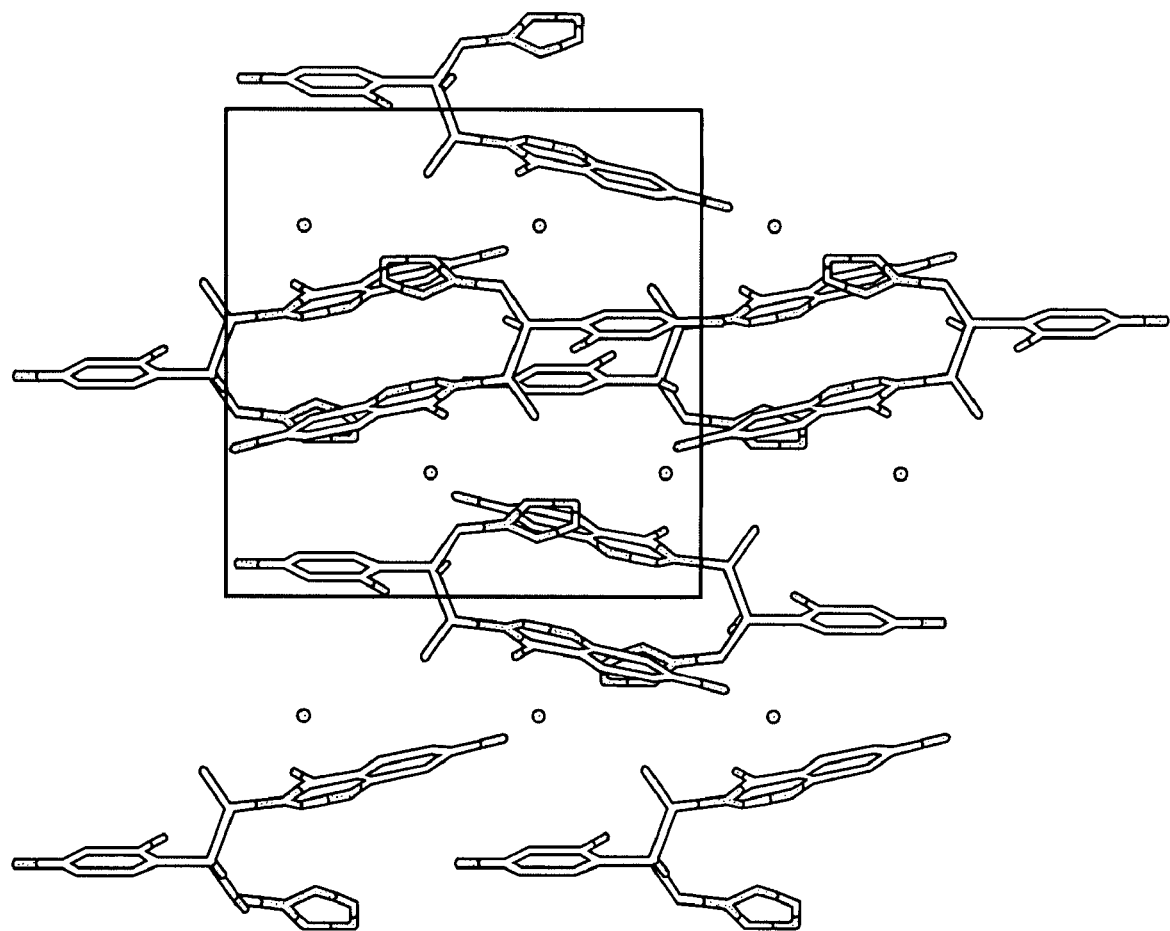
FIG. 20 presents a packing diagram of the crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one viewed along the a crystallographic axis. Hydrogen atoms omitted for clarity.
Figure 21:
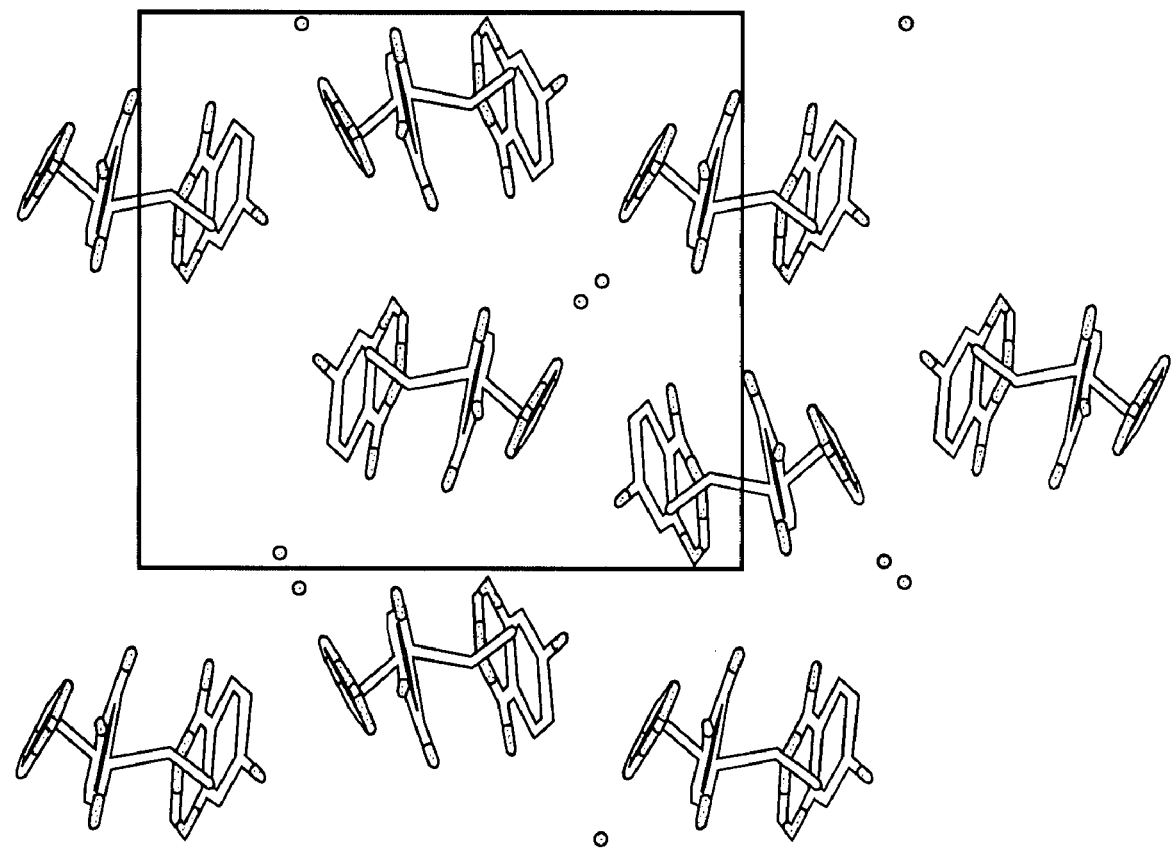
FIG. 21 presents a packing diagram of the crystalline Form VI of (1R,2R)-7-chloro-3-[2-(2,4-difluorophenyl)-2-hydroxy-1-methyl-3-(1H-1,2,4-triazol-1-yl)propyl] quinazolin-4(3H)-one viewed along the b crystallographic axis. Hydrogen atoms omitted for clarity.
Figure 22:
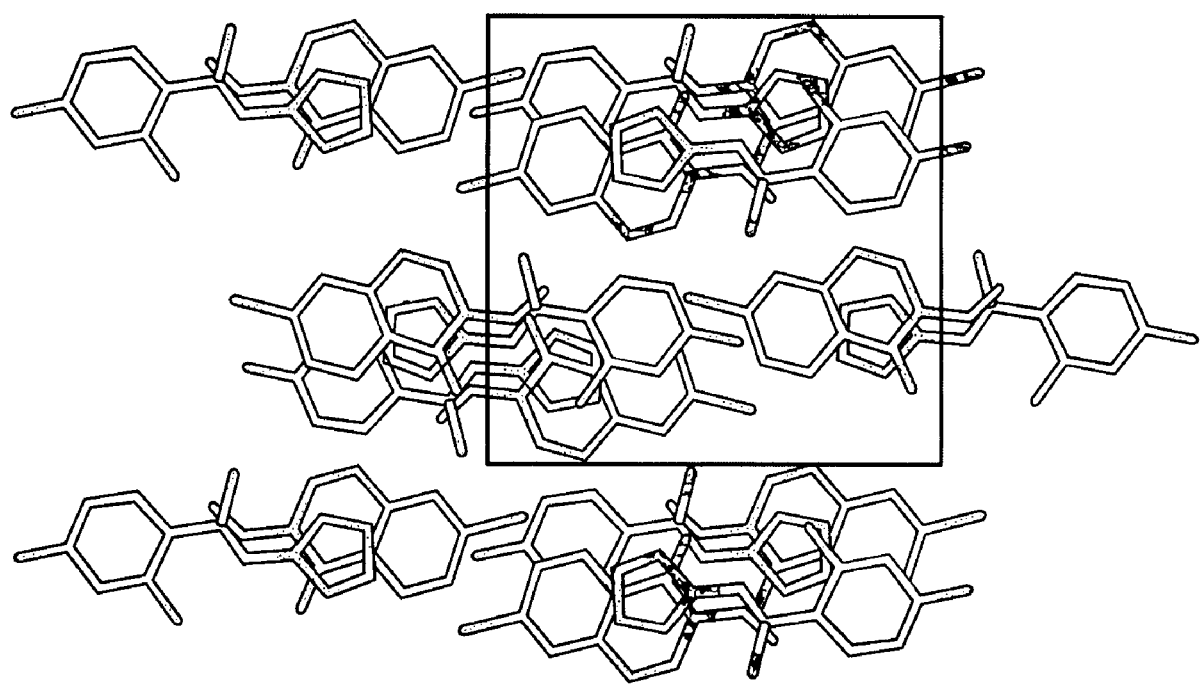
FIG. 22 presents a packing diagram of the crystalline Form VI of (1R,2R)-7-chloro-3-[2-(2,4-difluorophenyl)-2-hydroxy-1-methyl-3-(1H-1,2,4-triazol-1-yl)propyl] quinazolin-4(3H)-one viewed along the c crystallographic axis. Hydrogen atoms are omitted for clarity.
Figure 23:
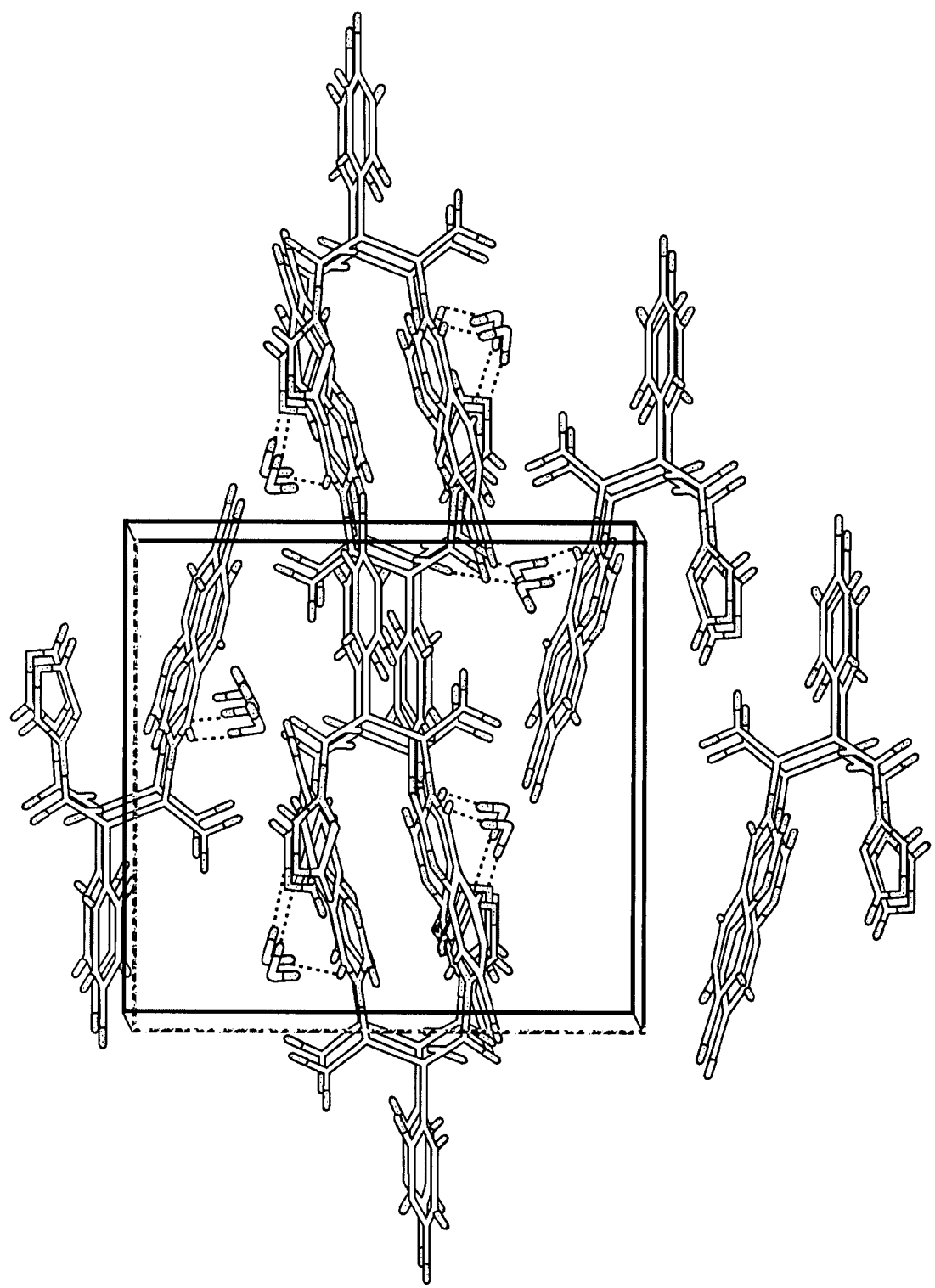
FIG. 23 presents a packing diagram of the crystalline Form VI of (1R,2R)-7-chloro-3-[2-(2,4-difluorophenyl)-2-hydroxy-1-methyl-3-(1H-1,2,4-triazol-1-yl)propyl] quinazolin-4(3H)-one viewed along the a crystallographic axis with hydrogen bonding represented with dashed lines. Hydrogen bonding between adjacent molecules of (1R,2R)-7-chloro-3-[2-(2,4-difluorophenyl)-2-hydroxy-1-methyl-3-(1H-1,2,4-triazol-1-yl)propyl] quinazolin-4(3H)-one and water molecules generates a three-dimensional network. The water molecules reside in channels running parallel to the crystallographic a axis.

Packing diagrams viewed along the a, b, and c crystallographic axes are shown in FIG. 20, FIG. 21, and FIG. 22, respectively. Hydrogen bonding between adjacent Form VI and water molecules generates a three-dimensional network. The water molecules reside in channels running parallel to the crystallographic a axis (FIG. 23). Packing diagrams were prepared using Mercury modeling software. Hydrogen bonds are represented as dashed lines.

TABLE 19

Crystal Data and Data Collection Parameters for Form VI

| | |
|---|---|
| formula | $C_{20}H_{18}ClF_2N_5O_3$ |
| formula weight | 449.85 |
| space group | $P2_12_12_1$ (No. 19) |
| a, Å | 12.0968(15) |
| b, Å | 12.6245(16) |
| c, Å | 13.3520(19) |
| V, Å$^3$ | 2039.1(5) |
| Z | 4 |
| $d_{calc}$, g cm$^{-3}$ | 1.465 |
| crystal dimensions, mm | 0.45 × 0.13 × 0.13 |
| temperature, K | 150. |
| radiation (wavelength, Å) | Mo K$_\alpha$ (0.71073) |
| monochromator | graphite |
| linear abs coef, mm$^{-1}$ | 0.234 |
| absorption correction applied | empirical$^a$ |
| transmission factors: min, max | 0.93, 0.97 |
| diffractometer | Nonius KappaCCD |
| h, k, l range | −14 to 13 −13 to 15 −15 to 14 |
| 2θ range, deg | 6.10-50.06 |
| mosaicity, deg | 1.24 |
| programs used | SHELXTL |
| $F_{000}$ | 928.0 |
| weighting | $1/[\sigma^2(F_o^2) + 1.9322P]$ where $P = (F_o^2 + 2F_c^2)/3$ |
| data collected | 6937 |

TABLE 19-continued

Crystal Data and Data Collection Parameters for Form VI

| | |
|---|---|
| unique data | 3516 |
| $R_{int}$ | 0.142 |
| data used in refinement | 3516 |
| cutoff used in R-factor calculations | $F_o^2 > 2.0\sigma(F_o^2)$ |
| data with I > 2.0σ(I) | 2654 |
| number of variables | 293 |
| largest shift/esd in final cycle | 0.00 |
| $R(F_o)$ | 0.069 |
| $R_w(F_o^2)$ | 0.102 |
| goodness of fit | 1.090 |
| absolute structure determination | Flack parameter$^b$ (0.0(1)) |

$^a$Otwinowski Z. & Minor, W. Methods Enzymol. 1997, 276, 307.

$^b$Flack, H. D. Acta Cryst., Sect. A_1983, A39, 876.

The contents of each of the above documents are hereby incorporated by reference in their entirety.

TABLE 20

Positional Parameters and Their Estimated Standard Deviation for Form VI.

| Atom | x | y | z | U(Å$^2$) |
|---|---|---|---|---|
| Cl(6) | 0.38011(12) | 0.06405(10) | 0.20395(11) | 0.0426(4) |
| F(122) | 0.1484(2) | −0.7003(2) | −0.0092(2) | 0.0421(9) |
| F(124) | 0.2838(3) | −1.04231(19) | −0.0623(2) | 0.0380(9) |
| O(2) | 0.1710(3) | −0.4220(2) | 0.1181(2) | 0.0254(9) |
| O(1W) | 0.5178(3) | −0.6048(3) | −0.2666(2) | 0.0177(9) |
| O(121) | 0.4677(2) | −0.5746(2) | −0.0753(2) | 0.0142(8) |
| N(1) | 0.3503(3) | −0.4423(3) | 0.0691(3) | 0.0164(10) |
| N(9) | 0.4826(3) | −0.3028(3) | 0.0776(3) | 0.0257(12) |
| N(14) | 0.2910(3) | −0.4375(3) | −0.1488(2) | 0.0154(10) |
| N(15) | 0.2114(3) | −0.3697(3) | −0.1160(3) | 0.0187(10) |
| N(17) | 0.3499(3) | −0.2784(3) | −0.1897(3) | 0.0247(12) |
| C(2) | 0.2617(4) | −0.3816(4) | 0.1032(3) | 0.0183(14) |
| C(3) | 0.2891(4) | −0.2712(3) | 0.1223(3) | 0.0200(12) |
| C(4) | 0.2081(4) | −0.2000(4) | 0.1565(3) | 0.0297(15) |
| C(5) | 0.2348(4) | −0.0974(4) | 0.1799(3) | 0.0310(15) |
| C(6) | 0.3431(4) | −0.0648(4) | 0.1691(3) | 0.0267(14) |
| C(7) | 0.4250(4) | −0.1310(4) | 0.1345(3) | 0.0267(15) |
| C(8) | 0.3984(4) | −0.2358(3) | 0.1100(3) | 0.0207(12) |
| C(10) | 0.4543(4) | −0.3990(4) | 0.0599(3) | 0.0240(15) |
| C(11) | 0.3343(4) | −0.5585(3) | 0.0555(3) | 0.0177(12) |
| C(12) | 0.3568(3) | −0.5985(3) | −0.0518(3) | 0.0137(10) |
| C(13) | 0.2799(3) | −0.5508(3) | −0.1335(3) | 0.0147(12) |
| C(16) | 0.2501(4) | −0.2765(3) | −0.1432(3) | 0.0207(14) |
| C(18) | 0.3719(4) | −0.3820(3) | −0.1928(3) | 0.0220(14) |
| C(111) | 0.4023(4) | −0.6178(4) | 0.1350(3) | 0.0287(15) |
| C(121) | 0.3371(3) | −0.7191(3) | −0.0559(3) | 0.0147(10) |
| C(122) | 0.2358(4) | −0.7645(4) | −0.0344(4) | 0.0230(14) |
| C(123) | 0.2148(4) | −0.8713(4) | −0.0346(3) | 0.0280(15) |
| C(124) | 0.3019(4) | −0.9365(4) | −0.0591(3) | 0.0243(15) |
| C(125) | 0.4059(4) | −0.8976(4) | −0.0816(3) | 0.0240(15) |
| C(126) | 0.4207(4) | −0.7891(3) | −0.0799(3) | 0.0167(12) |
| H(121) | 0.472(5) | −0.597(5) | −0.140(5) | 0.09(2)* |
| H(1W1) | 0.450(6) | −0.606(5) | −0.305(5) | 0.08(2)* |
| H(1W2) | 0.554(6) | −0.671(6) | −0.281(5) | 0.10(2)* |

Starred atoms were refined isotropically $U_{eq} = (1/3)\Sigma_i\Sigma_j U_{ij}a^*_ia^*_ja_i \cdot a_j$

TABLE 21

Anisotropic Temperature Factor Coefficients - U's for Form VI.

| Name | U(1, 1) | U(2, 2) | U(3, 3) | U(1, 2) | U(1, 3) | U(2, 3) |
|---|---|---|---|---|---|---|
| Cl(6) | 0.0667(10) | 0.0160(6) | 0.0452(8) | 0.0063(7) | −0.0101(7) | −0.0137(6) |
| F(122) | 0.0162(15) | 0.0290(17) | 0.081(2) | 0.0003(14) | 0.0181(15) | 0.0111(15) |
| F(124) | 0.065(2) | 0.0081(14) | 0.0408(17) | −0.0112(14) | −0.0032(16) | 0.0013(12) |
| O(2) | 0.0259(19) | 0.0216(18) | 0.0286(19) | 0.0062(16) | 0.0115(15) | 0.0013(15) |
| O(1W) | 0.0132(17) | 0.0184(18) | 0.0216(19) | 0.0062(15) | 0.0012(14) | −0.0012(14) |
| O(121) | 0.0086(15) | 0.0142(16) | 0.0197(18) | −0.0045(14) | 0.0019(13) | −0.0024(14) |
| N(1) | 0.0129(19) | 0.0162(19) | 0.020(2) | 0.0030(19) | 0.0018(16) | −0.0032(17) |
| N(9) | 0.022(2) | 0.015(2) | 0.040(3) | 0.0064(19) | −0.0055(19) | −0.0124(18) |
| N(14) | 0.0161(19) | 0.0140(19) | 0.016(2) | 0.0026(19) | 0.0006(16) | 0.0007(17) |
| N(15) | 0.019(2) | 0.016(2) | 0.021(2) | 0.0089(18) | −0.0013(17) | −0.0018(16) |
| N(17) | 0.022(2) | 0.013(2) | 0.039(3) | −0.0065(19) | −0.001(2) | 0.0042(18) |
| C(2) | 0.013(3) | 0.028(3) | 0.014(2) | 0.007(2) | 0.0034(19) | −0.001(2) |
| C(3) | 0.028(3) | 0.017(2) | 0.015(2) | 0.008(2) | −0.005(2) | −0.0020(19) |
| C(4) | 0.038(3) | 0.025(3) | 0.026(3) | 0.010(3) | 0.012(2) | 0.002(2) |
| C(5) | 0.047(3) | 0.018(3) | 0.028(3) | 0.017(3) | 0.009(3) | −0.001(2) |
| C(6) | 0.040(3) | 0.016(2) | 0.024(3) | 0.008(3) | −0.004(2) | −0.009(2) |
| C(7) | 0.033(3) | 0.021(3) | 0.026(3) | 0.000(2) | −0.011(2) | −0.007(2) |
| C(8) | 0.026(3) | 0.018(2) | 0.018(2) | 0.005(2) | −0.005(2) | −0.006(2) |
| C(10) | 0.020(3) | 0.023(3) | 0.029(3) | 0.014(2) | −0.001(2) | −0.005(2) |
| C(11) | 0.020(2) | 0.012(2) | 0.021(3) | 0.001(2) | 0.002(2) | 0.000(2) |
| C(12) | 0.010(2) | 0.012(2) | 0.019(2) | 0.0033(19) | 0.0014(19) | 0.0011(18) |
| C(13) | 0.016(2) | 0.005(2) | 0.023(3) | 0.000(2) | 0.001(2) | 0.0005(19) |
| C(16) | 0.030(3) | 0.005(2) | 0.027(3) | 0.003(2) | −0.005(2) | −0.001(2) |
| C(18) | 0.015(2) | 0.024(3) | 0.027(3) | −0.002(2) | 0.002(2) | 0.007(2) |
| C(111) | 0.042(3) | 0.027(3) | 0.017(3) | 0.003(3) | 0.002(2) | 0.002(2) |
| C(121) | 0.013(2) | 0.015(2) | 0.016(2) | −0.003(2) | −0.0034(19) | −0.0021(19) |
| C(122) | 0.011(2) | 0.025(3) | 0.033(3) | 0.001(2) | 0.006(2) | 0.004(2) |
| C(123) | 0.027(3) | 0.022(3) | 0.035(3) | −0.017(3) | −0.002(2) | 0.010(2) |
| C(124) | 0.038(3) | 0.013(3) | 0.022(3) | −0.006(2) | −0.009(2) | 0.000(2) |
| C(125) | 0.036(3) | 0.018(3) | 0.018(3) | 0.008(2) | −0.003(2) | −0.003(2) |
| C(126) | 0.015(2) | 0.021(3) | 0.014(2) | 0.004(2) | −0.0002(19) | −0.0050(19) |

The form of the anisotropic temperature factor is: $\exp[-2\pi^2 h^2 a^{*2} U(1,1) + k^2 b^{*2} U(2,2) + l^2 c^{*2} U(3,3) + 2hka^*b^* U(1,2) + 2hla^*c^* U(1,3) + 2klb^*c^* U(2,3)]$ where $a^*$, $b^*$, and $c^*$ are reciprocal lattice constants.

TABLE 22

Table of Bond Distances in Angstrom for Form VI.

| Atom 1 | Atom 2 | Distance |
|---|---|---|
| Cl6 | C6 | 1.750(5) |
| F122 | C122 | 1.374(5) |
| F124 | C124 | 1.354(5) |
| O2 | C2 | 1.226(5) |
| O1W | H1W1 | 0.96(7) |
| O1W | H1W2 | 0.96(7) |
| O121 | C12 | 1.410(5) |
| O121 | H121 | 0.91(6) |
| N1 | C10 | 1.378(5) |
| N1 | C2 | 1.393(5) |
| N1 | C11 | 1.490(5) |
| N9 | C10 | 1.283(5) |
| N9 | C8 | 1.393(5) |
| N14 | C18 | 1.340(5) |
| N14 | N15 | 1.361(5) |
| N14 | C13 | 1.451(5) |
| N15 | C16 | 1.317(5) |
| N17 | C18 | 1.335(5) |
| N17 | C16 | 1.357(6) |
| C2 | C3 | 1.456(6) |
| C3 | C8 | 1.406(7) |
| C3 | C4 | 1.406(6) |
| C4 | C5 | 1.371(6) |
| C4 | H4 | 0.950 |
| C5 | C6 | 1.381(7) |
| C5 | H5 | 0.950 |
| C6 | C7 | 1.376(6) |
| C7 | C8 | 1.400(6) |
| C7 | H7 | 0.950 |
| C10 | H10 | 0.950 |
| C11 | C111 | 1.538(6) |
| C11 | C12 | 1.544(6) |
| C11 | H11 | 1.000 |
| C12 | C121 | 1.541(6) |
| C12 | C13 | 1.554(6) |
| C13 | H13A | 0.990 |
| C13 | H13B | 0.990 |
| C16 | H16 | 0.950 |
| C18 | H18 | 0.950 |
| C111 | H11A | 0.980 |
| C111 | H11B | 0.980 |
| C111 | H11C | 0.980 |
| C121 | C126 | 1.381(6) |
| C121 | C122 | 1.383(6) |
| C122 | C123 | 1.371(6) |
| C123 | C124 | 1.376(7) |
| C123 | H123 | 0.950 |
| C124 | C125 | 1.383(7) |
| C125 | C126 | 1.382(6) |
| C125 | H125 | 0.950 |
| C126 | H126 | 0.950 |

Numbers in parentheses are estimated standard deviations in the least significant digits.

TABLE 23

Table of Bond Angles in Degrees for Form VI.

| Atom 1 | Atom 2 | Atom 3 | Angle |
|---|---|---|---|
| H1W1 | O1W | H1W2 | 105(5) |
| C12 | O121 | H121 | 102(4) |

TABLE 23-continued

Table of Bond Angles in Degrees for Form VI.

| Atom 1 | Atom 2 | Atom 3 | Angle |
|---|---|---|---|
| C10 | N1 | C2 | 120.8(3) |
| C10 | N1 | C11 | 119.9(4) |
| C2 | N1 | C11 | 118.8(3) |
| C10 | N9 | C8 | 115.9(4) |
| C18 | N14 | N15 | 109.2(3) |
| C18 | N14 | C13 | 130.2(4) |
| N15 | N14 | C13 | 120.7(3) |
| C16 | N15 | N14 | 102.8(3) |
| C18 | N17 | C16 | 102.1(4) |
| O2 | C2 | N1 | 120.8(4) |
| O2 | C2 | C3 | 124.9(4) |
| N1 | C2 | C3 | 114.2(4) |
| C8 | C3 | C4 | 119.4(4) |
| C8 | C3 | C2 | 119.9(4) |
| C4 | C3 | C2 | 120.7(4) |
| C5 | C4 | C3 | 120.9(5) |
| C5 | C4 | H4 | 119.50 |
| C3 | C4 | H4 | 119.50 |
| C4 | C5 | C6 | 118.8(5) |
| C4 | C5 | H5 | 120.60 |
| C6 | C5 | H5 | 120.60 |
| C7 | C6 | C5 | 122.5(4) |
| C7 | C6 | Cl6 | 118.0(4) |
| C5 | C6 | Cl6 | 119.4(4) |
| C6 | C7 | C8 | 119.1(4) |
| C6 | C7 | H7 | 120.40 |
| C8 | C7 | H7 | 120.40 |
| N9 | C8 | C7 | 118.6(4) |
| N9 | C8 | C3 | 122.1(4) |
| C7 | C8 | C3 | 119.3(4) |
| N9 | C10 | N1 | 127.1(4) |
| N9 | C10 | H10 | 116.40 |
| N1 | C10 | H10 | 116.40 |
| N1 | C11 | C111 | 109.0(3) |
| N1 | C11 | C12 | 114.4(3) |
| C111 | C11 | C12 | 112.8(3) |
| N1 | C11 | H11 | 106.70 |
| C111 | C11 | H11 | 106.70 |
| C12 | C11 | H11 | 106.70 |
| O121 | C12 | C121 | 110.5(3) |
| O121 | C12 | C11 | 107.7(3) |
| C121 | C12 | C11 | 109.2(3) |
| O121 | C12 | C13 | 109.3(3) |
| C121 | C12 | C13 | 105.4(3) |
| C11 | C12 | C13 | 114.7(3) |
| N14 | C13 | C12 | 115.2(3) |
| N14 | C13 | H13A | 108.50 |
| C12 | C13 | H13A | 108.50 |
| N14 | C13 | H13B | 108.50 |
| C12 | C13 | H13B | 108.50 |
| H13A | C13 | H13B | 107.50 |
| N15 | C16 | N17 | 115.2(4) |
| N15 | C16 | H16 | 122.40 |
| N17 | C16 | H16 | 122.40 |
| N17 | C18 | N14 | 110.7(4) |
| N17 | C18 | H18 | 124.70 |
| N14 | C18 | H18 | 124.70 |
| C11 | C111 | H11A | 109.50 |
| C11 | C111 | H11B | 109.50 |
| H11A | C111 | H11B | 109.50 |
| C11 | C111 | H11C | 109.50 |
| H11A | C111 | H11C | 109.50 |
| H11B | C111 | H11C | 109.50 |
| C126 | C121 | C122 | 115.6(4) |
| C126 | C121 | C12 | 121.8(4) |
| C122 | C121 | C12 | 122.6(4) |
| C123 | C122 | F122 | 116.0(4) |
| C123 | C122 | C121 | 124.8(4) |
| F122 | C122 | C121 | 119.2(4) |
| C122 | C123 | C124 | 116.6(4) |
| C122 | C123 | H123 | 121.70 |
| C124 | C123 | H123 | 121.70 |
| F124 | C124 | C123 | 118.3(4) |
| F124 | C124 | C125 | 119.3(4) |
| C123 | C124 | C125 | 122.4(4) |
| C126 | C125 | C124 | 117.8(4) |
| C126 | C125 | H125 | 121.10 |
| C124 | C125 | H125 | 121.10 |
| C121 | C126 | C125 | 122.9(4) |
| C121 | C126 | H126 | 118.50 |
| C125 | C126 | H126 | 118.50 |

Numbers in parentheses are estimated standard deviations in the least significant digits.

TABLE 24

Table of Torsional Angles in Degrees for Form VI.

| Atom 1 | Atom 2 | Atom 3 | Atom 4 | Angle |
|---|---|---|---|---|
| C(10) | N(1) | C(2) | O(2) | −174.81 (0.39) |
| C(10) | N(1) | C(2) | C(3) | 2.77 (0.57) |
| C(11) | N(1) | C(2) | O(2) | −2.80 (0.60) |
| C(11) | N(1) | C(2) | C(3) | 174.78 (0.35) |
| C(2) | N(1) | C(10) | N(9) | −1.77 (0.69) |
| C(11) | N(1) | C(10) | N(9) | −173.69 (0.42) |
| C(2) | N(1) | C(11) | C(12) | 121.76 (0.42) |
| C(2) | N(1) | C(11) | C(111) | −110.99 (0.43) |
| C(10) | N(1) | C(11) | C(12) | −66.15 (0.51) |
| C(10) | N(1) | C(11) | C(111) | 61.10 (0.50) |
| C(10) | N(9) | C(8) | C(3) | −0.18 (0.61) |
| C(10) | N(9) | C(8) | C(7) | 177.40 (0.39) |
| C(8) | N(9) | C(10) | N(1) | 0.30 (0.66) |
| C(13) | N(14) | N(15) | C(16) | −179.88 (0.34) |
| C(18) | N(14) | N(15) | C(16) | 0.23 (0.44) |
| N(15) | N(14) | C(13) | C(12) | −106.76 (0.39) |
| C(18) | N(14) | C(13) | C(12) | 73.10 (0.49) |
| N(15) | N(14) | C(18) | N(17) | 0.70 (0.46) |
| C(13) | N(14) | C(18) | N(17) | −179.17 (0.36) |
| N(14) | N(15) | C(16) | N(17) | −1.11 (0.49) |
| C(18) | N(17) | C(16) | N(15) | 1.51 (0.51) |
| C(16) | N(17) | C(18) | N(14) | −1.27 (0.46) |
| O(2) | C(2) | C(3) | C(4) | −2.88 (0.65) |
| O(2) | C(2) | C(3) | C(8) | 174.82 (0.39) |
| N(1) | C(2) | C(3) | C(4) | 179.65 (0.38) |
| N(1) | C(2) | C(3) | C(8) | −2.64 (0.56) |
| C(2) | C(3) | C(4) | C(5) | 176.35 (0.39) |
| C(8) | C(3) | C(4) | C(5) | −1.36 (0.61) |
| C(2) | C(3) | C(8) | N(9) | 1.44 (0.61) |
| C(2) | C(3) | C(8) | C(7) | −176.12 (0.38) |
| C(4) | C(3) | C(8) | N(9) | 179.18 (0.39) |
| C(4) | C(3) | C(8) | C(7) | 1.62 (0.59) |
| C(3) | C(4) | C(5) | C(6) | 0.13 (0.63) |
| C(4) | C(5) | C(6) | Cl(6) | −177.11 (0.32) |
| C(4) | C(5) | C(6) | C(7) | 0.87 (0.64) |
| Cl(6) | C(6) | C(7) | C(8) | 177.41 (0.32) |
| C(5) | C(6) | C(7) | C(8) | −0.59 (0.64) |
| C(6) | C(7) | C(8) | N(9) | −178.31 (0.38) |
| C(6) | C(7) | C(8) | C(3) | −0.67 (0.60) |
| N(1) | C(11) | C(12) | O(121) | 60.12 (0.44) |
| N(1) | C(11) | C(12) | C(13) | −61.82 (0.47) |
| N(1) | C(11) | C(12) | C(121) | −179.83 (0.35) |
| C(111) | C(11) | C(12) | O(121) | −65.16 (0.42) |
| C(111) | C(11) | C(12) | C(13) | 172.90 (0.34) |
| C(111) | C(11) | C(12) | C(121) | 54.88 (0.44) |
| O(121) | C(12) | C(13) | N(14) | −56.58 (0.41) |
| C(11) | C(12) | C(13) | N(14) | 64.51 (0.43) |
| C(121) | C(12) | C(13) | N(14) | −175.33 (0.31) |
| O(121) | C(12) | C(121) | C(122) | 178.91 (0.39) |
| O(121) | C(12) | C(121) | C(126) | −0.02 (0.76) |
| C(11) | C(12) | C(121) | C(122) | 60.61 (0.52) |
| C(11) | C(12) | C(121) | C(126) | −118.32 (0.42) |
| C(13) | C(12) | C(121) | C(122) | −63.16 (0.50) |
| C(13) | C(12) | C(121) | C(126) | 117.91 (0.40) |
| C(12) | C(121) | C(122) | F(122) | 0.62 (0.68) |
| C(12) | C(121) | C(122) | C(123) | −178.33 (0.43) |
| C(126) | C(121) | C(122) | F(122) | 179.61 (0.39) |
| C(126) | C(121) | C(122) | C(123) | 0.66 (0.71) |

TABLE 24-continued

Table of Torsional Angles in Degrees for Form VI.

| Atom 1 | Atom 2 | Atom 3 | Atom 4 | Angle |
|---|---|---|---|---|
| C(12) | C(121) | C(126) | C(125) | 178.31 (0.38) |
| C(122) | C(121) | C(126) | C(125) | −0.69 (0.63) |
| F(122) | C(122) | C(123) | C(124) | −179.60 (0.38) |
| C(121) | C(122) | C(123) | C(124) | −0.62 (0.72) |
| C(122) | C(123) | C(124) | F(124) | −178.55 (0.39) |
| C(122) | C(123) | C(124) | C(125) | 0.59 (0.63) |
| F(124) | C(124) | C(125) | C(126) | 178.50 (0.36) |
| C(123) | C(124) | C(125) | C(126) | −0.64 (0.61) |
| C(124) | C(125) | C(126) | C(121) | 0.70 (0.62) |

TABLE 25

Table of Hydrogen Bond Distances and Angles for Form VI.

| D | H | A | D-H | A-H | D-A | D-H-A |
|---|---|---|---|---|---|---|
| O(121) | H(121) | O(1W) | 0.91(7) | 1.78(7) | 2.653(5) | 159(6) |
| O(1W) | H(1W1) | O(2) | 0.97(7) | 1.82(7) | 2.775(6) | 168(6) |
| O(1W) | H(1W2) | N(17) | 0.96(7) | 1.83(7) | 2.776(7) | 167(7) |

Pharmaceutical Compositions

In another preferred embodiment, the present subject matter relates to pharmaceutical compositions containing an anti-microbially or anti-fungally effective amount of any of the pure crystalline polymorphs I, II, III, IV, V, or VI of (1R,2R)-7-chloro-3-[2-(2,4-difluorophenyl)-2-hydroxy-1-methyl-3-(1H-1,2,4-triazol-1-yl)propyl]quinazolin-4(3H)-one or a pharmaceutically acceptable salt or derivative thereof, and a pharmaceutically acceptable carrier. The crystalline Form III, Form IV, or Form VI is particularly preferred in this regard. Form VI is most preferred in this regard. The present subject matter also contemplates compositions comprising one or more of the crystalline forms described herein. In a particularly preferred embodiment, these pharmaceutical compositions comprise any one of the pure crystalline Forms I, II, III, IV, V, or VI having a purity of at least 85% by weight, or not more than 15% by weight of other forms of the compound and any residual solvents. In a more preferred embodiment, these pharmaceutical compositions comprise any one of the pure crystalline Forms I, II, III, IV, V, or VI having a purity of at least 90% by weight, with a purity of at least 95% by weight being most preferred. In another preferred embodiment, these pharmaceutical compositions comprise any one of the pure crystalline Forms I, II, III, IV, V, or VI having a purity ranging from about 85% to 99.99% purity on a % weight basis. More preferably, the compositions comprise the crystalline form having a purity ranging from about 90% to 99.99% purity on a % weight basis. Further more preferably, the crystalline form has a purity ranging from about 93% to 99.99% purity on a % weight basis. Yet more preferably, the compositions comprise the crystalline form having a purity ranging from about 95% to 99.99% purity on a % weight basis. Yet even more preferably, the compositions comprise the crystalline form having a purity ranging from about 97% to 99.99% purity on a % weight basis. Of these embodiments, compositions comprising Form VI are especially preferred.

The phrase "pharmaceutically acceptable carrier" as used in this regard refers to any inactive ingredient present in one of the herein described compositions in an amount effective to enhance the stability, effectiveness, or otherwise of said composition. Non-limiting examples of such pharmaceutically acceptable carriers include diluents, excipients, suspending agents, lubricating agents, adjuvants, vehicles, delivery systems, emulsifiers, disintegrants, absorbants, adsorbents, preservatives, surfactants, colorants, flavorants, emollients, buffers, pH modifiers, thickeners, water softening agents, humectants, fragrances, stabilizers, conditioning agents, chelating agents, sweeteners, propellants, anticaking agents, viscosity increasing agents, solubilizers, plasticizers, penetration enhancing agents, glidants, film forming agents, fillers, coating agents, binders, antioxidants, stiffening agents, wetting agents, or any mixture of these components.

The carriers useful herein may further include one or more compatible solid or liquid filler, diluents, or encapsulating materials which are suitable for human or animal administration.

Biocompatible carriers, as used herein, are components that do not cause any interactions which substantially reduce the efficacy of the pharmaceutical composition in an ordinary user environment. Possible pharmaceutical carriers must be of sufficiently low toxicity to make them suitable for administration to the subject of treatment.

Some non-limiting examples of substances which can serve as a carrier herein include sugar, starch, cellulose and its derivatives, powered tragacanth, malt, gelatin, talc, stearic acid, magnesium stearate, calcium sulfate, vegetable oils, polyols, alginic acid, pyrogen-free water, isotonic saline, phosphate buffer solutions, cocoa butter (suppository base), emulsifier as well as other non-toxic pharmaceutically compatible substances used in other pharmaceutical formulations. Wetting agents and lubricants such as sodium lauryl sulfate, as well as coloring agents, flavoring agents, excipients, tabletting agents, stabilizers, antioxidants, and preservatives may also be present.

Any non-toxic, inert, and effective carrier may be used to formulate the compositions contemplated herein. Suitable pharmaceutically acceptable carriers, excipients, and diluents in this regard are well known to those of skill in the art, such as those described in *The Merck Index*, Thirteenth Edition, Budavari et al., Eds., Merck & Co., Inc., Rahway, N.J. (2001); the CTFA (Cosmetic, Toiletry, and Fragrance Association) *International Cosmetic Ingredient Dictionary and Handbook*, Tenth Edition (2004); and the "Inactive Ingredient Guide", U.S. Food and Drug Administration (FDA) Center for Drug Evaluation and Research (CDER) Office of Management, http://www.accessdata.fda.gov/scripts/cder/iig/index.cfm, the contents of all of which are hereby incorporated by reference in their entirety. Examples of preferred pharmaceutically acceptable excipients, carriers and diluents useful in the present compositions include distilled water, physiological saline, Ringer's solution, dextrose solution, Hank's solution, and DMSO.

These additional inactive components, as well as effective formulations and administration procedures, are well known in the art and are described in standard textbooks, such as *Goodman and Gillman's: The Pharmacological Bases of Therapeutics*, 8th Ed., Gilman et al. Eds. Pergamon Press (1990) and *Remington's Pharmaceutical Sciences*, 18th Ed., Mack Publishing Co., Easton, Pa. (1990), both of which are incorporated by reference herein in their entirety.

The carrier may comprise, in total, from about 0.1% to about 99.99999% by weight of the pharmaceutical compositions presented herein.

Preferred compositions herein can be in the form of oral or topical compositions. The oral compositions contemplated herein may take the form of tablets, capsules, soft-gels, hard gels, solutions, suspensions, powders, dispersible granules, cachets, combinations thereof, or any other oral pharmaceutical dosage form as would commonly be known in the art.

A solid carrier can be one or more substances which may also act as diluents, flavoring agents, solubilizers, lubricants, suspending agents, binders, or tablet disintegration agents; it can also be an encapsulating material. In powders, the carrier can be a finely divided solid which is in admixture with the active compound. In a tablet, the active compound can be mixed with a carrier having the necessary binding properties in suitable proportions and compacted in the size and shape desired. Non-limiting examples of suitable solid carriers include magnesium carbonate, magnesium stearate, talc, sugar, lactose, pectin, dextrin, starch, gelatin, tragacanth, methyl cellulose, sodium carboxymethylcellulose, hydroxypropyl methylcellulose, hydroxyethylcellulose, hydroxypropylcellulose, other cellulose derivatives, a low melting wax, cocoa butter, and the like.

Similarly, the topical compositions contemplated herein may take the form of a gel, cream, lotion, suspension, emulsion, aerosol, ointment, foam, mousse, shampoo, nail lacquer, nail product, vaginal product, combinations thereof, or any other topical pharmaceutical dosage form commonly known in the art. Other pharmaceutical and cosmetic treatment compositions known to those skilled in the art, including liquids and balms, are additionally contemplated as falling within the scope of the present subject matter. Further, the present subject matter contemplates applying any of these compositions with an applicator. Non-limiting examples of useful applicators in this regard include a pledget, a pad, and combinations thereof. Additionally, the present subject matter further contemplates that any of these topical compositions can be provided in a package of less than 5 g topical composition as a unit of use.

Emulsions, such as oil-in-water or water-in-oil systems, as well as a base (vehicle or carrier) for the topical formulation can be selected to provide effectiveness of the active ingredient and/or avoid allergic and irritating reactions (e.g., contact dermatitis) caused by ingredients of the base or by the active ingredient.

In severe cases, occlusive therapy may be useful herein. Covering the treated area with a nonporous occlusive dressing can increase the absorption and effectiveness of the compounds and compositions described herein. Usually, a polyethylene film (plastic household wrap) is applied overnight over cream or ointment, since a cream or ointment is usually less irritating than lotion in occlusive therapy. Plastic tapes may be impregnated with drug and are especially convenient for treating isolated or recalcitrant lesions; children and (less often) adults may experience pituitary and adrenal suppression after prolonged occlusive therapy over large areas.

Suitable gelling agents which may be useful in the present compositions include but are not limited to aqueous gelling agents, such as neutral, anionic, and cationic polymers, and mixtures thereof. Exemplary polymers which may be useful in the instant compositions include carboxy vinyl polymers, such as carboxypolymethylene. A preferred gelling agent is Carbopol® brand polymer such as is available from Noveon Inc., Cleveland, Ohio. Carbopol® polymers are high molecular weight, crosslinked, acrylic acid-based polymers. Carbopol® homopolymers are polymers of acrylic acid crosslinked with allyl sucrose or allylpentaerythritol. Carbopol® copolymers are polymers of acrylic acid, modified by long chain (C10-C30) alkyl acrylates, and crosslinked with allyl-pentaerythritol.

Other suitable gelling agents include cellulosic polymers, such as gum arabic, gum tragacanth, locust bean gum, guar gum, xanthan gum, cellulose gum, methylcellulose, hydroxyethylcellulose, hydroxypropylcellulose, and hydroxypropylmethylcellulose.

Methods of Treatment

In another preferred embodiment, the present subject matter relates to a method of treating and/or preventing microbial or fungal infections or disorders in a mammal comprising administering to a mammal in need thereof an effective amount of any of the crystalline forms I, II, III, IV, V, or VI of (1R,2R)-7-chloro-3-[2-(2,4-difluorophenyl)-2-hydroxy-1-methyl-3-(1H-1,2,4-triazol-1-yl)propyl]quinazolin-4(3H)-one or a pharmaceutically acceptable salt or derivative thereof. In a particularly preferred embodiment, these methods comprise the use of any one of the pure crystalline Forms I, II, III, IV, V, or VI having a purity of at least 85% by weight, or having not more than 15% by weight of other forms of the compound and any residual solvents, with a purity of at least 90% by weight being most preferred. In an especially preferred embodiment, the present crystalline Forms I, II, III, IV, V, or VI can be used in a method of treating and/or preventing Chagas Disease in a mammal comprising administering to a mammal in need thereof an effective amount of a substantially pure crystalline form of (1R,2R)-7-chloro-3-[2-(2,4-difluorophenyl)-2-hydroxy-1-methyl-3-(1H-1,2,4-triazol-1-yl)propyl]quinazolin-4(3H)-one or a pharmaceutically acceptable salt or derivative thereof. The crystalline Form III, Form IV, or Form VI is particularly preferred in any of these methods in this regard. Form VI is most preferred in this regard. The present subject matter also contemplates use of one or more of the crystalline forms in combination for the methods of treatment described herein.

In another preferred embodiment, the present methods of treatment result in an improvement of the patient's condition, reduction of symptoms, an improvement in the patient's appearance, or combinations thereof. In another preferred embodiment, the present methods of treatment include the use any of the crystalline forms I, II, III, IV, V, or VI of (1R,2R)-7-chloro-3-[2-(2,4-difluorophenyl)-2-hydroxy-1-methyl-3-(1H-1,2,4-triazol-1-yl)propyl]quinazolin-4(3H)-one or a pharmaceutically acceptable salt or derivative thereof, for the preparation of a medicament for treating and/or preventing microbial or fungal infections or disorders, or for treating and/or preventing Chagas Disease, in a mammal in need thereof.

In preferred embodiments, the administration of the present compositions is capable of reducing the number of microbes, preferably pathogenic microbes, in or on the mammal to which it is administered. The microbes that can be acted on by the present compositions are selected from the group consisting of fungi, molds, and combinations thereof. The present compositions are further capable of treating infections of the parasite *Trypanosoma cruzi*.

Preferred, non-limiting examples of such fungi are those selected from the group consisting of *P. ovale, P. oviculare, M. furfur, C. neoformans, S. prolificans, S. shenkii, Epidermophyton floccosum, Microsporum canis, Candida* sp., *Trichophyton* sp., and combinations thereof.

Preferred, non-limiting examples of such *Candida* sp. are those selected from the group consisting of *C. albicans, C. krusei, C. glabrata, C. guillermondii, C. parapsilosis, C. tropicalis*, and combinations thereof.

Preferred, non-limiting examples of such *Trichophyton* sp. are those selected from the group consisting of *T. rubrum, T. mentagrophytes, T. tonsurans, T. violaceum*, and combinations thereof.

Preferred, non-limiting examples of such molds are *Aspergillus* sp.

Preferred, non-limiting examples of such *Aspergillus* sp. are those selected from the group consisting of *A. flavus, A. fumigatus, A. niger*, and combinations thereof.

Several specific skin disorders may also be treated according to the present methods. Exemplary among these skin disorders are seborrheic dermatitis, *Pityrosporum* infections, tinea versicolor, tinea pedis, tinea cruris, tinea corporis, cutaneous candidiasis, onychomycosis, and combinations thereof. Other skin disorders known to those of ordinary skill in the art as effectively treatable by an antimicrobial or antifungal composition are further contemplated as within the scope of the present subject matter.

Further, the present methods provide antimycotic activity against *Pityrosporum* strains, such as *Pityrosporum ovale* and *Pityriasis versicolor.*

In this regard, the present compositions are particularly effective in treating the specific dermatophytes Tinea and/or *Candida* fungi.

Combination Therapy

In another preferred embodiment, the present preferred compositions may be used in combination with an additional pharmaceutical dosage form to enhance their effectiveness in treating a microbial or fungal infection or disorder. In this regard, the present preferred compositions may be administered as part of a regimen additionally including any other pharmaceutical and/or pharmaceutical dosage form known in the art as effective for the treatment of a microbial and/or fungal infection. Similarly, a pharmaceutically active ingredient other than those specified herein can be added to the present preferred compositions to enhance their effectiveness in treating a microbial and/or fungal infection or disorder. Accordingly, this additional pharmaceutically active ingredient or additional pharmaceutical dosage form can be administered to a patient either directly or indirectly, and concomitantly or sequentially, with the preferred compositions described herein.

In this regard, antimicrobial agents other than the (1R,2R)-7-chloro-3-[2-(2,4-difluorophenyl)-2-hydroxy-1-methyl-3-(1H-1,2,4-triazol-1-yl)propyl]quinazolin-4(3H)-one discussed above are additionally contemplated as useful for combination therapy discussed herein. Included among these other antimicrobial agents are those selected from the group consisting of imidazoles, allylamines, triazoles, glucan synthase inhibitors, chitin synthase inhibitors, polyenes, griseofulvin, morpholine derivatives, triazines, pyrimidines, any other antimicrobial azole, pharmaceutically acceptable salts or derivatives thereof, and mixtures thereof. Other antimicrobial agents known in the art as effective upon administration to a patient are further contemplated as effective within the present subject matter.

In a preferred embodiment, these other antimicrobial agents are those selected from the group consisting of amorolfine, amphotericin B, bacitracin, benzalkonium chloride, benzethonium chloride, bifonazole, butenafine, butoconazole, chloroxine, cilofungin, chlordantoin, chlortetracycline, ciclopirox, clindamycin, clioqinol, clotrimazole, econazole, elubiol, faeriefungin, fezatione, fluconazole, flucytosine, fungimycin, gentamicin, griseofulvin, haloprogin, hexylresorcinol, itraconazole, ketoconazole, methylbenzethonium chloride, miconazole, mupirocin, naftifine, nikkomycin Z, nystatin, I-ofloxacin, oxiconazole, oxytetracycline, phenol, polymyxin B, pyrido[3,4-e]-1,2,4-triazine, pyrrolnitrin, quaternary ammonium compounds, salicylic acid, saperconazole, sulconazole, tea tree oil, terbinafine, terconazole, tetracyclines, thiabendazole, ticlatone, tioconazole, tolnaftate, triacetin, triclocarbon, triclosan, undecylenic acid, voriconazole, zinc and sodium pyrithione, a pharmaceutically acceptable salt or derivative thereof, and a mixture thereof. Combinations of any of the foregoing anti-microbial agents or their pharmaceutically acceptable salts or derivatives are contemplated herein.

In one embodiment in this regard, the present preferred compositions and the additional pharmaceutical dosage form can be administered to a patient at the same time. In an alternative embodiment, one of the present preferred compositions and the additional pharmaceutical dosage form can be administered in the morning and the other can be administered in the evening.

In another preferred embodiment, the presently described compounds can be administered to a patient in need thereof in multiple pharmaceutical dosage forms. This combination therapy may maximize the effectiveness of the present composition in treating a microbial or fungal infection or disorder. In one preferred embodiment in this regard, both an oral and a topical composition, each containing Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one, can be administered, either concomitantly or sequentially, to a patient suffering from a microbial and/or fungal infection or disorder. In the alternative, the oral and topical compositions can contain different amorphous and/or crystalline forms of the (1R,2R)-7-chloro-3-[2-(2,4-difluorophenyl)-2-hydroxy-1-methyl-3-(1H-1,2,4-triazol-1-yl)propyl]quinazolin-4(3H)-one compound.

Methods of Production

Each of the crystalline forms 1, II, III, IV, V, and VI of (1R,2R)-7-chloro-3-[2-(2,4-difluorophenyl)-2-hydroxy-1-methyl-3-(1H-1,2,4-triazol-1-yl)propyl]quinazolin-4(3H)-one can be prepared by a separate process to arrive at a separate crystalline form.

For example, the present subject matter relates to a process for preparing a crystalline Form I or II of (1R,2R)-7-chloro-3-[2-(2,4-difluorophenyl)-2-hydroxy-1-methyl-3-(1H-1,2,4-triazol-1-yl)propyl]quinazolin-4(3H)-one comprising:

crystallizing a crystalline Form I or II of (1R,2R)-7-chloro-3-[2-(2,4-difluorophenyl)-2-hydroxy-1-methyl-3-(1H-1,2,4-triazol-1-yl)propyl]quinazolin-4(3H)-one from an amorphous form of (1R,2R)-7-chloro-3-[2-(2,4-difluorophenyl)-2-hydroxy-1-methyl-3-(1H-1,2,4-triazol-1-yl)propyl] quinazolin-4(3H)-one using supercritical $CO_2$ crystallization conditions.

Similarly, the present subject matter relates to a process for preparing a crystalline Form III of (1R,2R)-7-chloro-3-[2-(2,4-difluorophenyl)-2-hydroxy-1-methyl-3-(1H-1,2,4-triazol-1-yl)propyl]quinazolin-4(3H)-one comprising recrystallizing (1R,2R)-7-chloro-3-[2-(2,4-difluorophenyl)-2-hydroxy-1-methyl-3-(1H-1,2,4-triazol-1-yl)propyl]quinazolin-4(3H)-one from a solution or suspension of (1R,2R)-7-chloro-3-[2-(2,4-difluorophenyl)-2-hydroxy-1-methyl-3-(1H-1,2,4-triazol-1-yl)propyl]quinazolin-4(3H)-one in an organic solvent, particularly an organic solvent selected from the group consisting of ethanol, ethyl acetate, dichloromethane, and a combination of ethanol and ethyl acetate. In a most preferred embodiment, the organic solvent is ethanol. In a further preferred embodiment, the (1R,2R)-7-chloro-3-[2-(2,4-difluorophenyl)-2-hydroxy-1-methyl-3-(1H-1,2,4-triazol-1-yl)propyl]quinazolin-4(3H)-one forms a solution in the organic solvent.

Further, the solution or suspension is preferably formed at a temperature of at least 40° C. This solution or suspension can then optionally be cooled to a temperature of about 10° C. to about 20° C. Accordingly, the present subject matter relates to a crystalline form of (1R,2R)-7-chloro-3-[2-(2,4-difluorophenyl)-2-hydroxy-1-methyl-3-(1H-1,2,4-triazol-1-yl)propyl]quinazolin-4(3H)-one comprising the reaction product of (1R,2R)-7-chloro-3-[2-(2,4-difluorophenyl)-2-hydroxy-1-methyl-3-(1H-1,2,4-triazol-1-yl)propyl] quinazolin-4(3H)-one and an organic solvent, particularly an organic solvent selected from the group consisting of ethanol, ethyl acetate, dichloromethane, and a combination of ethanol and ethyl acetate, with ethanol being most preferred. One of skill in the art would understand that combinations of two or more organic solvents, with or without water, may also be useful for the purpose of producing a crystalline form of (1R,2R)-7-chloro-3-[2-(2,4-difluorophenyl)-2-hydroxy-1-methyl-3-(1H-1,2,4-triazol-1-yl)propyl]quinazolin-4(3H)-one. In a preferred embodiment, combinations of two or more organic solvents, without water, may also be useful for the purpose of producing a crystalline form of (1R,2R)-7-chloro-3-[2-(2,4-difluorophenyl)-2-hydroxy-1-methyl-3-(1H-1,2,4-triazol-1-yl)propyl]quinazolin-4(3H)-one in this regard.

In a further preferred embodiment in this regard, the present subject matter relates to a process for preparing a crystalline Form III of (1R,2R)-7-chloro-3-[2-(2,4-difluorophenyl)-2-hydroxy-1-methyl-3-(1H-1,2,4-triazol-1-yl) propyl]quinazolin-4(3H)-one comprising:

adding (1R,2R)-7-chloro-3-[2-(2,4-difluorophenyl)-2-hydroxy-1-methyl-3-(1H-1,2,4-triazol-1-yl)propyl]quinazolin-4(3H)-one to a solvent selected from the group consisting of ethanol, ethyl acetate, dichloromethane, and a combination of ethanol and ethyl acetate to form a solution or suspension; and crystallizing a crystalline Form III of (1R,2R)-7-chloro-3-[2-(2,4-difluorophenyl)-2-hydroxy-1-methyl-3-(1H-1,2,4-triazol-1-yl)propyl]quinazolin-4(3H)-one from said solution or suspension.

In a particularly preferred embodiment in this regard, the (1R,2R)-7-chloro-3-[2-(2,4-difluorophenyl)-2-hydroxy-1-methyl-3-(1H-1,2,4-triazol-1-yl)propyl]quinazolin-4(3H)-one added to the solvent is the amorphous form of (1R,2R)-7-chloro-3-[2-(2,4-difluorophenyl)-2-hydroxy-1-methyl-3-(1H-1,2,4-triazol-1-yl)propyl]quinazolin-4(3H)-one. In a further particularly preferred embodiment, the solvent is ethanol and is used to form a solution of (1R,2R)-7-chloro-3-[2-(2,4-difluorophenyl)-2-hydroxy-1-methyl-3-(1H-1,2,4-triazol-1-yl)propyl]quinazolin-4(3H)-one.

In still another preferred embodiment, the present subject matter relates to a process for preparing a crystalline Form III of (1R,2R)-7-chloro-3-[2-(2,4-difluorophenyl)-2-hydroxy-1-methyl-3-(1H-1,2,4-triazol-1-yl)propyl]quinazolin-4 (3H)-one comprising:

dissolving (1R,2R)-7-chloro-3-[2-(2,4-difluorophenyl)-2-hydroxy-1-methyl-3-(1H-1,2,4-triazol-1-yl)propyl]quinazolin-4(3H)-one in a solvent selected from the group consisting of ethanol, ethyl acetate, dichloromethane, and a combination of ethanol and ethyl acetate to form a solution;

crystallizing crystalline Form III of (1R,2R)-7-chloro-3-[2-(2,4-difluorophenyl)-2-hydroxy-1-methyl-3-(1H-1,2,4-triazol-1-yl)propyl]quinazolin-4(3H)-one; and drying said crystalline Form III of (1R,2R)-7-chloro-3-[2-(2,4-difluorophenyl)-2-hydroxy-1-methyl-3-(1H-1,2,4-triazol-1-yl)propyl]quinazolin-4(3H)-one.

In a preferred embodiment, the (1R,2R)-7-chloro-3-[2-(2,4-difluorophenyl)-2-hydroxy-1-methyl-3-(1H-1,2,4-triazol-1-yl)propyl]quinazolin-4(3H)-one added to the solvent is the amorphous form of (1R,2R)-7-chloro-3-[2-(2,4-difluorophenyl)-2-hydroxy-1-methyl-3-(1H-1,2,4-triazol-1-yl)propyl] quinazolin-4(3H)-one. Further in this regard, the (1R,2R)-7-chloro-3-[2-(2,4-difluorophenyl)-2-hydroxy-1-methyl-3-(1H-1,2,4-triazol-1-yl)propyl]quinazolin-4(3H)-one in the solvent is preferably first filtered and then heated to about 65° C. to about 75° C. in a vacuum to reduce the solvent content. In a preferred embodiment, the (1R,2R)-7-chloro-3-[2-(2,4-difluorophenyl)-2-hydroxy-1-methyl-3-(1H-1,2,4-triazol-1-yl)propyl]quinazolin-4(3H)-one in the solvent is heated to about 70° C. And again, the most preferred solvent used in this regard is ethanol.

In an alternative embodiment, this process further comprises the step of refluxing the solution before crystallizing Form II. In a further alternative embodiment, this process comprises the additional step of filtering the solution after it is refluxed.

In a further preferred embodiment, the present subject matter relates to a process for preparing a crystalline Form III of (1R,2R)-7-chloro-3-[2-(2,4-difluorophenyl)-2-hydroxy-1-methyl-3-(1H-1,2,4-triazol-1-yl)propyl]quinazolin-4(3H)-one comprising:

adding (1R,2R)-7-chloro-3-[2-(2,4-difluorophenyl)-2-hydroxy-1-methyl-3-(1H-1,2,4-triazol-1-yl)propyl]quinazolin-4(3H)-one to an ethanol solvent to form a solution or suspension;

crystallizing crystalline Form III of (1R,2R)-7-chloro-3-[2-(2,4-difluorophenyl)-2-hydroxy-1-methyl-3-(1H-1,2,4-triazol-1-yl)propyl]quinazolin-4(3H)-one; and drying said crystalline Form III of (1R,2R)-7-chloro-3-[2-(2,4-difluorophenyl)-2-hydroxy-1-methyl-3-(1H-1,2,4-triazol-1-yl)propyl]quinazolin-4(3H)-one.

Likewise, the present subject matter relates to a process for preparing a crystalline Form IV of (1R,2R)-7-chloro-3-[2-(2,4-difluorophenyl)-2-hydroxy-1-methyl-3-(1H-1,2,4-triazol-1-yl)propyl]quinazolin-4(3H)-one comprising:

storing an amorphous form of (1R,2R)-7-chloro-3-[2-(2,4-difluorophenyl)-2-hydroxy-1-methyl-3-(1H-1,2,4-triazol-1-yl)propyl]quinazolin-4(3H)-one for 3 months at about 40° C. and 75% HR;

transforming some of said amorphous (1R,2R)-7-chloro-3-[2-(2,4-difluorophenyl)-2-hydroxy-1-methyl-3-(1H-1,2,4-triazol-1-yl)propyl]quinazolin-4(3H)-one to a crystalline Form IV of (1R,2R)-7-chloro-3-[2-(2,4-difluorophenyl)-2-hydroxy-1-methyl-3-(1H-1,2,4-triazol-1-yl)propyl]quinazolin-4(3H)-one during storage; and obtaining said crystalline Form IV of (1R,2R)-7-chloro-3-[2-(2,4-difluorophenyl)-2-hydroxy-1-methyl-3-(1H-1,2,4-triazol-1-yl)propyl]quinazolin-4(3H)-one.

In this regard, this process results in a mixture of both the amorphous form and Form IV of (1R,2R)-7-chloro-3-[2-(2,4-difluorophenyl)-2-hydroxy-1-methyl-3-(1H-1,2,4-triazol-1-yl)propyl]quinazolin-4(3H)-one.

In another preferred embodiment in this regard, the present subject matter relates to an alternative process for preparing a crystalline Form IV of (1R,2R)-7-chloro-3-[2-(2,4-difluorophenyl)-2-hydroxy-1-methyl-3-(1H-1,2,4-triazol-1-yl) propyl]quinazolin-4(3H)-one comprising:

dissolving (1R,2R)-7-chloro-3-[2-(2,4-difluorophenyl)-2-hydroxy-1-methyl-3-(1H-1,2,4-triazol-1-yl)propyl]quinazolin-4(3H)-one in ethanol to form a solution;

adding the solution to water to form a suspension;

stirring the suspension for more than 30 minutes;

obtaining crystalline Form IV of (1R,2R)-7-chloro-3-[2-(2,4-difluorophenyl)-2-hydroxy-1-methyl-3-(1H-1,2,4-triazol-1-yl)propyl]quinazolin-4(3H)-one; and separating said crystalline Form IV of (1R,2R)-7-chloro-3-[2-(2,4-difluorophenyl)-2-hydroxy-1-methyl-3-(1H-1,2,4-triazol-1-yl)propyl]quinazolin-4(3H)-one.

In a particularly preferred embodiment in this regard, the (1R,2R)-7-chloro-3-[2-(2,4-difluorophenyl)-2-hydroxy-1-methyl-3-(1H-1,2,4-triazol-1-yl)propyl]quinazolin-4(3H)-one dissolved in the solvent is the amorphous form of (1R,2R)-7-chloro-3-[2-(2,4-difluorophenyl)-2-hydroxy-1-methyl-3-(1H-1,2,4-triazol-1-yl)propyl]quinazolin-4(3H)-one. However, any form of (1R,2R)-7-chloro-3-[2-(2,4-difluorophenyl)-2-hydroxy-1-methyl-3-(1H-1,2,4-triazol-1-yl)propyl]quinazolin-4(3H)-one may be suitable for this purpose.

In this regard, the amorphous form of (1R,2R)-7-chloro-3-[2-(2,4-difluorophenyl)-2-hydroxy-1-methyl-3-(1H-1,2,4-triazol-1-yl)propyl]quinazolin-4(3H)-one is preferably dissolved in hot ethanol, i.e. ethanol at a temperature of at least 40° C. This solution can then preferably be added to the water at about 5° C. to about 10° C. In an alternative embodiment, the solution can be added to the water at room temperature. Further, the suspension is preferably stirred for at least 6 hours. In one preferred embodiment in this regard, the suspension is stirred for at least 18 hours. In another preferred embodiment in this regard, the suspension is stirred for about 4-5 hours at a temperature of about 28° C.

In another preferred embodiment, the present subject matter relates to a process for preparing a crystalline Form V of (1R,2R)-7-chloro-3-[2-(2,4-difluorophenyl)-2-hydroxy-1-methyl-3-(1H-1,2,4-triazol-1-yl)propyl]quinazolin-4(3H)-one comprising:
    dissolving (1R,2R)-7-chloro-3-[2-(2,4-difluorophenyl)-2-hydroxy-1-methyl-3-(1H-1,2,4-triazol-1-yl)propyl]quinazolin-4(3H)-one in ethyl acetate to form a solution;
    adding hexane to the solution;
    optionally adding diethyl ether to the solution;
    crystallizing Form V of (1R,2R)-7-chloro-3-[2-(2,4-difluorophenyl)-2-hydroxy-1-methyl-3-(1H-1,2,4-triazol-1-yl)propyl]quinazolin-4(3H)-one; and
    separating said crystalline Form V of (1R,2R)-7-chloro-3-[2-(2,4-difluorophenyl)-2-hydroxy-1-methyl-3-(1H-1,2,4-triazol-1-yl)propyl]quinazolin-4(3H)-one.

In a particularly preferred embodiment in this regard, the (1R,2R)-7-chloro-3-[2-(2,4-difluorophenyl)-2-hydroxy-1-methyl-3-(1H-1,2,4-triazol-1-yl)propyl]quinazolin-4(3H)-one dissolved in the solvent is the amorphous form of (1R,2R)-7-chloro-3-[2-(2,4-difluorophenyl)-2-hydroxy-1-methyl-3-(1H-1,2,4-triazol-1-yl)propyl]quinazolin-4(3H)-one. However, any form of (1R,2R)-7-chloro-3-[2-(2,4-difluorophenyl)-2-hydroxy-1-methyl-3-(1H-1,2,4-triazol-1-yl)propyl]quinazolin-4(3H)-one my be suitable for this purpose.

In this regard, the amorphous form of (1R,2R)-7-chloro-3-[2-(2,4-difluorophenyl)-2-hydroxy-1-methyl-3-(1H-1,2,4-triazol-1-yl)propyl]quinazolin-4(3H)-one is preferably dissolved in hot ethyl acetate, i.e. ethyl acetate at a temperature of at least 40° C. Further, the solution can preferably be cooled after addition of the hexane.

The present subject matter also relates to a process for preparing a crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one comprising recrystallizing (1R,2R)-7-chloro-3-[2-(2,4-difluorophenyl)-2-hydroxy-1-methyl-3-(1H-1,2,4-triazol-1-yl)propyl]quinazolin-4(3H)-one from a solution or suspension of (1R,2R)-7-chloro-3-[2-(2,4-difluorophenyl)-2-hydroxy-1-methyl-3-(1H-1,2,4-triazol-1-yl)propyl]quinazolin-4(3H)-one in an organic solvent and water. In one embodiment, the organic solvent is a polar solvent, In a preferred embodiment, the organic solvent is an alcohol. In a particular embodiment, the organic solvent is selected from the group consisting of ethanol, methanol, isopropanol, n-propanol, and acetone. In a most preferred embodiment, the organic solvent is ethanol. One of skill in the art would understand that combinations of two or more organic solvents with water may also be useful for the purpose of producing the crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one. In another preferred embodiment, ethanol is present with water at an ethanol:water ratio ranging from 1:1 to 1:20 by volume. In a further preferred embodiment, ethanol is present with water at an ethanol:water ratio ranging from 1:4 to 1:10 by volume. In this regard, the use of ethanol in the present processes for making Form VI can optionally be replaced with any of these specified organic solvents. In a further preferred embodiment, the (1R,2R)-7-chloro-3-[2-(2,4-difluorophenyl)-2-hydroxy-1-methyl-3-(1H-1,2,4-triazol-1-yl)propyl]quinazolin-4(3H)-one forms a solution in the organic solvent.

In another preferred embodiment, the present subject matter relates to a process for preparing a crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one comprising:
    forming a solution or suspension of (1R,2R)-7-chloro-3-[2-(2,4-difluorophenyl)-2-hydroxy-1-methyl-3-(1H-1,2,4-triazol-1-yl)propyl]quinazolin-4(3H)-one in an aqueous solvent and an organic solvent selected from the group consisting of ethanol, methanol, isopropanol, n-propanol, and acetone
    crystallizing Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one from said solution or suspension; and
    separating said crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one. In a preferred embodiment, the organic solvent is ethanol.

A wide range of ethanol:water ratios may be useful for preparing Form VI solids, including, for example, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19 and 1:20, by volume. In a preferred embodiment, the ratio of ethanol to water ranges from 1:1 to 1:20, by volume. In another preferred embodiment, the ratio of ethanol to water ranges from 1:4 to 1:10, by volume. In further embodiments, these ethanol:water ratios would also apply to the other organic solvents discussed herein.

In another preferred embodiment, the present subject matter relates to a process for preparing a crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one comprising:
    adding (1R,2R)-7-chloro-3-[2-(2,4-difluorophenyl)-2-hydroxy-1-methyl-3-(1H-1,2,4-triazol-1-yl)propyl]quinazolin-4(3H)-one to aqueous ethanol to form a solution or suspension;
    crystallizing a crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one from said solution or suspension; and
    separating said crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one. In a preferred embodiment of the above method, the solution or suspension is formed at a temperature of about 25° C. to about 65° C. In a particularly preferred embodiment, the solution or suspension is formed at a temperature of about 45° C. In a preferred embodiment of the above method, the ratio of ethanol to water ranges from 1:1 to 1:20, by volume. In another preferred embodiment, the ratio of ethanol to water ranges from 1:4 to 1:8, by volume.

In an alternative preferred embodiment, the present subject matter relates to a process for preparing a crystalline Form VI of (1R,2R)-7-chloro-3-[2-(2,4-difluorophenyl)-2-hydroxy-1-methyl-3-(1H-1,2,4-triazol-1-yl)propyl]quinazolin-4 (3H)-one comprising:

adding (1R,2R)-7-chloro-3-[2-(2,4-difluorophenyl)-2-hydroxy-1-methyl-3-(1H-1,2,4-triazol-1-yl)propyl]quinazolin-4(3H)-one to ethanol to form a mixture;

adding said mixture to water to form a solution or suspension;

crystallizing a crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one from said solution or suspension; and separating said crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one. In a particularly preferred embodiment, the mixture of albaconazole and ethanol is a solution of albaconazole in ethanol. In a preferred embodiment of the above method, the ratio of ethanol to water ranges from 1:1 to 1:20, by volume. In another preferred embodiment, the ratio of ethanol to water ranges from 1:4 to 1:8, by volume.

In a preferred embodiment of the above method, the process whereby albaconazole is first added to ethanol to form a mixture, which mixture is then added to water, this process contemplates the additional step of refluxing the solution or suspension of albaconazole in ethanol, before the mixture is added to water. In an alternative preferred embodiment, this process contemplates the additional step of filtering the solution of albaconazole in ethanol, before the mixture is added to water.

In other preferred embodiments in this regard, the slurry of (1R,2R)-7-chloro-3-[2-(2,4-difluorophenyl)-2-hydroxy-1-methyl-3-(1H-1,2,4-triazol-1-yl)propyl]quinazolin-4(3H)-one may be of Form III, Form, IV, Form V, amorphous form, or combinations thereof in aqueous ethanol. However, any form of (1R,2R)-7-chloro-3-[2-(2,4-difluorophenyl)-2-hydroxy-1-methyl-3-(1H-1,2,4-triazol-1-yl)propyl]quinazolin-4(3H)-one may be suitable for this purpose.

In another preferred embodiment, the present subject matter relates to a process for preparing a crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one comprising recrystallizing (1R,2R)-7-chloro-3-[2-(2,4-difluorophenyl)-2-hydroxy-1-methyl-3-(1H-1,2,4-triazol-1-yl)propyl]quinazolin-4(3H)-one from a solution or suspension of (1R,2R)-7-chloro-3-[2-(2,4-difluorophenyl)-2-hydroxy-1-methyl-3-(1H-1,2,4-triazol-1-yl)propyl]quinazolin-4(3H)-one in ethanol and water. In a preferred embodiment, the ethanol mixture is a solution. In a further embodiment, the process further comprises refluxing the solution or suspension of (1R,2R)-7-chloro-3-[2-(2,4-difluorophenyl)-2-hydroxy-1-methyl-3-(1H-1,2,4-triazol-1-yl) propyl]quinazolin-4(3H)-one and ethanol before adding the mixture to water. In another further preferred embodiment, the process further comprises filtering the solution or suspension of (1R,2R)-7-chloro-3-[2-(2,4-difluorophenyl)-2-hydroxy-1-methyl-3-(1H-1,2,4-triazol-1-yl)propyl]quinazolin-4(3H)-one and ethanol before adding the mixture to water.

Form VI may be prepared by slurrying albaconazole in aqueous ethanol or by slowly cooling a saturated aqueous ethanol solution that was seeded. In order to estimate rate of conversion, a slurry experiment of Form III was setup at 45° C. in ethanol-water (1:9), seeded with Form VI and aliquots periodically removed. Solids from the first aliquot removed after ~3 hours were composed of only Form VI by XRPD analysis. A slow cool method was also attempted by cooling a saturated solution of albaconazole in aqueous ethanol that was seeded. Form VI solids were isolated in a 41% yield.

It is further noted that the process for making Form VI is similar to the process for making Form IV. Embodiments of both processes may use the same or similar ratios of ethanol: water and similar mixing and stirring methods. In this regard, it is contemplated herein that, in one process of making Form VI, the (1R,2R)-7-chloro-3-[2-(2,4-difluorophenyl)-2-hydroxy-1-methyl-3-(1H-1,2,4-triazol-1-yl)propyl]quinazolin-4(3H)-one first proceeds through the crystalline Form IV before continuing on to Form VI when starting with the same aqueous solvent-(1R,2R)-7-chloro-3-[2-(2,4-difluorophenyl)-2-hydroxy-1-methyl-3-(1H-1,2,4-triazol-1-yl)propyl] quinazolin-4(3H)-one mixture. In one embodiment, Form IV is an intermediate in the production of Form VI, and the rate of the transformation is a function of the ratio of solvents, temperature, stirring, and time. In general, shorter stirring times and lower stirring temperatures favor formation of Form IV, while longer stir times and higher stirring temperatures favor formation of Form VI. For example, in this regard, Form VI can be obtained in aqueous ethanol at 22° C. after about 6 hours of stirring; and at 28° C. after about 5 hours of stirring. One can also allow the process to proceed longer, for example, 18-24 hr, and still obtain Form VI. Selection of solvent may also affect the time it takes for Form IV to convert to Form VI. For example, in some embodiments, Form VI may form in aqueous ethanol or aqueous acetone in 3-7 hours; or Form VI may form in aqueous methanol or aqueous isopropanol or aqueous n-propanol only after 7-18 hours. In a preferred embodiment, a minimum stirring time of 5 hr is required to prepare Form VI. The presence of Form IV or Form VI can be monitored by an appropriate technique, such as, for example, microscopy or x-ray diffraction, in order to determine the best time/conditions for its isolation Amorphous material of (1R,2R)-7-chloro-3-[2-(2,4-difluorophenyl)-2-hydroxy-1-methyl-3-(1H-1,2,4-triazol-1-yl) propyl]quinazolin-4(3H)-one may be produced by a melt-quench technique and exhibited a glass transition at 75° C. Interconversion of the amorphous form in slurry experiments showed that the predominant resulting crystalline forms were Forms III, IV, V, and VI.

Dosage

Appropriate dosage levels for any of the crystalline forms of any of the active ingredients and/or their specific crystal forms are well known to those of ordinary skill in the art and are selected to maximize the treatment of the previously described microbial and/or fungal conditions. Dosage levels on the order of about 0.001 mg to about 5,000 mg per kilogram body weight of the active ingredient components are known to be useful in the treatment of the diseases, disorders, and conditions contemplated herein. Typically, this effective amount of the active agent will generally comprise from about 0.001 mg to about 100 mg per kilogram of patient body weight per day. Moreover, it will be understood that this dosage of ingredients can be administered in a single or multiple dosage units to provide the desired therapeutic effect.

If desired, other therapeutic agents can be employed in conjunction with those provided in the above-described compositions. The amount of pharmaceutically active ingredients that may be combined with the carrier materials to produce a single dosage form will vary depending upon the host treated, the nature of the disease, disorder, or condition, and the nature of the active ingredients.

The preferred pharmaceutical compositions may be given in a single or multiple doses daily. In a preferred embodiment, the pharmaceutical compositions are given from one to three times daily. Starting with a low dose twice daily and slowly working up to higher doses if needed is a preferred strategy. The amount of pharmaceutically active ingredients that may be combined with the carrier materials to produce a single dosage form will vary depending upon the host treated, the nature of the disease, disorder, or condition, and the nature of the active ingredients.

It is understood, however, that a specific dose level for any particular patient will vary depending upon a variety of factors, including the activity of the specific pharmaceutically active agent; the age, body weight, general health, sex and diet of the patient; the time of administration; the rate of excretion; possible drug combinations; the severity of the particular condition being treated; and the form of administration. One of ordinary skill in the art would appreciate the variability of such factors and would be able to establish specific dose levels using no more than routine experimentation.

The optimal pharmaceutical formulations will be determined by one skilled in the art depending upon considerations such as the particular pharmaceutically active agent combination and the desired dosage. See, for example, "Remington's Pharmaceutical Sciences", 18th ed. (1990, Mack Publishing Co., Easton, Pa. 18042), pp. 1435-1712, the disclosure of which is hereby incorporated by reference. Such formulations may influence the physical state, stability, rate of in vivo release, and rate of in vivo clearance of the essential lipids.

EXAMPLES

The presently presented compounds can be prepared in accordance with the following Examples using commercially available starting materials. The (1R,2R)-7-chloro-3-[2-(2,4-difluorophenyl)-2-hydroxy-1-methyl-3-(1H-1,2,4-triazol-1-yl)propyl]quinazolin-4(3H)-one used in the foregoing examples may be obtained by any of the currently available processes that are well known in the art, such as, for example, the processes described in Bartroli et al., *J. Med. Chem., Vol.* 41, No. 11, pp. 1869-1882 (1998), the contents of which are hereby incorporated by reference in their entirety.

In solution, no crystalline form exists, and thus the physicochemical solution characteristics, i.e. $^1$H NMR spectra, ultraviolet spectra, and specific rotations of the crystalline and amorphous forms of (1R,2R)-7-chloro-3-[2-(2,4-difluorophenyl)-2-hydroxy-1-methyl-3-(1H-1,2,4-triazol-1-yl) propyl]quinazolin-4(3H)-one are the same.

Example 1

Preparation of crystalline Form I of (1R,2R)-7-chloro-3-[2-(2,4-difluorophenyl)-2-hydroxy-1-methyl-3-(1H-1,2,4-triazol-1-yl)propyl]quinazolin-4(3H)-one 1.5 g of amorphous (1R,2R)-7-chloro-3-[2-(2,4-difluorophenyl)-2-hydroxy-1-methyl-3-(1H-1,2,4-triazol-1-yl) propyl]quinazolin-4(3H)-one was dispersed in a column filled with glass beads which act as a disaggregating agent. The column was inserted in an extractor and a flux of supercritical $CO_2$ (SCCO2) was passed (p=250 bar, T=45° C.). A filter was installed at the extractor exit to collect the material once dissolved by the SCCO2. Only 0.15 g of material remained in the column. This material was crystalline, and was shown to have crystalline Form I.

Example 2

Preparation of crystalline Form II of (1R,2R)-7-chloro-3-[2-(2,4-difluorophenyl)-2-hydroxy-1-methyl-3-(1H-1,2,4-triazol-1-yl)propyl]quinazolin-4(3H)-one 0.5 g of amorphous (1R,2R)-7-chloro-3-[2-(2,4-difluorophenyl)-2-hydroxy-1-methyl-3-(1H-1,2,4-triazol-1-yl) propyl]quinazolin-4(3H)-one was dissolved in 200 ml of ethanol. The solution was put in a reactor which was pressurized with $CO_2$ up to p=100 bar and T=40° C. (supercritical conditions). The reactor was depressurized, and any significant amount of product was collected in the outer filter. Once the ethanol was evacuated, 0.52 g of resulting material was collected. The X-ray diffractogram of this sample showed a crystalline pattern. This material was shown to have crystalline Form II.

Example 3

The procedure of Example 1 was repeated but substituting the glass beads with silica sand. The supercritical conditions were p=250 bar and T=52° C. In this case, sample could be collected in the outer filer, which was of crystalline Form II, as well as inside the reactor, which was of crystalline Form I.

Example 4

Preparation of crystalline Form III of (1R,2R)-7-chloro-3-[2-(2,4-difluorophenyl)-2-hydroxy-1-methyl-3-(1H-1,2,4-triazol-1-yl)propyl]quinazolin-4(3H)-one Amorphous (1R,2R)-7-chloro-3-[2-(2,4-difluorophenyl)-2-hydroxy-1-methyl-3-(1H-1,2,4-triazol-1-yl)propyl] quinazolin-4(3H)-one was dissolved in ethanol and recrystallized. The original $^1$H NMR spectrum showed about ½ mol of ethanol. The sample was kept in a capped vial at room temperature for 7 years. After 7 years, the samples NMR spectrum showed a total loss of ethanol. The sample was then shown to have crystalline Form III.

Example 5

The procedure of Example 4 was repeated but substituting the ethanol with ethanol and ethyl acetate, ethyl acetate, or dichloromethane. In each case, the recrystallized sample was shown to have crystalline Form III.

Example 6

Preparation of crystalline Form III of (1R,2R)-7-chloro-3-[2-(2,4-difluorophenyl)-2-hydroxy-1-methyl-3-(1H-1,2,4-triazol-1-yl)propyl]quinazolin-4(3H)-one 6.785 kg of (1R,2R)-7-chloro-3-[2-(2,4-difluorophenyl)-2-hydroxy-1-methyl-3-(1H-1,2,4-triazol-1-yl)propyl] quinazolin-4(3H)-one was dissolved in 17.3 L of ethanol. The solution was cooled at 10-20° C. for about 2 hours. The obtained product was centrifuged and dried in vacuum at 70° C. to obtain 5.796 kg of crystalline (1R,2R)-7-chloro-3-[2-(2,4-difluorophenyl)-2-hydroxy-1-methyl-3-(1H-1,2,4-triazol-1-yl)propyl]quinazolin-4(3H)-one. The product was then shown to have crystalline Form III.

Example 7

Preparation of crystalline Form III of (1R,2R)-7-chloro-3-[2-(2,4-difluorophenyl)-2-hydroxy-1-methyl-3-(1H-1,2,4-triazol-1-yl)propyl]quinazolin-4(3H)-one (1R,2R)-7-chloro-3-[2-(2,4-difluorophenyl)-2-hydroxy-1-methyl-3-(1H-1,2,4-triazol-1-yl)propyl]quinazolin-4(3H)-one was dissolved in an excess of hot ethanol. Charcoal was added and the solution was filtered. The filtered solution was then concentrated in vacuum to a final volume of 2.5-3 L/kg of (1R,2R)-7-chloro-3-[2-(2,4-difluorophenyl)-2-hydroxy-1-methyl-3-(1H-1,2,4-triazol-1-yl)propyl]quinazolin-4(3H)-one. The concentrated solution was then cooled to 5-10° C. and (1R,2R)-7-chloro-3-[2-(2,4-difluorophenyl)-2-hydroxy-1-methyl-3-(1H-1,2,4-triazol-1-yl)propyl]quinazolin-4(3H)-one crystallized. The obtained product was filtered and dried in vacuum at 70° C. to obtain crystalline (1R,2R)-7-chloro-3-[2-(2,4-difluorophenyl)-2-hydroxy-1-methyl-3-(1H-1,2,4-triazol-1-yl)propyl]quinazolin-4(3H)-one. The product was then shown to have crystalline Form III.

Example 8

Preparation of crystalline Form IV of (1R,2R)-7-chloro-3-[2-(2,4-difluorophenyl)-2-hydroxy-1-methyl-3-(1H-1,2,4-triazol-1-yl)propyl]quinazolin-4(3H)-one 8.10 g of (1R,2R)-7-chloro-3-[2-(2,4-difluorophenyl)-2-hydroxy-1-methyl-3-(1H-1,2,4-triazol-1-yl)propyl]quinazolin-4(3H)-one were dissolved in 65 mL of hot ethanol. This solution was added to 400 mL of water at about 5 to about 10° C. The suspension obtained was stirred for 18 hours. 7.07 g of (1R,2R)-7-chloro-3-[2-(2,4-difluorophenyl)-2-hydroxy-1-methyl-3-(1H-1,2,4-triazol-1-yl)propyl]quinazolin-4(3H)-one were obtained. The product was then shown to have crystalline Form IV.

Example 9

Preparation of crystalline Form IV of (1R,2R)-7-chloro-3-[2-(2,4-difluorophenyl)-2-hydroxy-1-methyl-3-(1H-1,2,4-triazol-1-yl)propyl]quinazolin-4(3H)-one 18.15 g of (1R,2R)-7-chloro-3-[2-(2,4-difluorophenyl)-2-hydroxy-1-methyl-3-(1H-1,2,4-triazol-1-yl)propyl]quinazolin-4(3H)-one were dissolved in 130 mL of hot ethanol. This solution was added to 800 mL of water at room temperature. The suspension obtained was stirred for 25 hours at room temperature. The product was filtered and dried in vacuum at 50° C. for 18 hours. 16.98 g of (1R,2R)-7-chloro-3-[2-(2,4-difluorophenyl)-2-hydroxy-1-methyl-3-(1H-1,2,4-triazol-1-yl)propyl]quinazolin-4(3H)-one were obtained. The product was then shown to have crystalline Form IV.

Example 10

Preparation of crystalline Form IV of (1R,2R)-7-chloro-3-[2-(2,4-difluorophenyl)-2-hydroxy-1-methyl-3-(1H-1,2,4-triazol-1-yl)propyl]quinazolin-4(3H)-one 15.0 g of Form II (1R,2R)-7-chloro-3-[2-(2,4-difluorophenyl)-2-hydroxy-1-methyl-3-(1H-1,2,4-triazol-1-yl)propyl]quinazolin-4(3H)-one were dissolved in 90 mL of EtOH 96O at 70° C. and this solution was filtered and added to 810 mL of water contained in a reactor equipped with a heating jacket connected to a thermostatic bath, reflux cooler, discharge valve at the bottom and mechanical stirrer. The suspension was stirred at 160 rpm at 28° C. for 4 h 30 min. The product was filtered (wet weight: 73.34 g) and dried in vacuum at 50° C. 13.59 g of (1R,2R)-7-chloro-3-[2-(2,4-difluorophenyl)-2-hydroxy-1-methyl-3-(1H-1,2,4-triazol-1-yl)propyl]quinazolin-4(3H)-one were obtained. The product was then shown to have crystalline Form IV by using XRPD and DSC.

Example 11

Preparation of crystalline Form V of (1R,2R)-7-chloro-3-[2-(2,4-difluorophenyl)-2-hydroxy-1-methyl-3-(1H-1,2,4-triazol-1-yl)propyl]quinazolin-4(3H)-one 10.0 g of (1R,2R)-7-chloro-3-[2-(2,4-difluorophenyl)-2-hydroxy-1-methyl-3-(1H-1,2,4-triazol-1-yl)propyl]quinazolin-4(3H)-one were dissolved in 30 mL of hot ethyl acetate. 10 mL of Hexane were then added and the solution was slightly cooled. Crystallization was immediately observed. 20 mL of diethyl ether were then added, and the suspension was stirred on an ice bath for one hour. The obtained product was filtered and dried in vacuum at about 40° C. for 8 hours. The product was then dried at 60° C. in vacuum for 24 hours. The product was then shown to have crystalline Form V.

Example 12

Preparation of crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one 100 mL of ethanol and water in a ratio of 1:1 by volume were heated to 45° C. When the temperature stabilized, 5.0 g of Form III (1R,2R)-7-chloro-3-[2-(2,4-difluorophenyl)-2-hydroxy-1-methyl-3-(1H-1,2,4-triazol-1-yl)propyl]quinazolin-4(3H)-one were added. The suspension was stirred, with a magnetic stirrer, for 18 hours at 45° C. The suspension was filtered, at 45° C., with a sintered disc filter funnel, keeping the vacuum for 20 minutes. 3.38 g of wet product was obtained. The product was dried in a vacuum oven at room temperature for 24 hours. The product was then shown to have crystalline Form VI.

Example 13

Preparation of crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one 30.0 g of Form II (1R,2R)-7-chloro-3-[2-(2,4-difluorophenyl)-2-hydroxy-1-methyl-3-(1H-1,2,4-triazol-1-yl)propyl]quinazolin-4(3H)-one were dissolved in 210 mL of absolute ethanol at 65° C. This solution, at 70° C., was added to 1270 mL of water at room temperature. The suspension was stirred at room temperature for 8 hours. The product was dried in vacuum at 50° C. The product was then shown to have crystalline Form VI.

Example 14

Preparation of crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one (1R,2R)-7-chloro-3-[2-(2,4-difluorophenyl)-2-hydroxy-1-methyl-3-(1H-1,2,4-triazol-1-yl)propyl]quinazolin-4(3H)-one (254.4 mg) was added to a glass vial, followed by ethanol (2.04 mL) and warmed to ~70° C. to aid dissolution. Solids dissolved and the resulting solution was filtered through 0.2 μm nylon filter into a clean vial containing water (12.24 mL). A precipitate formed and approximately half of the volume of the suspension was removed. The remaining suspension was agitated at ~60° C. After ~6 hours, an aliquot was removed and solids collected by filtration. The product was then shown to have crystalline Form VI.

Example 15

Preparation of crystalline Form VI of Albaconazole ((1R,2R)-7-chloro-3-[2-(2,4-difluorophenyl)-2-hydroxy-1-methyl-3-(1H-1,2,4-triazol-1-yl)propyl]quinazolin-4(3H)-one)

150 mL of EtOH-water (10:90) was heated to 45° C. When the temperature stabilized, 20.0 g of Albaconazole Form III was added. The suspension was stirred, with a magnetic stirrer, for 18 hours at 45° C. The suspension was cooled to 35° C. in about 20 minutes and then to 5-10° C. with an ice bath for one hour. 21.53 g of wet product was obtained. The product was dried in a vacuum oven at 50° C. for 24 h. The product was then shown to have crystalline form VI.

Example 16

Sufficient (1R,2R)-7-chloro-3-[2-(2,4-difluorophenyl)-2-hydroxy-1-methyl-3-(1H-1,2,4-triazol-1-yl)propyl]quinazolin-4(3H)-one Form III was added to (9:1) water-ethanol mixture (3 mL) such that excess solids remained. The mixture was agitated at ambient temperature overnight and filtered through a 0.2 um nylon filter into a clean vial. Approximately equal amounts of albaconazole Forms III, IV and V were added and the resulting mixture slurried overnight. An aliquot was then removed and solids isolated by filtration. The product was then shown to have crystalline Form VI.

Example 17

10.0 g of Albaconazole were dissolved in 60 mL of MeOH at about reflux temperature and this solution was filtered and added to 540 mL of water contained in a reactor equipped with a heating jacket connected to a thermostatic bath, reflux cooler, discharge valve at the bottom and mechanical stirrer. The suspension was stirred at 160 rpm at 28° C. Samples were taken to follow the process. After 23 hours the product was filtered and dried in vacuum at 50° C. The product was identified as Form VI by its x-ray diffractogram and DSC.

Example 18

10.0 g of Albaconazole were dissolved in 60 mL of isopropanol at about reflux temperature and this solution was filtered and added to 540 mL of water contained in a reactor equipped with a heating jacket connected to a thermostatic bath, reflux cooler, discharge valve at the bottom and mechanical stirrer. The suspension was stirred at 160 rpm at 28° C. Samples were taken follow the process. After 8 hours the product was filtered and dried in vacuum at 50° C. The product was identified as Form VI by its x-ray diffractogram and DSC.

Example 19

10.0 g of Albaconazole were dissolved in 60 mL of acetone at about reflux temperature and this solution was filtered and added to 540 mL of water contained in a reactor equipped with a heating jacket connected to a thermostatic bath, reflux cooler, discharge valve at the bottom and mechanical stirrer. 10 mL of acetone were used for washing the addition funnel and 90 mL of additional water were added. The suspension was stirred at 160 rpm at 28° C. After 1 hour it was observed that the product was agglomerated and the stirring was increased to 200 rpm and the temperature to 30° C. After 6 hours the product was filtered and dried in vacuum at 50° C. The product was identified as Form VI by its x-ray diffractogram and DSC.

Example 20

10.0 g of Albaconazole were dissolved in 60 mL of n-propanol at about reflux temperature and this solution was filtered and added to 540 mL of water contained in a reactor equipped with a heating jacket connected to a thermostatic bath, reflux cooler, discharge valve at the bottom and mechanical stirrer. The suspension was stirred at 160 rpm at 28° C. After 1 hour it was observed that the product was agglomerated and the stirring was increased to 200 rpm and the temperature to 35° C. The suspension was stirred for 17 hours 30 min. The product was filtered and dried in vacuum at 50° C. The product was identified as Form VI by its x-ray diffractogram and DSC.

Example 21

A patient is suffering from onychomycosis. A preferred composition herein is administered to the patient. It would be expected that the patient would improve his/her condition or recover.

Example 22

A patient is suffering from Chagas Disease. A preferred composition herein is administered to the patient. It would be expected that the patient would improve his/her condition or recover.

The present subject matter being thus described, it will be apparent that the same may be modified or varied in many ways. Such modifications and variations are not to be regarded as a departure from the spirit and scope of the present subject matter, and all such modifications and variations are intended to be included within the scope of the following claims.

We claim:

1. A crystalline form of (1R,2R)-7-chloro-3-[2-(2,4-difluorophenyl)-2-hydroxy-1-methyl-3-(1H-1,2,4-triazol-1-yl)propyl]quinazolin-4(3H)-one, selected from the group consisting of Form I, Form II, Form III, Form IV, and Form VI; wherein Form I has at least one property selected from the group consisting of:
  a characteristic X-ray powder diffraction (XRPD) pattern comprising 2-theta positions at about 4.11, 8.22, 9.39, 11.29, 12.41, 13.21, 13.62, 14.43, 14.93 15.7, 16.74, 17.3, 17.57, 18.79, 20.88, 21.88, 22.62, 23.64, 23.82, 25.2, 26.77, 27.21, 28.57, 29.16, 29.97, 30.75, 31.35, 45.28, 48.87, and 55.02+/−0.2;

a characteristic X-ray powder diffraction (XRPD) pattern comprising 2-theta position at about 4.11, 8.22, 9.39, 11.29, 12.41, 13.62, 16.74, 17.57, 18.79, 23.82, and 25.2+/−0.2;

an X-ray powder diffraction pattern substantially similar to that presented in FIG. 1;

an infrared spectra pattern substantially similar to the that presented in FIG. 2;

an infrared spectra pattern comprising spectral lines at 1673.3, 1600.0, 1557.5, 1501.2, 1462.7, 1403.9, 1319.4, 1273.9, 1254.6, 1139.0, 1101.8, 1061.8, 967.2, 902.7, 801.3, 783.6, 664.1, and 630.1 cm$^{-1}$; and a differential scanning calorimetry thermogram substantially similar to that presented in FIG. 3;

Form II has at least one property selected from the group consisting of:

a characteristic X-ray powder diffraction (XRPD) pattern comprising 2-theta positions at about 2.72, 5.31, 6.35, 7.98, 8.37, 9.01, 11.4, 11.7, 12.6, 13.15, 14.42, 14.98, 15.93, 16.77, 17.56, 17.91, 18.86, 19.37, 21.08, 21.78, 22.31, 22.82, 23.84, 25.32, 26, 26.83, 27.35, 28.5, 28.96, 29.38, 30.14, 31.58, 32.41, 33.63, 34.94, and 46.1+/−0.2;

a characteristic X-ray powder diffraction (XRPD) pattern comprising 2-theta positions at about 6.35, 7.98, 8.37, 11.4, 11.7, 12.6, 13.15, 14.42, 14.98, 16.77, 17.56, 18.86, 21.08, 23.84, 25.32, 26.83, and 27.35+/−0.2;

an X-ray powder diffraction pattern substantially similar to that presented in FIG. 4;

an infrared spectra pattern substantially similar to that presented in FIG. 5;

an infrared spectra pattern comprising spectral lines at 1677.0, 1600.0, 1557.5, 1498.8, 1462.3, 1318.2, 1272.4, 1253.0, 1170.2, 1137.7, 1102.0, 1060.7, 967.0, 932.6, 902.0, 857.2, 801.3, 785.1, 693.5, 664.9, and 630.7 cm$^{-1}$; and a differential scanning calorimetry thermogram substantially similar to that presented in FIG. 6;

Form III has at least one property selected from the group consisting of:

a characteristic X-ray powder diffraction (XRPD) pattern comprising 2-theta positions at about 4.08, 5.73, 6.22, 7.77, 8.15, 8.80, 11.25, 11.47, 12.44 13.09, 14.33, 14.68, 14.89, 15.57, 16.35, 16.68, 17.27, 17.63, 18.66, 19.32, 20.85, 22.12, 22.49, 23.58, 24.63, 25.02, 26.65, 27.12, 28.74, 29.11, 29.81, 31.35, and 33.48+/−0.2;

a characteristic X-ray powder diffraction (XRPD) pattern comprising 2-theta positions at about 4.08, 5.73, 6.22, 7.77, 8.15, 8.80, 11.25, 11.47, 12.44 13.09, 15.57, 17.63, 18.66, 20.85, 26.65, and 27.12+/−0.2;

an X-ray powder diffraction pattern substantially similar to that presented in FIG. 7;

an infrared spectra patterns substantially similar to that presented in FIG. 8;

an infrared spectra pattern comprising spectral lines at 1677.0, 1600.0, 1557.5, 1498.3, 1462.6, 1403.0, 1318.4, 1272.5, 1254.1, 1170.0, 1138.7, 1101.5, 1060.2, 1016.4, 966.7, 932.7, 902.4, 855.5, 801.5, 785.8, 694.0, 677.9, 665.4, 631.7, 532.7, and 411.6 cm$^{-1}$; and a differential scanning calorimetry thermogram substantially similar to that presented n FIG. 9 for Form III;

Form IV has at least one property selected from the group consisting of:

a characteristic X-ray powder diffraction (XRPD) pattern comprising 2-theta positions at about 3,74, 4.15, 7.5, 8.33, 9.61, 11.16, 11.61, 12.49, 13.29, 13.64, 14.41, 15.43, 15.74, 16.90, 17.71, 18.25, 18.74, 19.30, 20.43, 21.78, 23.20, 24.26, 24.78, 25.11, 26.03, 26.86, 27.25, 28.00, 29.05, 30.07, 30.91, and 32.05+/−0.2;

a characteristic X-ray powder diffraction (XRPD) pattern comprising 2-theta positions at about 4.15, 7.5, 8.33, 9.61, 11.16, 12.49, 13.29, 13.64, 14.41, 16.90, 18.74, 24.78, and 25.11+/−0.2;

an X-ray powder diffraction pattern substantially similar to that presented in FIG. 10;

an infrared spectra pattern substantially similar to that presented in FIG. 11;

an infrared spectra pattern comprising spectral lines at 1671.0, 1601.0, 1557.5, 1503.3, 1462.7, 1404.1, 1319.8, 1274.4, 1254.9, 1210.2, 1139.1, 1102.1, 1062.2, 967.4, 933.5, 902.8, 845.0, 801.4, 782.9, 693.8, 677.7, 663.6, and 630.2 cm$^{-1}$; and a differential scanning calorimetry thermogram substantially similar to that presented in FIG. 12; and Form VI has at least one property selected from group consisting of:

a characteristic X-ray powder diffraction (XRPD) pattern comprising 2-theta positions at about 10.1, 12.1, 13.3 14.5, 15.0, 16.0 16.6, 17.0, 17.4, 18.8, 19.2, 19.7, 21.1, 22.3, 23.9, 24.2, 24.8, 25.7, 26.7, 27.6, 28.6, 28.9, 29.3, 29.7, 30.0, 30.5, 30.8. 31.3, 33.3, 33.7, 34.3, 35.0, 35.5, 36.5, 36.7, 37.4, and 39.5+/−0.2;

a characteristic X-ray powder diffraction (XRPD) pattern comprising 2-theta positions at about 10.1, 14.5, 16.0, 21.1, 24.8, and 25.7+/−0.2;

a characteristic X-ray powder diffraction (XRPD) pattern comprising 2-theta positions at about 14.5, 16.0, 21.1, 24.8, and 25.7+/−0.2 a characteristic X-ray powder diffraction (XRPD) pattern comprising 2-theta positions at about 21.1, 24.8, and 25.7+/−0.2;

a characteristic X-ray powder diffraction (XRPD) pattern comprising 2-theta positions at about 10.1+/−0.2 an X-ray powder diffraction pattern substantially similar to that presented in FIG. 16;

an infrared spectra substantially similar to that presented in the figure selected from the group consisting of FIG. 17a, FIG. 17b, FIG. 17c, and FIG. 17d;

an infrared spectra having characteristic infrared spectral peak positions at 1607, 1555, 1468, 1400, 1361, 1316, 1280, 1218, 1165, 1102, 1014, 976, 938, 760, and 698 cm$^{-1}$; and a differential scanning calorimetry thermogram substantially similar to that presented in the figure selected from the group consisting of FIG. 18a, FIG. 18b, and FIG 18c.

2. A substantially pure crystalline form of (1R,2R)-7-chloro-3-[2-(2,4-difluorophenyl)-2-hydroxy-1-methyl-3-(1H-1,2,4-triazol-1-yl)propyl]quinazolin-4(3H)-one selected from the group consisting of Form I, Form II, Form III, Form IV, and Form VI; wherein Form I has at least one property selected from the group consisting of:

a characteristic X-ray powder diffraction (XRPD) pattern comprising 2-theta positions at about 4.11, 8.22, 9.39, 11.29, 12.41, 13.21, 13.62, 14.43, 14.93 15.7, 16.74, 17.3, 17.57, 18.79, 20.88, 21.88, 22.62, 23.64, 23.82, 25.2, 26.77, 27.21, 28.57, 29.16, 29.97, 30.75, 31.35, 45.28, 48.87, and 55.02+/−0.2;

a characteristic X-ray powder diffraction (XRPD) pattern comprising 2-theta position at about 4.11, 8.22, 9.39, 11.29, 12.41, 13.62, 16.74, 17.57, 18.79, 23.82, and 25.2+/−0.2;

an X-ray powder diffraction pattern substantially similar to that presented in FIG. 1;

an infrared spectra pattern substantially similar to the that presented in FIG. 2;

an infrared spectra pattern comprising spectral lines at 1673.3, 1600.0, 1557.5, 1501.2, 1462.7, 1403.9, 1319.4, 1273.9, 1254.6, 1139.0, 1101.8, 1061.8, 967.2, 902.7, 801.3, 783.6, 664.1, and 630.1 cm$^{-1}$; and a differential scanning calorimetry thermogram substantially similar to that presented in FIG. 3;

Form II has at least one property selected from the group consisting of:

a characteristic X-ray powder diffraction (XRPD) pattern comprising 2-theta positions at about 2.72, 5.31, 6.35, 7.98, 8.37, 9.01, 11.4, 11.7, 12.6, 13.15, 14.42, 14.98, 15.93, 16.77, 17.56, 17.91, 18.86, 19.37, 21.08, 21.78, 22.31, 22.82, 23.84, 25.32, 26, 26.83, 27.35, 28.5, 28.96, 29.38, 30.14, 31.58, 32.41, 33.63, 34.94, and 46.1+/−0.2;

a characteristic X-ray powder diffraction (XRPD) pattern comprising 2-theta positions at about 6.35, 7.98, 8.37, 11.4, 11.7, 12.6, 13.15, 14.42, 14.98, 16.77, 17.56, 18.86, 21.08, 23.84, 25.32, 26.83, and 27.35+/−0.2;

an X-ray powder diffraction pattern substantially similar to that presented in FIG. 4;

an infrared spectra pattern substantially similar to that presented in FIG. 5;

an infrared spectra pattern comprising spectral lines at 1677.0, 1600.0, 1557.5, 1498.8, 1462.3, 1318.2, 1272.4, 1253.0, 1170.2, 1137.7, 1102.0, 1060.7, 967.0, 932.6, 902.0, 857.2, 801.3, 785.1, 693.5, 664.9, and 630.7 cm$^{-1}$; and a differential scanning calorimetry thermogram substantially similar to that presented in FIG. 6;

Form III has at least one property selected from the group consisting of:

a characteristic X-ray powder diffraction (XRPD) pattern comprising 2-theta positions at about 4.08, 5.73, 6.22, 7.77, 8.15, 8.80, 11.25, 11.47, 12.44 13.09, 14.33, 14.68, 14.89, 15.57, 16.35, 16.68, 17.27, 17.63, 18.66, 19.32, 20.85, 22.12, 22.49, 23.58, 24.63, 25.02, 26.65, 27.12, 28.74, 29.11, 29.81, 31.35, and 33.48+/−0.2;

a characteristic X-ray powder diffraction (XRPD) pattern comprising 2-theta positions at about 4.08, 5.73, 6.22, 7.77, 8.15, 8.80, 11.25, 11.47, 12.44 13.09, 15.57, 17.63, 18.66, 20.85, 26.65, and 27.12+/−0.2;

an X-ray powder diffraction pattern substantially similar to that presented in FIG. 7;

an infrared spectra patterns substantially similar to that presented in FIG. 8;

an infrared spectra pattern comprising spectral lines at 1677.0, 1600.0, 1557.5, 1498.3, 1462.6, 1403.0, 1318.4, 1272.5, 1254.1, 1170.0, 1138.7, 1101.6, 1060.2, 1016.4, 966.7, 932.7, 902.4, 855.5, 801.5, 785.8, 694.0, 677.9, 665.4, 631.7, 532.7, and 411.6 cm$^{-1}$; and a differential scanning calorimetry thermogram substantially similar to that presented in FIG. 9 for Form III;

Form IV has at least one property selected from the group consisting of:

a characteristic X-ray powder diffraction (XRPD) pattern comprising 2-theta positions at about 3.74, 4.15, 7.5, 8.33, 9.61, 11.16, 11.61, 12.49, 13.29, 13.64, 14.41, 15.43, 15.74, 16.90, 17.71, 18.25, 18.74, 19.30, 20.43, 21.78, 23.20, 24.26, 24.78, 25.11, 26.03, 26.86, 27.25, 28.00, 29.05, 30.07, 30.91, and 32.05+/−0.2;

a characteristic X-ray powder diffraction (XRPD) pattern comprising 2-theta positions at about 4.15, 7.5, 8.33, 9.61, 11.16, 12.49, 13.29, 13.64, 14.41, 16.90, 18.74, 24.78, and 25.11+/−0.2;

an X-ray powder diffraction pattern substantially similar to that presented in FIG. 10;

an infrared spectra pattern substantially similar to that presented in FIG. 11;

an infrared spectra pattern comprising spectral lines at 1671.0, 1601.0, 1557.5, 1503.3, 1462.7, 1404.1, 1319.8, 1274.4, 1254.9, 1210.2, 1139.1, 1102.1, 1062.2, 967.4, 933.5, 902.8, 845.0, 801.4, 782.9, 693.8, 677.7, 663.6, and 630.2 cm$^{-1}$; and a differential scanning calorimetry thermogram substantially similar to that presented in FIG. 12; and Form VI has at least one property selected from group consisting of:

a characteristic X-ray powder diffraction (XRPD) pattern comprising 2-theta positions at about 10.1, 12.1, 13.3 14.5, 15.0, 16.0 16.6, 17.0, 17.4, 18.8, 19.2, 19.7, 21.1, 22.3, 23.9, 24.2, 24.8, 25.7, 26.7, 27.6, 28.6, 28.9, 29.3, 29.7, 30.0, 30.5, 30.8. 31.3, 33.3, 33.7, 34.3, 35.0, 35.5, 36.5, 36.7, 37.4, and 39.5+/−0.2;

a characteristic X-ray powder diffraction (XRPD) pattern comprising 2-theta positions at about 10.1, 14.5, 16.0, 21.1, 24.8, and 25.7+/−0.2;

a characteristic X-ray powder diffraction (XRPD) pattern comprising 2-theta positions at about 14.5, 16.0, 21.1, 24.8, and 25.7+/−0.2 a characteristic X-ray powder diffraction (XRPD) pattern comprising 2-theta positions at about 21.1, 24.8, and 25.7+/−0.2;

a characteristic X-ray powder diffraction (XRPD) pattern comprising 2-theta positions at about 10.1+/−0.2 an X-ray powder diffraction pattern substantially similar to that presented in FIG. 16;

an infrared spectra substantially similar to that presented in the figure selected from the group consisting of FIG. 17a, FIG. 17b, FIG. 17c, and FIG. 17d;

an infrared spectra having characteristic infrared spectral peak positions at 1607, 1555, 1468, 1400, 1361, 1316, 1280, 1218, 1165, 1102, 1014, 976, 938, 760, and 698 cm$^{-1}$; and a differential scanning calorimetry thermogram substantially similar to that presented in the figure selected from the group consisting of FIG. 18a, FIG. 18b, and FIG. 18c.

3. The substantially pure crystalline form of claim 2, wherein the crystalline Form VI of (1R,2R)-7-chloro-3-[2-(2, 4-difluorophenyl)-2-hydroxy-1-methyl-3-(1H-1,2,4-triazol-1-yl)propyl]quinazolin-4(3H)-one has a characteristic X-ray powder diffraction (XRPD) pattern selected from the group consisting of (F1) 2-theta positions at about 10.1, 14.5, 16.0, 21.1, 24.8, and 25.7+/−0.2; (F2) 2-theta positions at about 14.5, 16.0, 21.1, 24.8, and 25.7+/−0.2; (F3) 2-theta positions at about 21.1, 24.8, and 25.7+/−0.2; and (F4) a 2-theta position at about 10.1+/−0.2.

4. The substantially pure crystalline form of (1R,2R)-7-chloro-3-[2-(2,4-difluorophenyl)-2-hydroxy-1-methyl-3-(1H-1,2,4-triazol-1-yl)propyl]quinazolin-4(3H)-one of claim 2, which has less than about 10% by weight of a different crystalline form or an amorphous form of (1R,2R)-7-chloro-3-[2-(2,4-difluorophenyl)-2-hydroxy-1-methyl-3-(1H-1,2,4-triazol-1-yl)propyl]quinazolin-4(3H)-one as determined on a % weight basis.

5. The substantially pure crystalline form of claim 2, wherein the crystalline form of (1R,2R)-7-chloro-3-[2-(2,4-difluorophenyl)-2-hydroxy-1-methyl-3-(1H-1,2,4-triazol-1-yl)propyl]quinazolin-4(3H)-one has at least 90% purity as defined by X-ray powder diffraction.

6. The substantially pure crystalline form of claim 2, which has less than about 10% by weight of any residual solvent.

7. The substantially pure crystalline form of claim 2, wherein the crystalline Form VI of (1R,2R)-7-chloro-3-[2-(2,4-difluorophenyl)-2-hydroxy-1-methyl-3-(1H-1,2,4-triazol-1-yl)propyl]quinazolin-4(3H)-one is storage stable for at least 6 months at about 25° C. and 60% relative humidity.

8. A pharmaceutical composition comprising an effective amount of the substantially pure crystalline form of (1R,2R)-7-chloro-3-[2-(2,4-difluorophenyl)-2-hydroxy-1-methyl-3-(1H-1,2,4-triazol-1-yl)propyl]quinazolin-4(3H)-one of claim 2 and a pharmaceutically acceptable carrier.

9. The pharmaceutical composition of claim 8, wherein said substantially pure crystalline form of (1R,2R)-7-chloro-3-[2-(2,4-difluorophenyl)-2-hydroxy-1-methyl-3-(1H-1,2,4-triazol-1-yl)propyl]quinazolin-4(3H)-one comprises at least 95% by weight of the substantially pure crystalline form of (1R,2R)-7-chloro-3-[2-(2,4-difluorophenyl)-2-hydroxy-1-methyl-3-(1H-1,2,4-triazol-1-yl)propyl]quinazolin-4(3H)-one.

10. A method of treating a microbial or fungal infection in a mammal comprising administering to a mammal in need thereof an effective amount of the substantially pure crystalline form of (1R,2R)-7-chloro-3-[2-(2,4-difluorophenyl)-2-hydroxy-1-methyl-3-(1H-1,2,4-triazol-1-yl)propyl]quinazolin-4(3H)-one of claim 2.

11. A method of treating Chagas Disease in a mammal comprising administering to a mammal in need thereof an effective amount of the substantially pure crystalline form of (1R,2R)-7-chloro-3-[2-(2,4-difluorophenyl)-2-hydroxy-1-methyl-3-(1H-1,2,4-triazol-1-yl)propyl]quinazolin-4(3H)-one of claim 2.

12. A substantially pure crystalline form of (1R,2R)-7-chloro-3-[2-(2,4-difluorophenyl)-2-hydroxy-1-methyl-3-(1H-1,2,4-triazol-1-yl)propyl]quinazolin-4(3H)-one Form I; wherein Form I has at least one property selected from the group consisting of:
  a characteristic X-ray powder diffraction (XRPD) pattern comprising 2-theta positions at about 4.11, 8.22, 9.39, 11.29, 12.41, 13.21, 13.62, 14.43, 14.93 15.7, 16.74, 17.3, 17.57, 18.79, 20.88, 21.88, 22.62, 23.64, 23.82, 25.2, 26.77, 27.21, 28.57, 29.16, 29.97, 30.75, 31.35, 45.28, 48.87, and 55.02+/−0.2;
  a characteristic X-ray powder diffraction (XRPD) pattern comprising 2-theta position at about 4.11, 8.22, 9.39, 11.29, 12.41, 13.62, 16.74, 17.57, 18.79, 23.82, and 25.2+/−0.2;
  an X-ray powder diffraction pattern substantially similar to that presented in FIG. 1;
  an infrared spectra pattern substantially similar to the that presented in FIG. 2;
  an infrared spectra pattern comprising spectral lines at 1673.3, 1600.0, 1557.5, 1501.2, 1462.7, 1403.9, 1319.4, 1273.9, 1254.6, 1139.0, 1101.8, 1061.8, 967.2, 902.7, 801.3, 783.6, 664.1, and 630.1 cm$^{-1}$; and
  a differential scanning calorimetry thermogram substantially similar to that presented in FIG. 3.

13. A substantially pure crystalline form of (1R,2R)-7-chloro-3-[2-(2,4-difluorophenyl)-2-hydroxy-1-methyl-3-(1H-1,2,4-triazol-1-yl)propyl]quinazolin-4(3H)-one Form II; wherein Form II has at least one property selected from the group consisting of:
  a characteristic X-ray powder diffraction (XRPD) pattern comprising 2-theta positions at about 2.72, 5.31, 6.35, 7.98, 8.37, 9.01, 11.4, 11.7, 12.6, 13.15, 14.42, 14.98, 15.93, 16.77, 17.56, 17.91, 18.86, 19.37, 21.08, 21.78, 22.31, 22.82, 23.84, 25.32, 26, 26.83, 27.35, 28.5, 28.96, 29.38, 30.14, 31.58, 32.41, 33.63, 34.94, and 46.1+/−0.2;
  a characteristic X-ray powder diffraction (XRPD) pattern comprising 2-theta positions at about 6.35, 7.98, 8.37, 11.4, 11.7, 12.6, 13.15, 14.42, 14.98, 16.77, 17.56, 18.86, 21.08, 23.84, 25.32, 26.83, and 27.35+/−0.2;
  an X-ray powder diffraction pattern substantially similar to that presented in FIG. 4;
  an infrared spectra pattern substantially similar to that presented in FIG. 5;
  an infrared spectra pattern comprising spectral lines at 1677.0, 1600.0, 1557.5, 1498.8, 1462.3, 1318.2, 1272.4, 1253.0, 1170.2, 1137.7, 1102.0, 1060.7, 967.0, 932.6, 902.0, 857.2, 801.3, 785.1, 693.5, 664.9, and 630.7 cm$^{-1}$; and
  a differential scanning calorimetry thermogram substantially similar to that presented in FIG. 6.

14. A substantially pure crystalline form of (1R,2R)-7-chloro-3-[2-(2,4-difluorophenyl)-2-hydroxy-1-methyl-3-(1H-1,2,4-triazol-1-yl)propyl]quinazolin-4(3H)-one Form III; wherein Form III has at least one property selected from the group consisting of:
  a characteristic X-ray powder diffraction (XRPD) pattern comprising 2-theta positions at about 4.08, 5.73, 6.22, 7.77, 8.15, 8.80, 11.25, 11.47, 12.44 13.09, 14.33, 14.68, 14.89, 15.57, 16.35, 16.68, 17.27, 17.63, 18.66, 19.32, 20.85, 22.12, 22.49, 23.58, 24.63, 25.02, 26.65, 27.12, 28.74, 29.11, 29.81, 31.35, and 33.48+/−0.2;
  a characteristic X-ray powder diffraction (XRPD) pattern comprising 2-theta positions at about 4.08, 5.73, 6.22, 7.77, 8.15, 8.80, 11.25, 11.47, 12.44 13.09, 15.57, 17.63, 18.66, 20.85, 26.65, and 27.12+/−0.2;
  an X-ray powder diffraction pattern substantially similar to that presented in FIG. 7;
  an infrared spectra patterns substantially similar to that presented in FIG. 8;
  an infrared spectra pattern comprising spectral lines at 1677.0, 1600.0, 1557.5, 1498.3, 1462.6, 1403.0, 1318.4, 1272.5, 1254.1, 1170.0, 1138.7, 1101.6, 1060.2, 1016.4, 966.7, 932.7, 902.4, 855.5, 801.5, 785.8, 694.0, 677.9, 665.4, 631.7, 532.7, and 411.6 cm$^{-1}$; and
  a differential scanning calorimetry thermogram substantially similar to that presented in FIG. 9.

15. A substantially pure crystalline form of (1R,2R)-7-chloro-3-[2-(2,4-difluorophenyl)-2-hydroxy-1-methyl-3-(1H-1,2,4-triazol-1-yl)propyl]quinazolin-4(3H)-one Form IV; wherein Form IV has at least one property selected from the group consisting of:

a characteristic X-ray powder diffraction (XRPD) pattern comprising 2-theta positions at about 3.74, 4.15, 7.5, 8.33, 9.61, 11.16, 11.61, 12.49, 13.29, 13.64, 14.41, 15.43, 15.74, 16.90, 17.71, 18.25, 18.74, 19.30, 20.43, 21.78, 23.20, 24.26, 24.78, 25.11, 26.03, 26.86, 27.25, 28.00, 29.05, 30.07, 30.91, and 32.05+/−0.2;

a characteristic X-ray powder diffraction (XRPD) pattern comprising 2-theta positions at about 4.15, 7.5, 8.33, 9.61, 11.16, 12.49, 13.29, 13.64, 14.41, 16.90, 18.74, 24.78, and 25.11+/−0.2;

an X-ray powder diffraction pattern substantially similar to that presented in FIG. 10;

an infrared spectra pattern substantially similar to that presented in FIG. 11;

an infrared spectra pattern comprising spectral lines at 1671.0, 1601.0, 1557.5, 1503.3, 1462.7, 1404.1, 1319.8, 1274.4, 1254.9, 1210.2, 1139.1, 1102.1, 1062.2, 967.4, 933.5, 902.8, 845.0, 801.4, 782.9, 693.8, 677.7, 663.6, and 630.2 cm$^{-1}$; and a differential scanning calorimetry thermogram substantially similar to that presented in FIG. 12.

16. A substantially pure crystalline form of (1R,2R)-7-chloro-3-[2-(2,4-difluorophenyl)-2-hydroxy-1-methyl-3-(1H-1,2,4-triazol-1-yl)propyl]quinazolin-4(3H)-one Form VI; wherein Form VI has at least one property selected from group consisting of:

a characteristic X-ray powder diffraction (XRPD) pattern comprising 2-theta positions at about 10.1, 12.1, 13.3 14.5, 15.0, 16.0 16.6, 17.0, 17.4, 18.8, 19.2, 19.7, 21.1, 22.3, 23.9, 24.2, 24.8, 25.7, 26.7, 27.6, 28.6, 28.9, 29.3, 29.7, 30.0, 30.5, 30.8. 31.3, 33.3, 33.7, 34.3, 35.0, 35.5, 36.5, 36.7, 37.4, and 39.5+/−0.2;

a characteristic X-ray powder diffraction (XRPD) pattern comprising 2-theta positions at about 10.1, 14.5, 16.0, 21.1, 24.8, and 25.7+/−0.2;

a characteristic X-ray powder diffraction (XRPD) pattern comprising 2-theta positions at about 14.5, 16.0, 21.1, 24.8, and 25.7+/−0.2 a characteristic X-ray powder diffraction (XRPD) pattern comprising 2-theta positions at about 21.1, 24.8, and 25.7+/−0.2;

a characteristic X-ray powder diffraction (XRPD) pattern comprising 2-theta positions at about 10.1+/−0.2 an X-ray powder diffraction pattern substantially similar to that presented in FIG. 16;

an infrared spectra substantially similar to that presented in the figure selected from the group consisting of FIG. 17*a*, FIG. 17*b*, FIG. 17*c*, and FIG. 17*d;* an infrared spectra having characteristic infrared spectral peak positions at 1607, 1555, 1468, 1400, 1361, 1316, 1280, 1218, 1165, 1102, 1014, 976, 938, 760, and 698 cm$^{-1}$; and a differential scanning calorimetry thermogram substantially similar to that presented in the figure selected from the group consisting of FIG. 18*a*, FIG. 18*b*, and FIG 18*c*.

* * * * *